(12) United States Patent
Clem et al.

(10) Patent No.: US 11,723,798 B2
(45) Date of Patent: Aug. 15, 2023

(54) SUB-RETINAL TANGENTIAL NEEDLE CATHETER GUIDE AND INTRODUCER

(71) Applicant: GYROSCOPE THERAPEUTICS LIMITED, Stevenage (GB)

(72) Inventors: Michael F. Clem, South Lebanon, OH (US); Benjamin L. Ko, Cincinnati, OH (US); Robert H. Roth, Cincinnati, OH (US); Daniel J. Abbott, Maple Valley, WA (US); Thomas E. Meyer, Philadelphia, PA (US); Paul D. Gordon, Shreve, OH (US)

(73) Assignee: Gyroscope Therapeutics Limited, London (GB)

( * ) Notice: Subject to any disclaimer, the term of this patent is extended or adjusted under 35 U.S.C. 154(b) by 376 days.

(21) Appl. No.: 17/034,707

(22) Filed: Sep. 28, 2020

(65) Prior Publication Data

US 2021/0007890 A1 Jan. 14, 2021

Related U.S. Application Data

(63) Continuation of application No. 15/897,266, filed on Feb. 15, 2018, now Pat. No. 10,821,021, which is a
(Continued)

(51) Int. Cl.
*A61F 9/00* (2006.01)
*A61M 25/06* (2006.01)
(Continued)

(52) U.S. Cl.
CPC .......... *A61F 9/0017* (2013.01); *A61F 9/0008* (2013.01); *A61F 9/0026* (2013.01);
(Continued)

(58) Field of Classification Search
CPC ..... A61F 9/0008; A61F 9/0026; A61M 25/06; A61M 25/065
See application file for complete search history.

(56) References Cited

U.S. PATENT DOCUMENTS

| 5,409,457 A | 4/1995 | del Cerro et al. |
| 5,425,730 A | 6/1995 | Luloh |

(Continued)

FOREIGN PATENT DOCUMENTS

| CN | 101414042 A | 4/2009 |
| CN | 101631585 A | 1/2010 |

(Continued)

OTHER PUBLICATIONS

Chinese Office Action dated Jan. 6, 2022, for Application No. 201911282075.2, 2 pages.

(Continued)

*Primary Examiner* — Emily L Schmidt
(74) *Attorney, Agent, or Firm* — Frost Brown Todd LLP

(57) ABSTRACT

An apparatus includes a body, a needle, a catheter, and an actuator assembly. The needle extends distally from the body. The needle has an inner wall defining a needle lumen. The needle lumen is in fluid communication with a fluid port of the body. The catheter is slidably disposed in the needle lumen. The catheter has a catheter lumen. The first actuator assembly is configured to translate the catheter within and relative to the needle. The apparatus may also include an actuator assembly that is configured to rotate the needle relative to the body. The apparatus may be used to first deliver a leading bleb of fluid to the subretinal space in a patient's eye via the needle. The apparatus may then be used to deliver a therapeutic agent to the subretinal space in the patient's eye via the catheter.

19 Claims, 79 Drawing Sheets

Related U.S. Application Data continuation of application No. 14/726,977, filed on Jun. 1, 2015, now Pat. No. 9,925,088.

(60) Provisional application No. 62/008,756, filed on Jun. 6, 2014.

(51) Int. Cl.
 A61M 25/02 (2006.01)
 A61M 5/158 (2006.01)

(52) U.S. Cl.
 CPC ........ *A61M 25/02* (2013.01); *A61M 25/0662* (2013.01); *A61M 5/158* (2013.01); *A61M 2025/0286* (2013.01); *A61M 2210/0612* (2013.01)

(56) References Cited

U.S. PATENT DOCUMENTS

| | | | |
|---|---|---|---|
| 5,860,986 A | 1/1999 | Reich et al. | |
| 6,368,315 B1 | 4/2002 | Gillis et al. | |
| 6,761,724 B1 | 7/2004 | Zrenner et al. | |
| 6,824,532 B2 | 11/2004 | Gillis et al. | |
| 7,189,245 B2 | 3/2007 | Kaplan | |
| 7,207,980 B2 | 4/2007 | Christian et al. | |
| 7,413,734 B2 | 8/2008 | Mistry et al. | |
| 7,824,372 B1 | 11/2010 | Kurup | |
| 8,197,435 B2 | 6/2012 | Prausnitz et al. | |
| 8,425,473 B2 | 4/2013 | Ho et al. | |
| 9,925,088 B2 | 3/2018 | Clem et al. | |
| 10,821,021 B2 | 11/2020 | Clem et al. | |
| 2002/0198511 A1* | 12/2002 | Varner | A61F 9/0017 604/521 |
| 2003/0060763 A1 | 3/2003 | Penfold et al. | |
| 2004/0044310 A1 | 3/2004 | Suzuki | |
| 2005/0143363 A1 | 6/2005 | de Juan et al. | |
| 2005/0288697 A1* | 12/2005 | Tei | A61F 9/0017 606/166 |
| 2007/0191863 A1 | 8/2007 | De Juan et al. | |
| 2008/0058704 A1 | 3/2008 | Hee et al. | |
| 2008/0065055 A1 | 3/2008 | Jones et al. | |
| 2008/0154204 A1 | 6/2008 | Varner et al. | |
| 2008/0281292 A1 | 11/2008 | Hickingbotham et al. | |
| 2009/0227934 A1 | 9/2009 | Euteneuer et al. | |
| 2010/0081707 A1 | 4/2010 | Ali et al. | |
| 2010/0305514 A1 | 12/2010 | Valenti et al. | |
| 2012/0140180 A1 | 6/2012 | Futamura | |
| 2012/0191064 A1* | 7/2012 | Conston | A61F 9/00727 604/523 |
| 2012/0257167 A1 | 10/2012 | Gille et al. | |
| 2012/0271272 A1 | 10/2012 | Hammack et al. | |
| 2013/0103145 A1 | 4/2013 | John et al. | |
| 2013/0216623 A1 | 8/2013 | Yamamoto et al. | |
| 2013/0245600 A1 | 9/2013 | Yamamoto et al. | |
| 2013/0253438 A1 | 9/2013 | Badawi et al. | |
| 2015/0164687 A1* | 6/2015 | Kashani | A61M 5/178 604/154 |
| 2015/0209180 A1 | 7/2015 | Prausnitz et al. | |
| 2015/0223977 A1 | 8/2015 | Oberkircher et al. | |
| 2015/0258120 A1 | 9/2015 | Zarnitsyn et al. | |
| 2016/0143776 A1* | 5/2016 | Rotenstreich | A61F 9/0017 604/21 |
| 2017/0095369 A1 | 4/2017 | Andino et al. | |
| 2017/0333416 A1 | 11/2017 | Zarnitsyn et al. | |
| 2018/0042765 A1 | 2/2018 | Noronha et al. | |

FOREIGN PATENT DOCUMENTS

| | | |
|---|---|---|
| CN | 101869496 A | 1/2010 |
| CN | 102238972 A | 11/2011 |
| CN | 102488959 A | 6/2012 |
| CN | 102548505 A | 7/2012 |
| CN | 103096844 A | 5/2013 |
| CN | 103327939 A | 9/2013 |
| CN | 203468803 U | 3/2014 |
| JP | 2003-339756 A | 12/2003 |
| JP | 2007-007332 A | 1/2007 |
| JP | 2012-532692 A | 12/2012 |
| WO | WO 2010/132751 A1 | 11/2010 |
| WO | WO 2013/059678 A1 | 4/2013 |
| WO | WO 2014/035862 A1 | 3/2014 |
| WO | WO 2017/042584 A1 | 3/2017 |

OTHER PUBLICATIONS

Kang, Se Woong, et al. "A new instrument for drainage or injection of fluid within subretinal space." *Retina* 23.5 (2003): 661-666.

Komáromy, András M., et al. "Application of a new subretinal injection device in the dog." *Cell transplantation* 15.6 (2006): 511-519.

Olsen, Timothy W., et al. "Cannulation of the suprachoroidal space: a novel drug delivery methodology to the posterior segment." *American journal of ophthalmology* 142.5 (2006): 777-787.

Patel, S. R., et al. "Intraocular Pharmacokinetics of Suprachoroidal Drug Delivery Administered Using Hollow Microneedles." *Investigative Ophthalmology & Visual Science* 51.13 (2010): 3796-3796.

Patel, S., et al. "Suprachoroidal Drug Delivery Using Microneedles." *Investigative Ophthalmology & Visual Science* 49.13 (2008): 5006-5006.

Patel, Samirkumar R., et al. "Suprachoroidal drug delivery to the back of the eye using hollow microneedles." *Pharmaceutical research* 28.1 (2011): 166-176.

Peden, M. C., et al. "Safety Study of Ab-Externo AAV Gene Therapy Delivery to the Subretinal and Suprachoroidal Space Using a 250 Micron Flexible Microcatheter." *Investigative Ophthalmology & Visual Science* 50.13 (2009): 1450-1450.

Schanze, Thomas, et al. "Implantation and testing of subretinal film electrodes in domestic pigs." *Experimental eye research* 82.2 (2006): 332-340.

Soni, M. H., and A. K. Tyagi. "Induction of Choroidal Detachment: A New Surgical Technique for Choroidal Biopsy." *Investigative Ophthalmology & Visual Science* 46.13 (2005): 5438-5438.

Chinese First Office Action dated Dec. 4, 2018 for Application No. 201580041949.9, 7 pages.

Chinese Second Office Action dated Jun. 5, 2019 for Application No. 201580041949.9, 5 pages.

Extended European Search Report dated Jul. 7, 2020 for Application No. 20170732.0, 8 pages.

International Search Report and Written Opinion dated Nov. 3, 2015 for Application No. PCT/US2015/033683, 17 pgs.

International Preliminary Report on Patentability dated Dec. 6, 2016 for Application No. PCT/US2015/033683, 12 pgs.

Japanese Notification of Reasons for Refusal dated Mar. 12, 2019 for Application No. 2016-571260, 6 pages.

U.S. Appl. No. 62/008,756, filed Jun. 6, 2014.

Chalberg, Thomas W., et al. "Gene transfer to rabbit retina with electron avalanche transfection." *Investigative ophthalmology & visual science* 47.9 (2006): 4083-4090.

Einmahl, Suzanne, et al. "Evaluation of a novel biomaterial in the suprachoroidal space of the rabbit eye." *Investigative ophthalmology & visual science* 43.5 (2002): 1533-1539.

Geroski, Dayle H., and Henry F. Edelhauser. "Drug delivery for posterior segment eye disease." *Investigative ophthalmology & visual science* 41.5 (2000): 961-964.

Machemer, Robert, and Ulrich H. Steinhorst. "Retinal separation, retinotomy, and macular relocation I. Experimental studies in the rabbit eye." *Graefe's archive for clinical and experimental ophthalmology* 231.11 (1993): 629-634.

Sternberg, Paul, et al. "Controlled aspiration of subretinal fluid in the diagnosis of carcinoma metastatic to the choroid." *Archives of Ophthalmology* 102.11 (1984): 1622-1625.

Brazil Office Action dated Feb. 24, 2022, for Application No. BR122020011958-6, 8 pages.

* cited by examiner

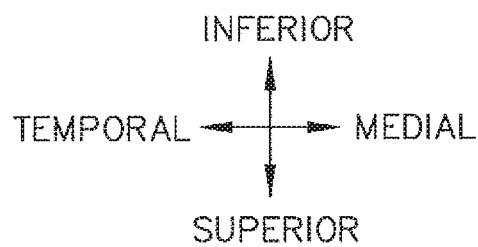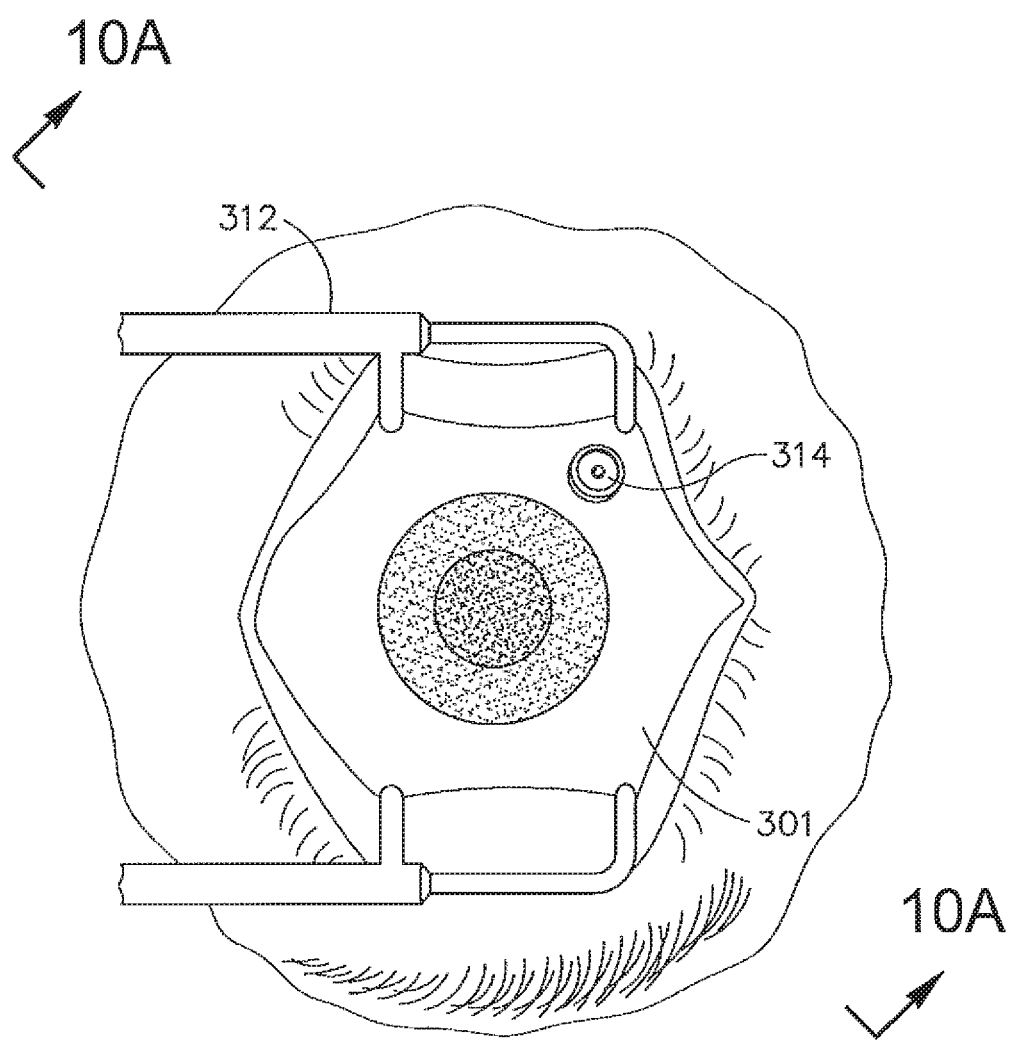
Fig. 9A

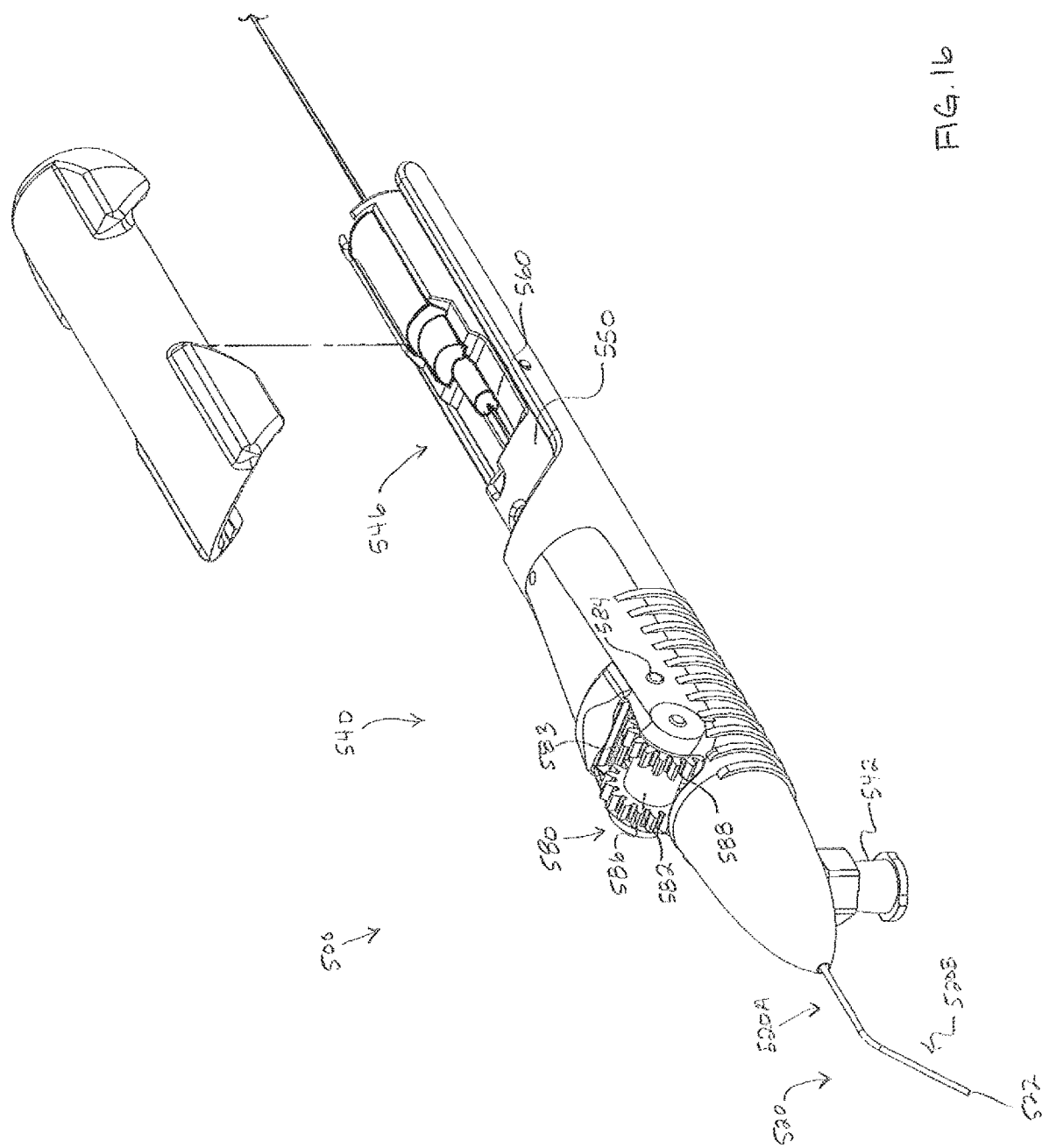

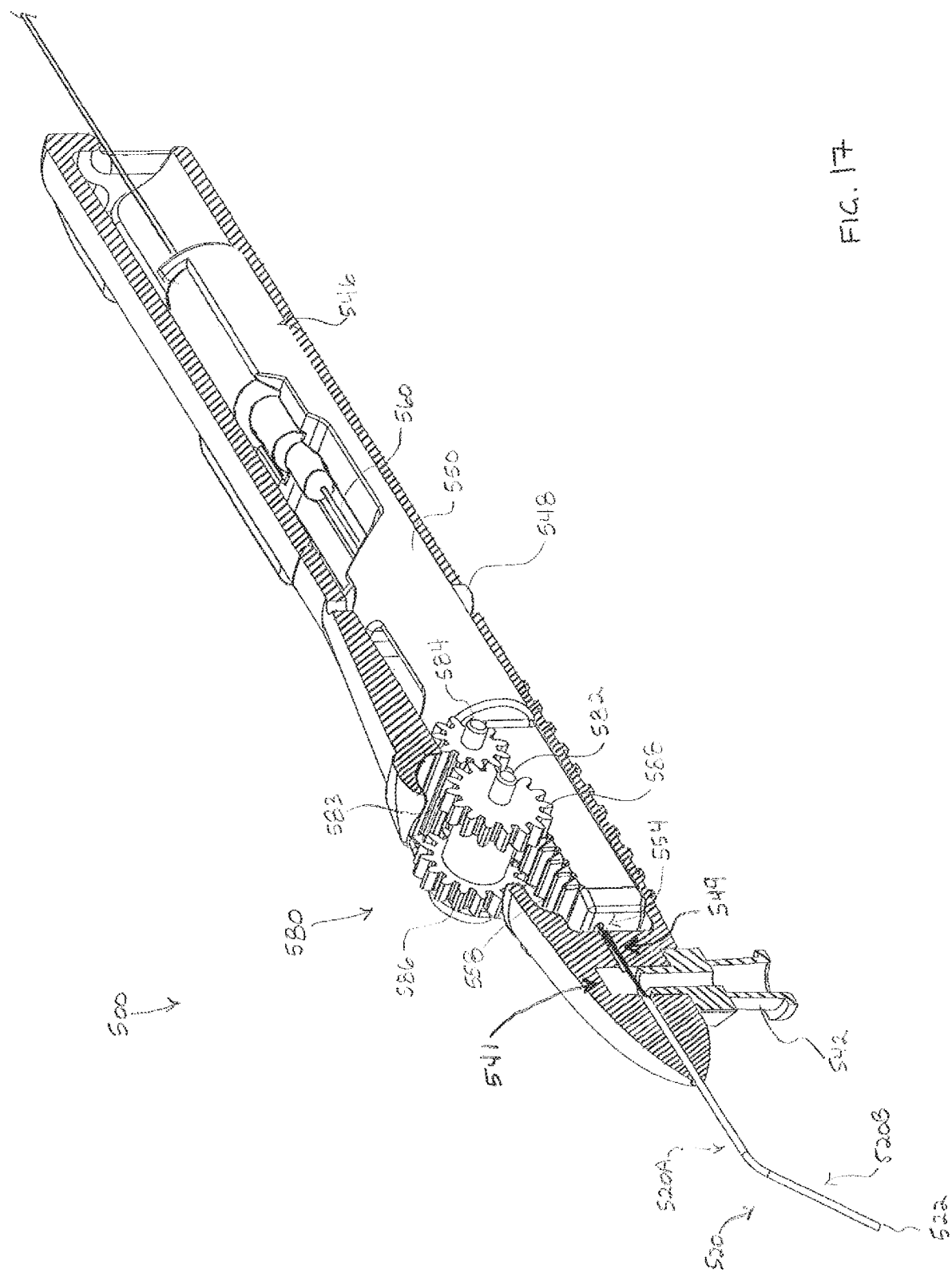

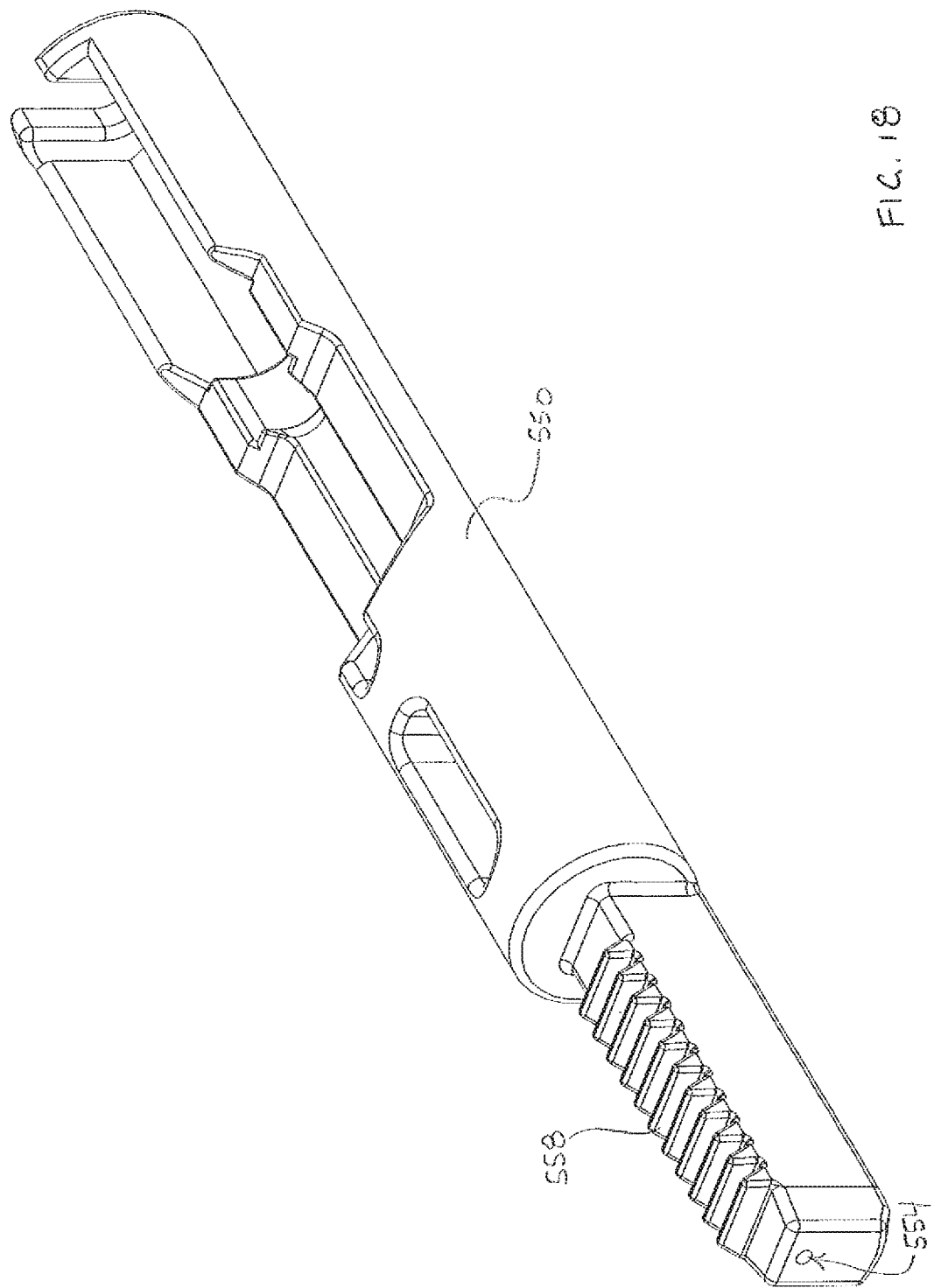

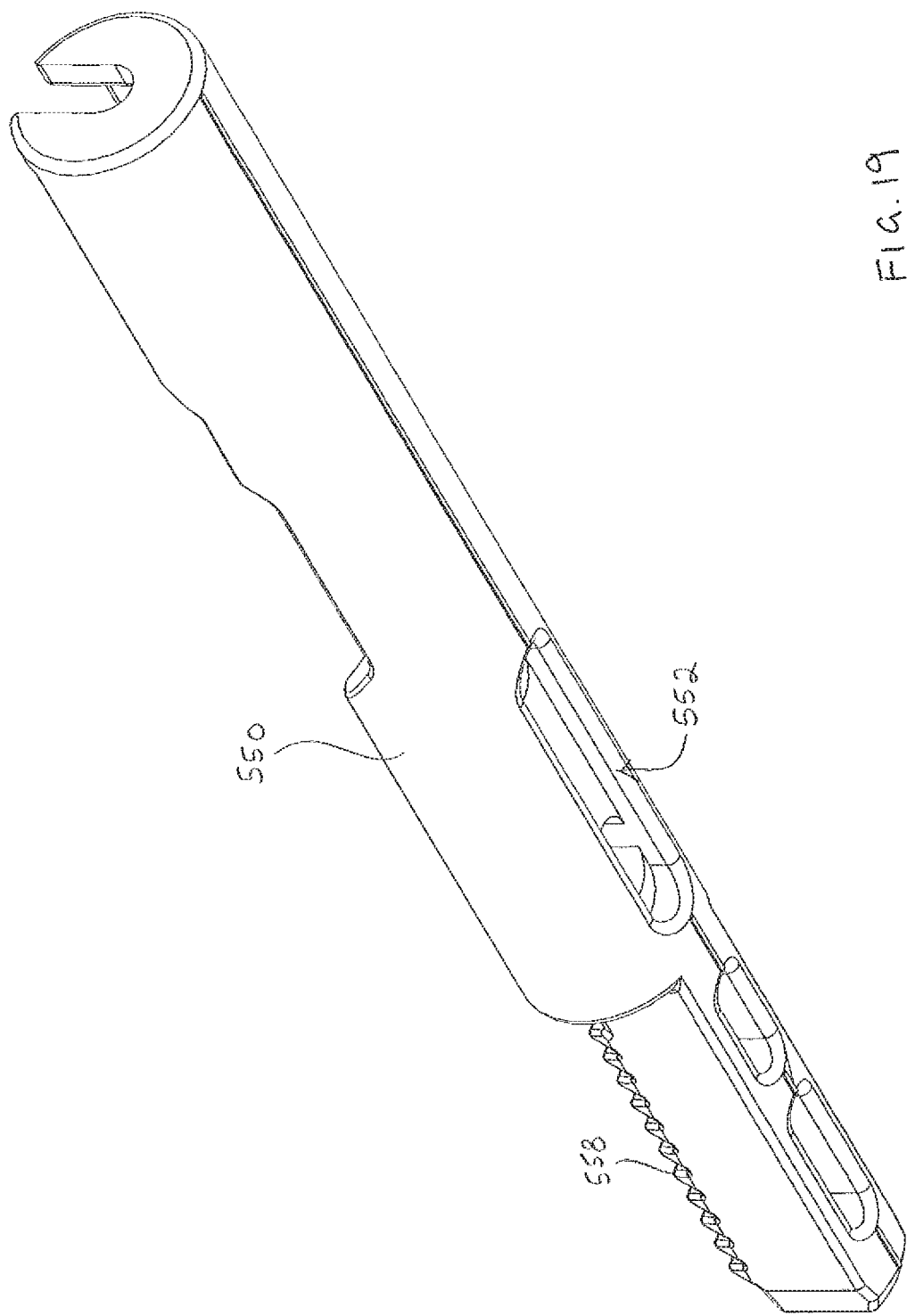

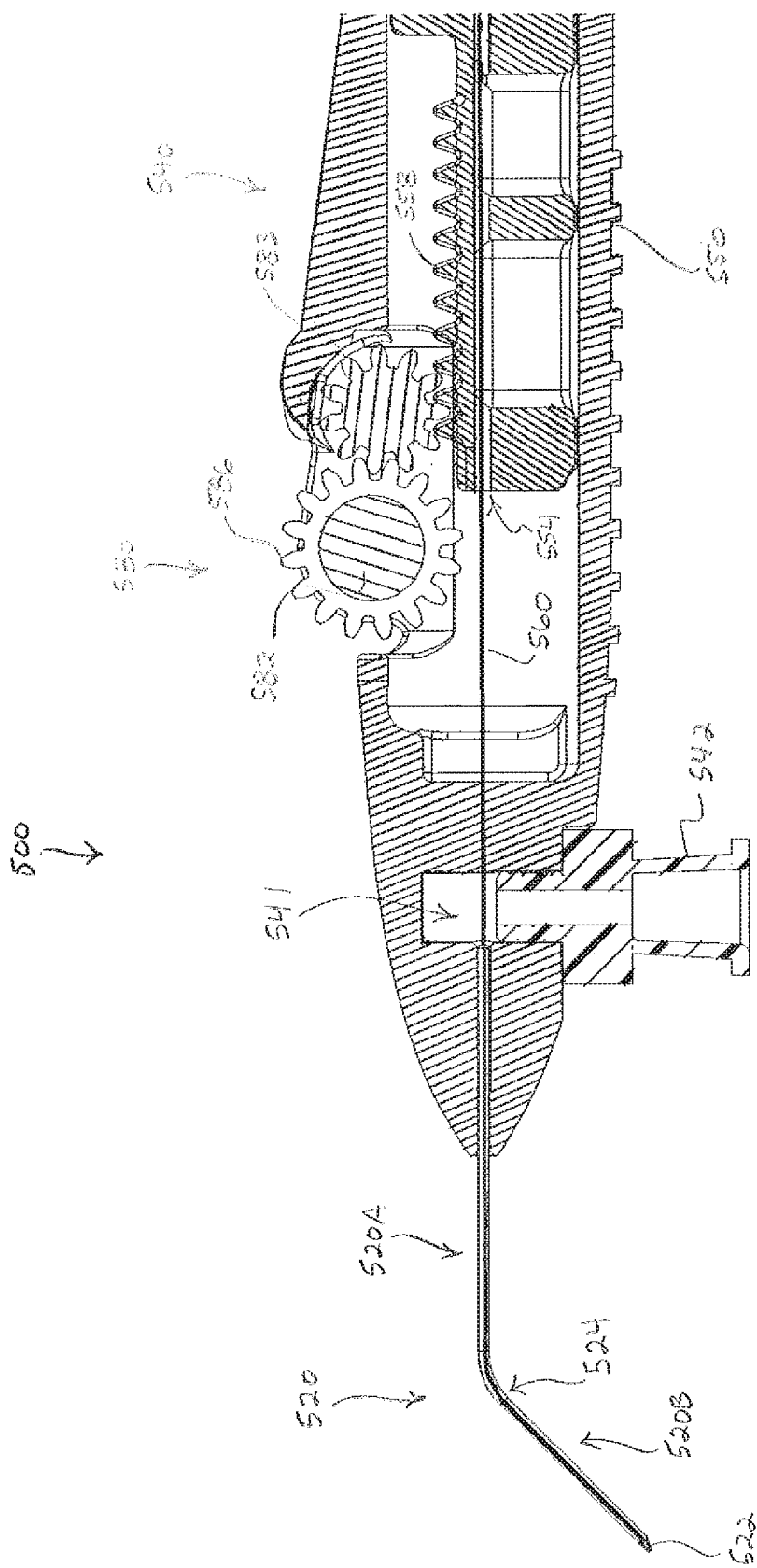

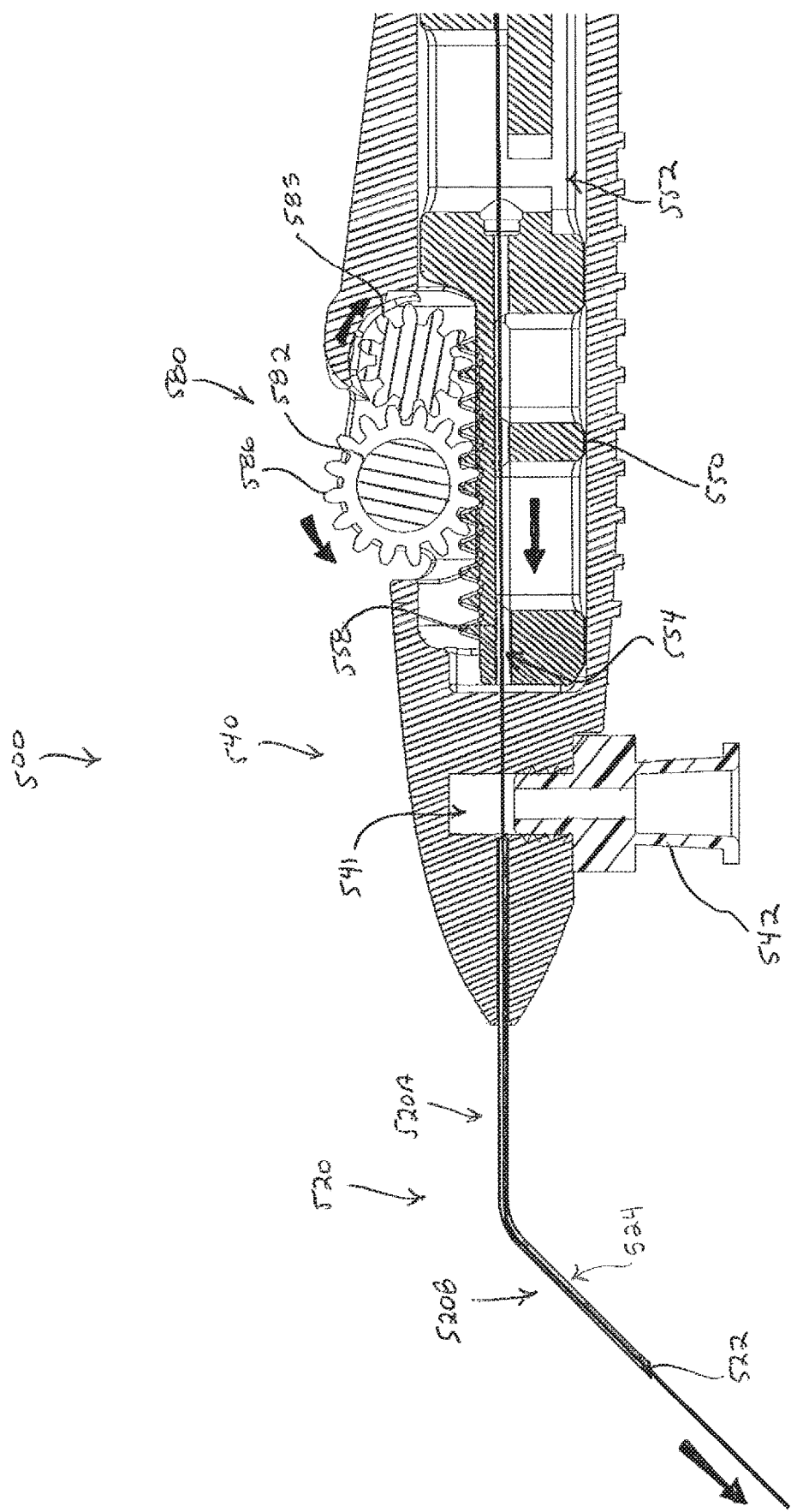

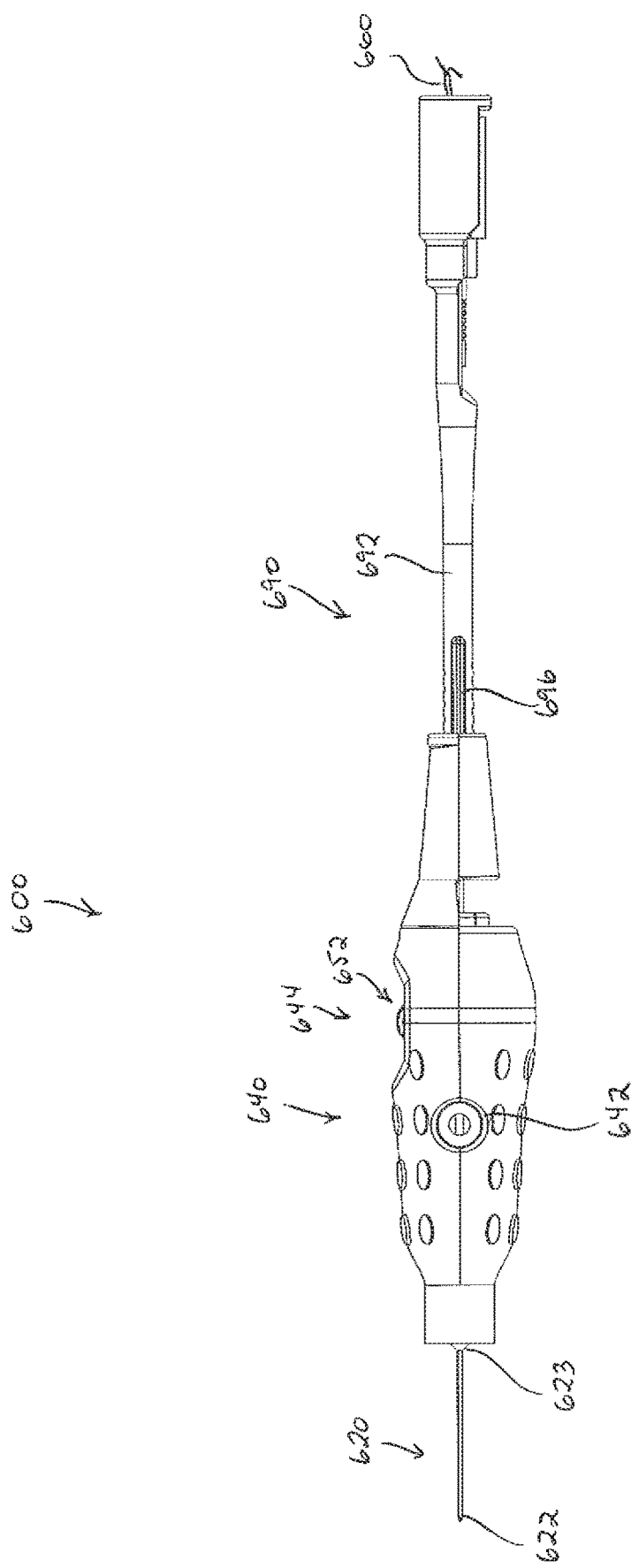

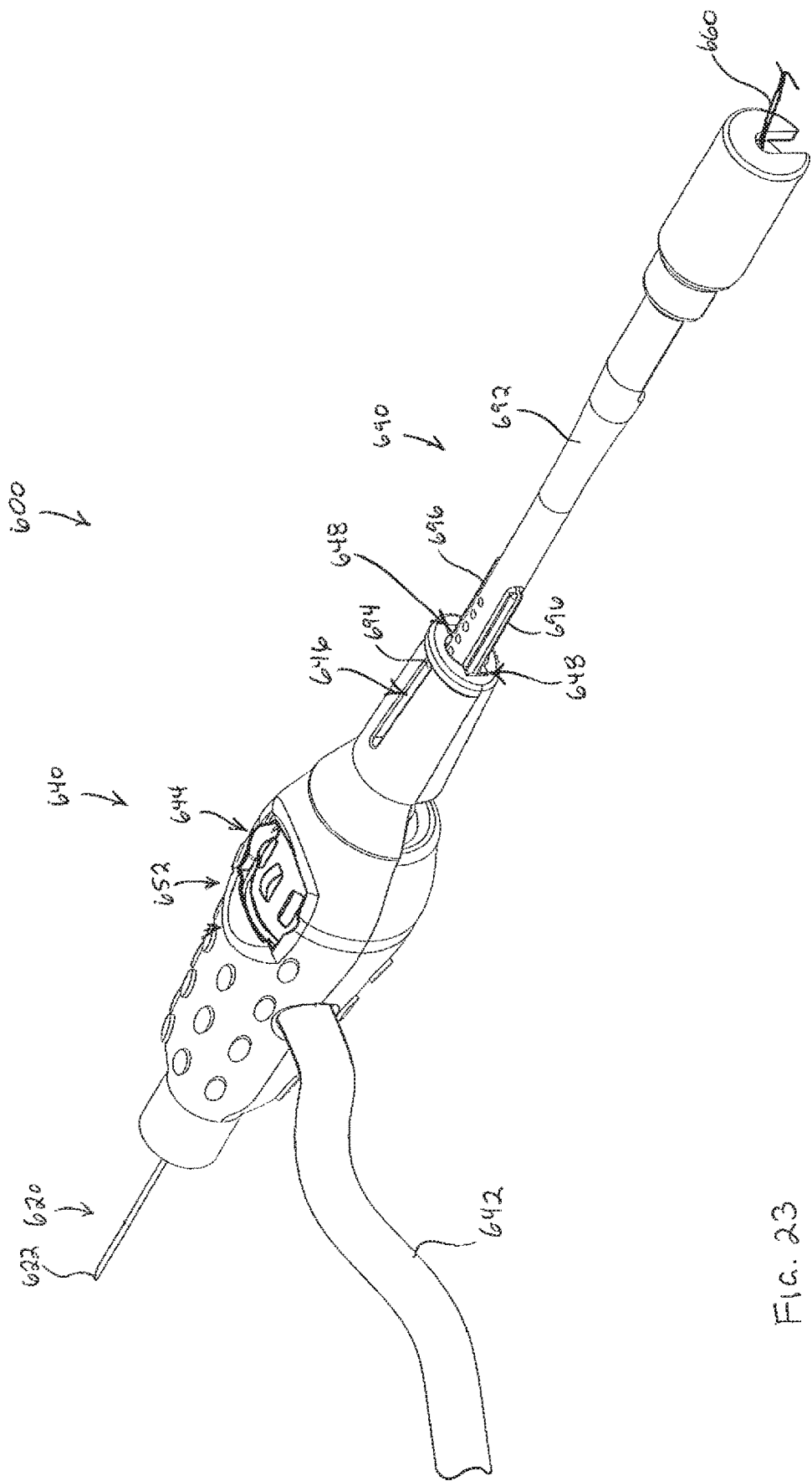

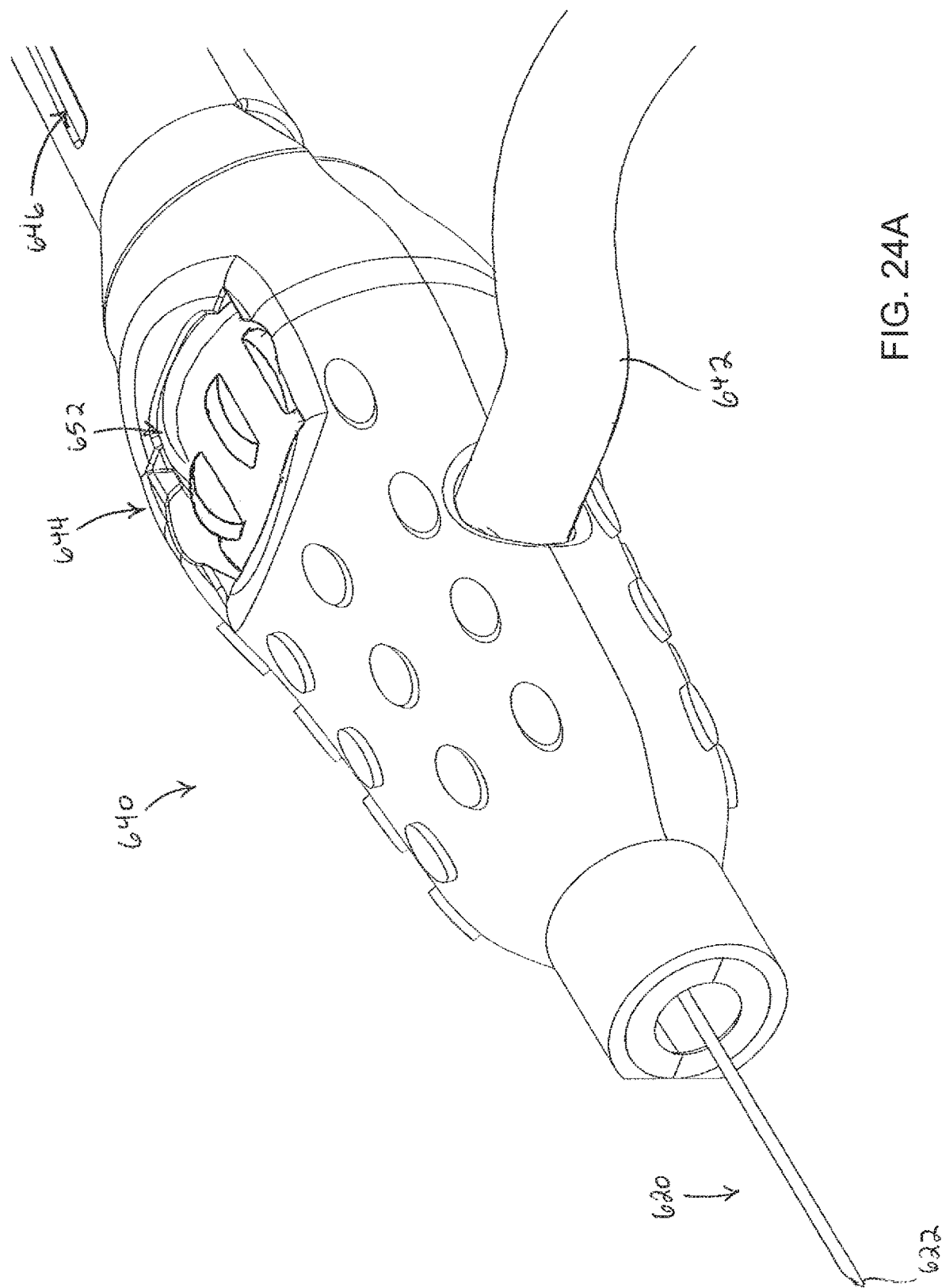

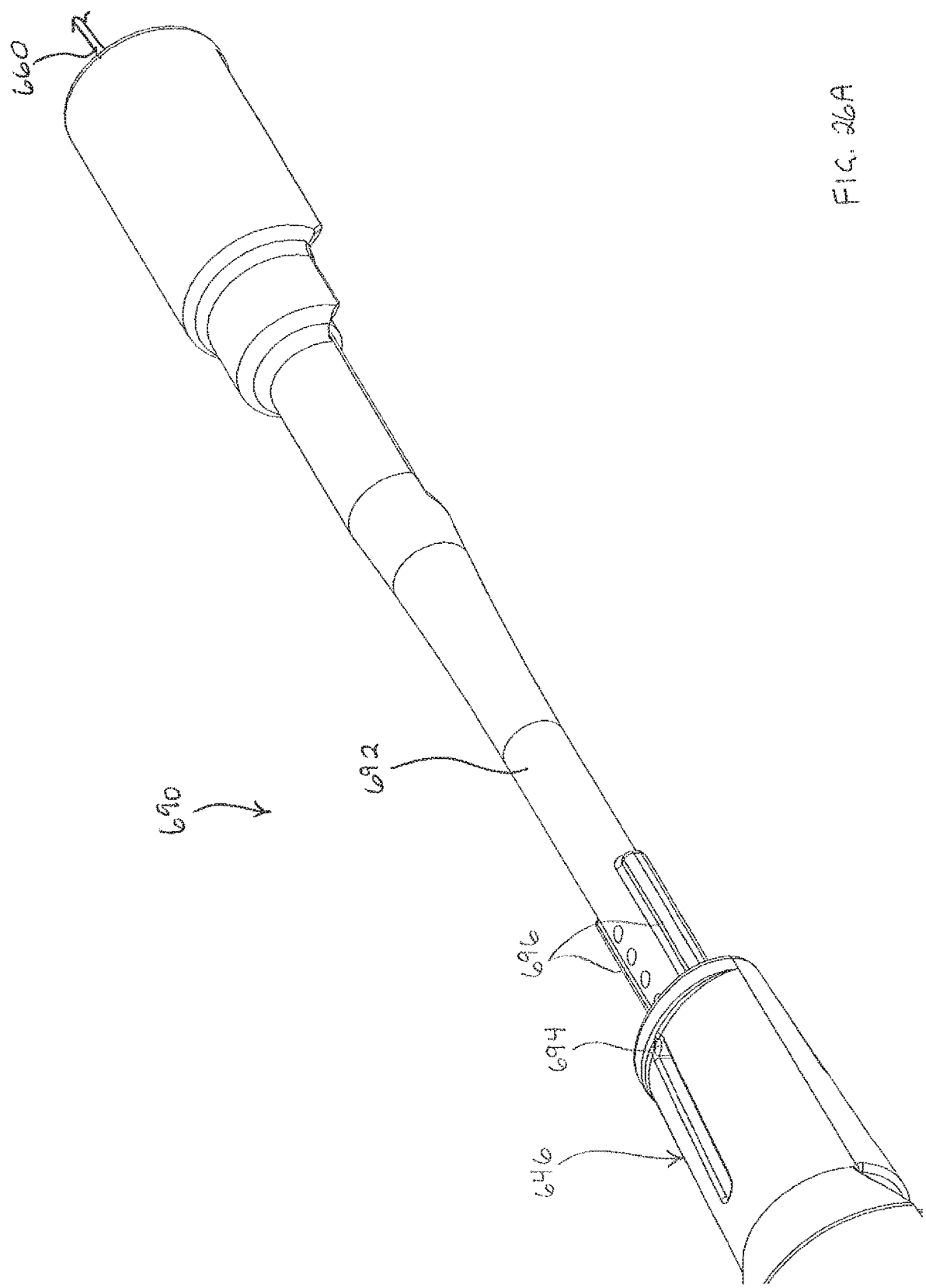

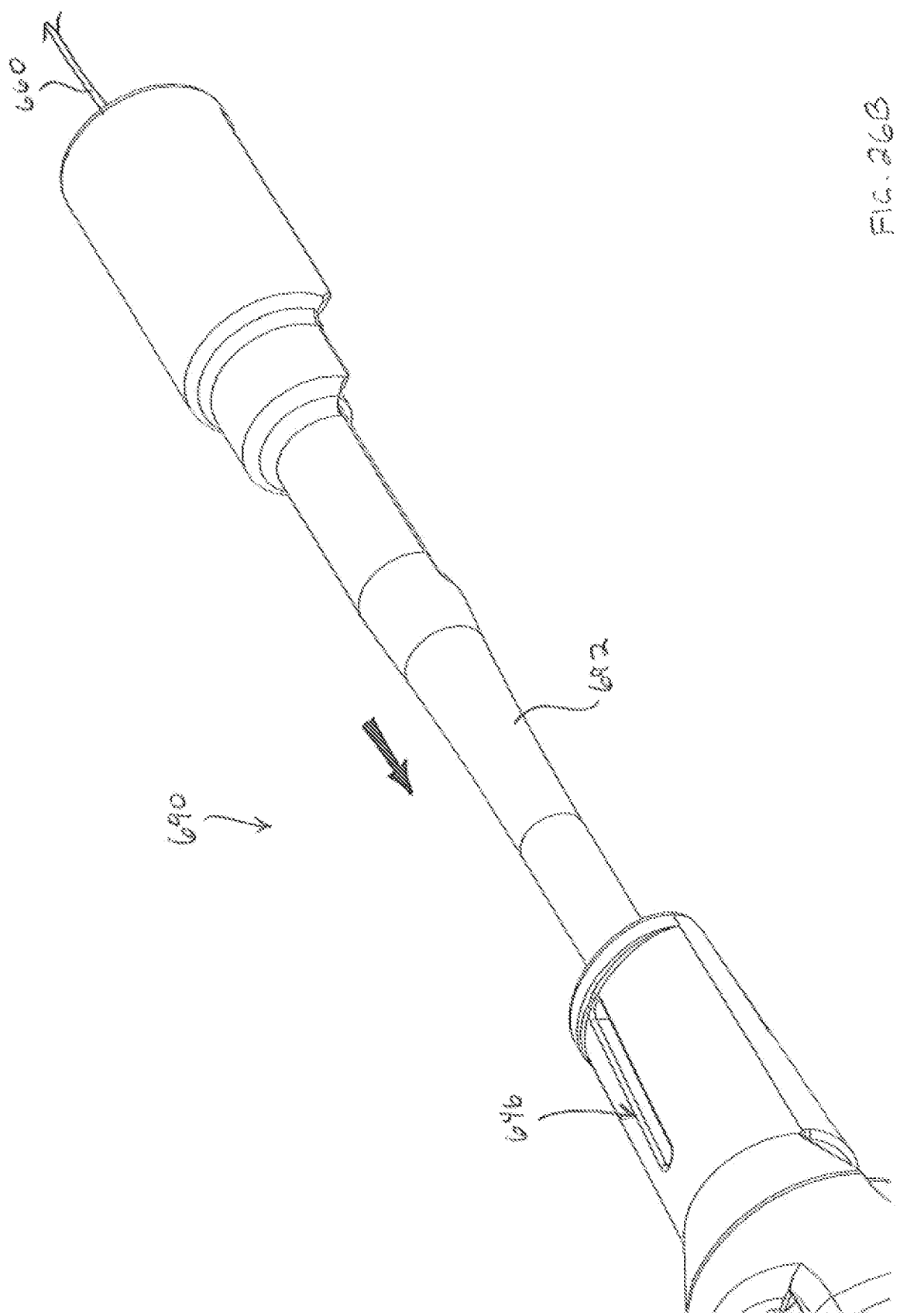

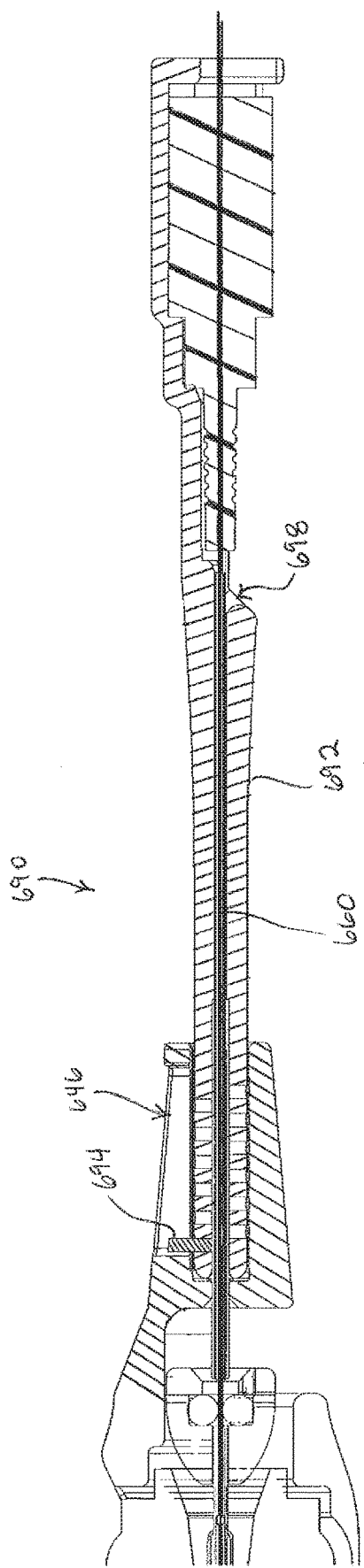

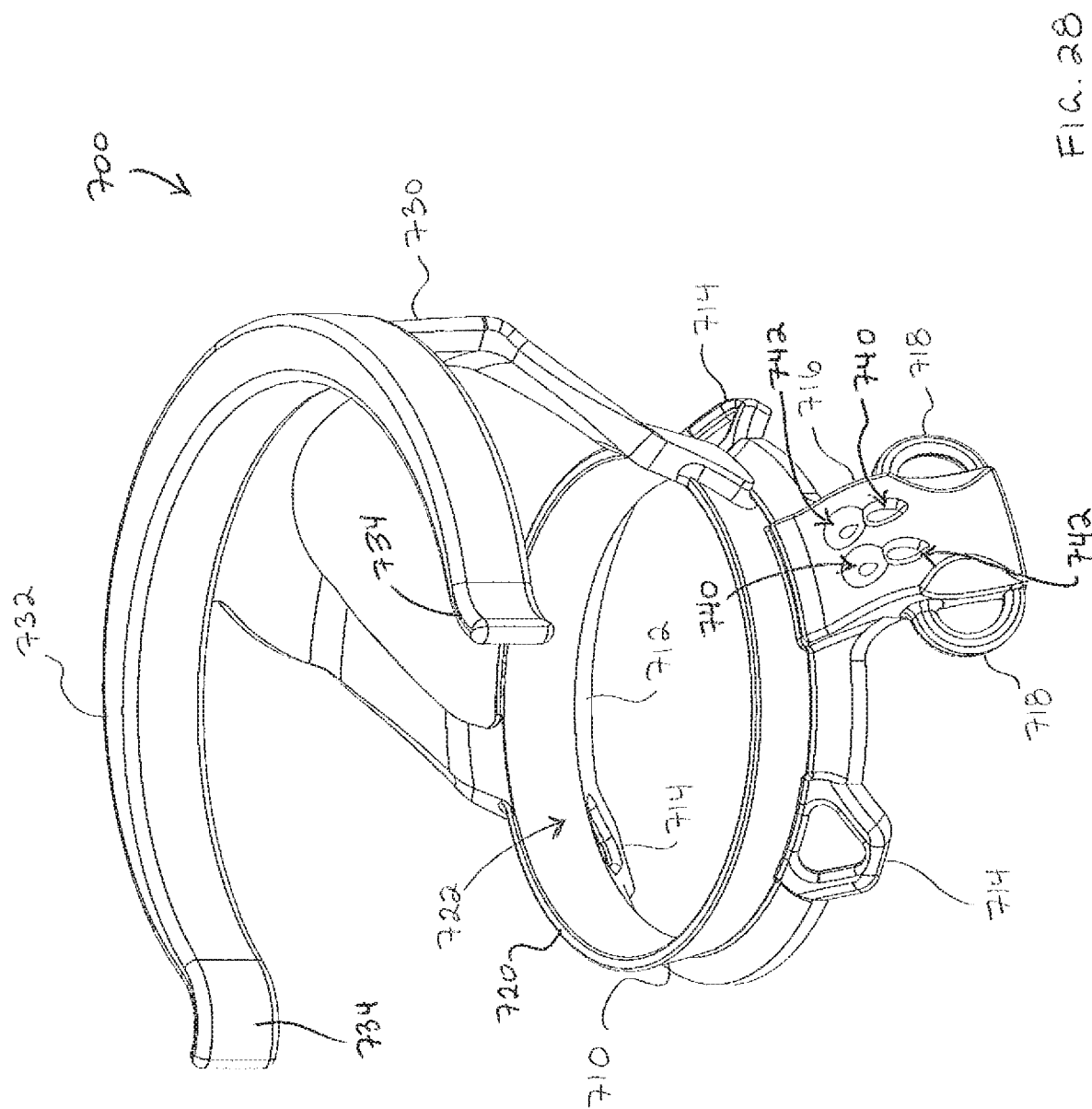

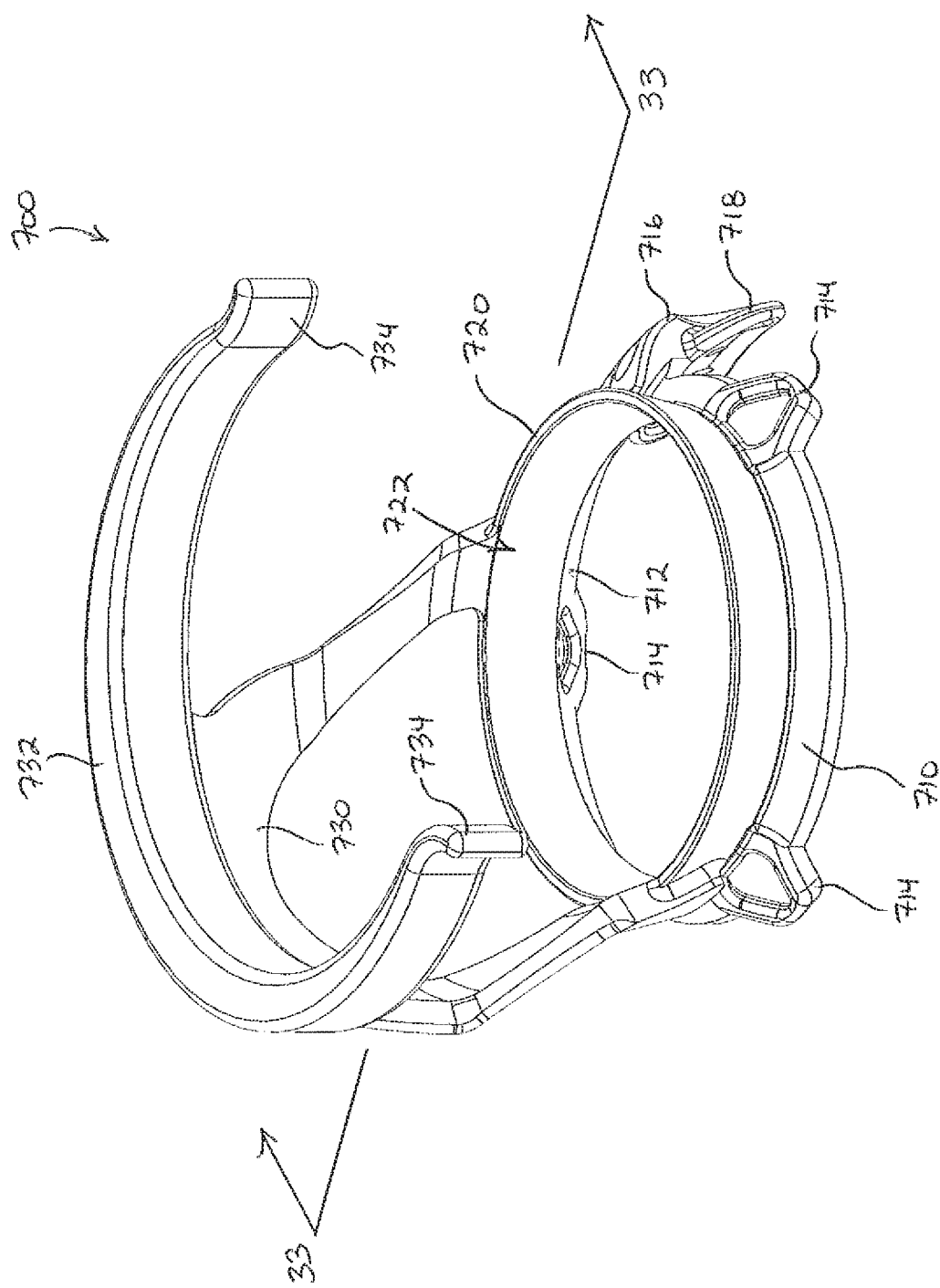

SUB-RETINAL TANGENTIAL NEEDLE CATHETER GUIDE AND INTRODUCER

PRIORITY

This application is a continuation of U.S. patent application Ser. No. 15/897,266, entitled "Sub-Retinal Tangential Needle Catheter and Introducer," filed Jun. 1, 2015, which is a continuation of U.S. patent application Ser. No. 14/726,977, entitled "Sub-Retinal Tangential Needle Catheter and Introducer," filed Jun. 1, 2015 and issued as U.S. Pat. No. 9,925,088 on Mar. 27, 2018, which claims priority to U.S. Provisional Patent Application No. 62/008,756, entitled "Sub-Retinal Tangential Needle Catheter Guide with Introducer Mechanism, and Method of Using for Delivery of Bioactive Agents," filed Jun. 6, 2014, the disclosure of which is incorporated by reference herein

JOINT RESEARCH STATEMENT

Subject matter disclosed in this application was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties to the joint research agreement include Ethicon Endo-Surgery, Inc. and Janssen Research & Development, LLC.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and in some cases may disappear as well. It may therefore be desirable to provide treatment for macular degeneration in order to prevent or reverse the loss of vision caused by macular degeneration. In some cases it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9A depicts a top plan view of an eye of a patient, with surrounding structures of the eye immobilized and a chandelier installed;

FIG. 16 depicts a partially exploded perspective view of the instrument of FIG. 13;

FIG. 17 depicts a partial cross-sectional perspective view of the instrument of FIG. 13 taken along line 17-17 of FIG. 13;

FIG. 18 depicts a perspective view of a sled of the instrument of FIG. 13;

FIG. 19 depicts another perspective view of the sled of FIG. 18;

FIG. 20A depicts a cross-sectional side view of the instrument of FIG. 13 taken along line 17-17 of FIG. 13, with the sled of FIG. 18 in a proximal longitudinal position;

FIG. 20B depicts a cross-sectional side view of the instrument of FIG. 13 taken along line 17-17 of FIG. 13, with the sled of FIG. 18 moved to a distal longitudinal position;

FIG. 22 depicts a side elevational view of the instrument of FIG. 21;

FIG. 23 depicts another perspective view of the instrument of FIG. 21;

FIG. 24A depicts a detailed perspective view of the instrument of FIG. 21, with a micro-catheter of the instrument retracted to a proximal longitudinal position in a needle of the instrument;

FIG. 26A depicts a detailed perspective view of the instrument of FIG. 21, with a catheter actuator of the instrument in a proximal longitudinal position;

FIG. 26B depicts a detailed perspective view of the instrument of FIG. 21, with the catheter actuator of FIG. 26A moved to a distal longitudinal position;

FIG. 27B depicts a detailed cross-sectional side view of the instrument of FIG. 21, with the catheter actuator of FIG. 26A moved to the distal longitudinal position of FIG. 26B;

FIG. 28 depicts a perspective view of an exemplary needle guidance device;

FIG. 29 depicts another perspective view of the guidance device of FIG. 28;

Figure 1:
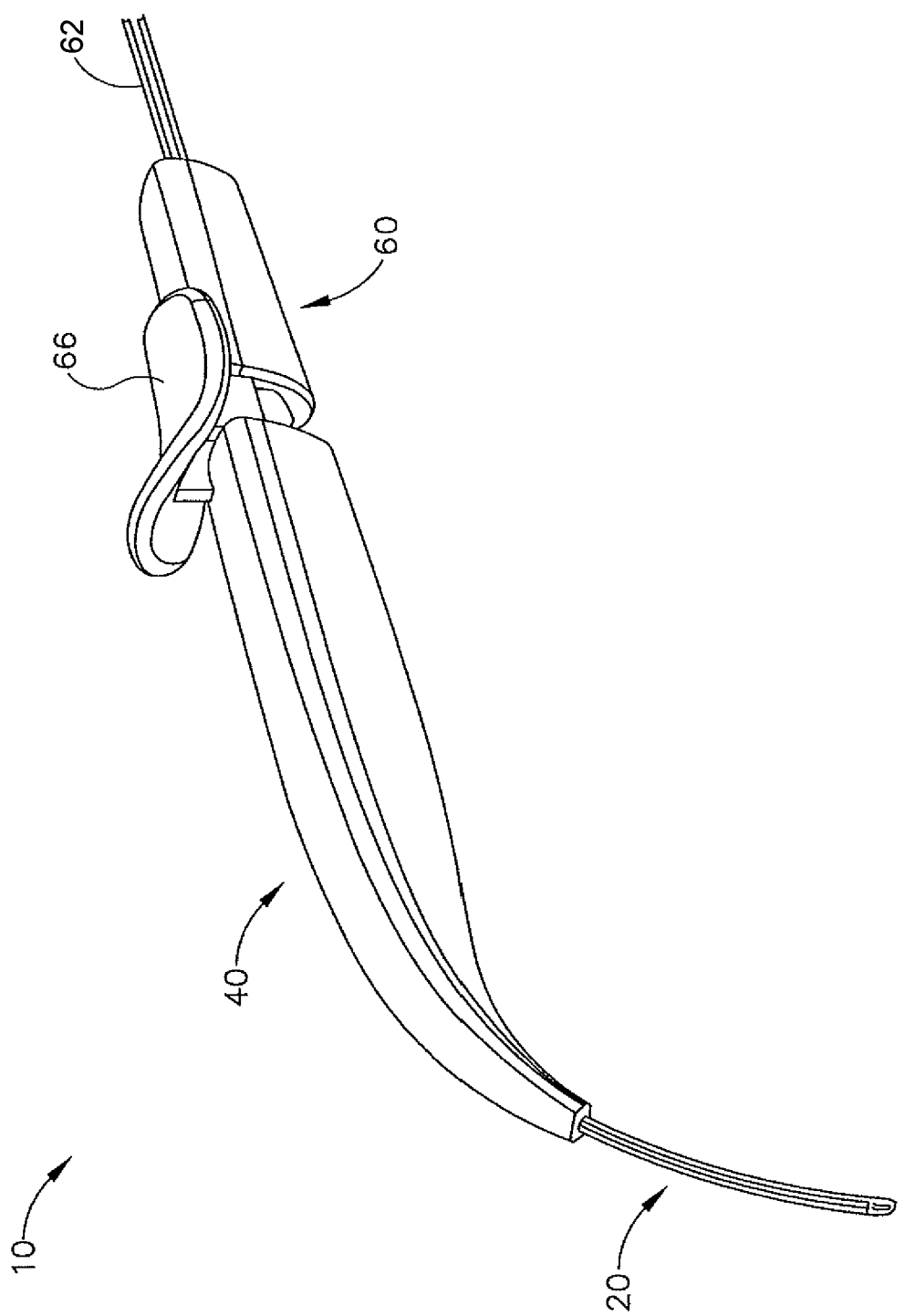
FIG. 1 depicts a perspective view of an exemplary instrument for subretinal administration of a therapeutic agent from a suprachoroidal approach.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. EXEMPLARY INSTRUMENT WITH SLIDER ARTICULATION FEATURE

FIGS. 1-4 show an exemplary instrument (10) that is configured for use in a procedure for the subretinal administration of a therapeutic agent to an eye of a patient from a suprachoroidal approach. Instrument (10) comprises a flexible cannula (20), a body (40), and a slidable (60). Cannula (20) extends distally from body (40) and has a generally rectangular cross section. Cannula (20) is generally configured to support a needle (30) that is slidable within cannula (20), as will be described in greater detail below.

In the present example, cannula (20) comprises a flexible material such as Polyether block amide (PEBA), which may be manufactured under the trade name PEBAX. Of course, any other suitable material or combination of materials may be used. Also in the present example, cannula (20) has a cross-sectional profile dimension of approximately 2.0 mm by 0.8 mm, with a length of approximately 80 mm. Alternatively, any other suitable dimensions may be used.

As will be described in greater detail below, cannula (20) is flexible enough to conform to specific structures and contours of the patient's eye, yet cannula (20) has sufficient column strength to permit advancement of cannula (20) between the sclera and choroid of patient's eye without buckling. Several factors may contribute to suitable flexibility of cannula (20). For instance, the durometer of the material used to construct cannula (20) at least partially characterizes the flexibility of cannula (20). By way of example only, the material that is used to form cannula (20) may have a shore hardness of approximately 27 D, approximately 33 D, approximately 42 D, approximately 46 D, or any other suitable shore hardness. It should be understood that the shore hardness may fall within the range of approximately 27 D to approximately 46 D; or more particularly within the range of approximately 33 D to approximately 46 D; or more particularly within the range of approximately 40 D to approximately 45 D. The particular cross-sectional shape of cannula (20) may also at least partially characterize the flexibility of cannula (20). Additionally, the stiffness of needle (30) disposed within cannula (20) may at least partially characterize the flexibility of cannula (20).

In the present example, the flexibility of cannula (20) may be quantified by calculating a bending stiffness for cannula (20). Bending stiffness is calculated by the product of the elastic modulus and the area moment of inertia. By way of example only, one exemplary material that may be used to form cannula (20) may have a shore hardness of D27, an elastic modulus (E) of $1.2\times10^7$ N/m$^2$, and an area moment of inertia ($I_x$) of $5.52\times10^{-14}$ m$^4$, providing a calculated bending stiffness about the x-axis at $0.7\times10^{-6}$ Nm$^2$. Another exemplary material that may be used to form cannula (20) may have a shore hardness of D33, an elastic modulus (E) of $2.1\times10^7$ N/m$^2$, and an area moment of inertia ($I_x$) of $5.52\times10^{-14}$ m$^4$, providing a calculated bending stiffness about the x-axis at $1.2\times10^{-6}$ Nm$^2$. Another exemplary material that may be used to form cannula (20) may have a shore hardness of D42, an elastic modulus (E) of $7.7\times10^7$ N/m$^2$, and an area moment of inertia ($I_x$) of $5.52\times10^{-14}$ m$^4$, providing a calculated bending stiffness about the x-axis at $4.3\times10^{-6}$ Nm$^2$. Another exemplary material that may be used to form cannula (20) may have a shore hardness of D46, an elastic modulus (E) of $17.0\times10^7$ N/m$^2$, and an area moment of inertia ($I_x$) of $5.52\times10^{-14}$ m$^4$, providing a calculated bending stiffness about the x-axis at $9.4\times10^{-6}$ Nm$^2$. Thus, by way of example only, the bending stiffness of cannula (20) may fall within the range of approximately $0.7\times10^{-6}$ Nm$^2$ to approximately $9.4\times10^{-6}$ Nm$^2$; or more particularly within the range of approximately $1.2\times10^{-6}$ Nm$^2$ to approximately $9.4\times10^{-6}$ Nm$^2$; or more particularly within the range of approximately $2.0\times10^{-6}$ Nm$^2$ to approximately $7.5\times10^{-6}$ Nm$^2$; or more particularly within the range of approximately $2.0\times10^{-6}$ Nm$^2$ to approximately $6.0\times10^{-6}$ Nm$^2$; or more particularly within the range of approximately $3.0\times10^{-6}$ Nm$^2$ to approximately $5.0\times10^{-6}$ Nm$^2$; or more particularly within the range of approximately $4.0\times10^{-6}$ Nm$^2$ to approximately $5.0\times10^{-6}$ Nm$^2$.

In the present example, the flexibility of cannula (20) may also be quantified by the following formula:

$$\delta = \frac{FL^3}{48EI} \tag{1}$$

In the above equation, bending stiffness (EI) is calculated experimentally by deflecting cannula (20) having a fixed span (L) a set distance to yield a predetermined amount of deflection ($\delta$). The amount of force (F) required for such a deflection may then be recorded. For instance, when using such a method cannula (20) may have a span of 0.06 m and may be deflected for a given distance. By way of example only, one exemplary material that may be used to form cannula (20) may require a force of 0.0188 N to achieve a deflection of 0.0155 m, providing a calculated bending stiffness about the x-axis of $5.5\times10^{-6}$ Nm$^2$. In another exemplary material that may be used to form cannula (20) may require a force of 0.0205 N to achieve a deflection of 0.0135 m, providing a calculated bending stiffness about the x-axis of $6.8\times10^{-6}$ Nm$^2$. In still another exemplary material that may be used to form cannula (20) may require a force of 0.0199 N to achieve a deflection of 0.0099 m, providing a calculated bending stiffness about the x-axis of $9.1\times10^{-6}$ Nm$^2$. In yet another exemplary material that may be used to form cannula (20) may require a force of 0.0241 N to achieve a deflection of 0.0061 m, providing a calculated bending stiffness about the x-axis of $1.8\times10^{-6}$ Nm$^2$. In yet another exemplary material that may be used to form cannula (20) may require a force of 0.0190 N to achieve a deflection 0.0081 m, providing a calculated bending stiffness about the x-axis of $1.0\times10^{-6}$ Nm$^2$. In yet another exemplary material that may be used to form cannula (20) may require a force of 0.0215 N to achieve a deflection of 0.0114 m, providing a calculated bending stiffness about the x-axis of $8.4\times10^{-6}$ Nm$^2$. In yet another exemplary material that may be used to form cannula (20) may require a force of 0.0193 N to achieve a deflection of 0.0170 m, providing a calculated bending stiffness about the x-axis of $5.1\times10^{-6}$ Nm$^2$. In yet another exemplary material that may be used to form cannula (20) may require a force of 0.0224 N to achieve a deflection of 0.0152 m, providing a calculated bending stiffness about the x-axis of $6.6\times10^{-6}$ Nm$^2$. In yet another exemplary material that may be used to form cannula (20) may require a force of 0.0183 N to achieve a deflection of 0.0119 m, providing a calculated bending stiffness about the x-axis of $6.9\times10^{-6}$ Nm$^2$. In yet another exemplary material that may be used to form cannula (20) may require a force of 0.0233 N to achieve a deflection of 0.0147 m, providing a calculated bending stiffness about the x-axis of $7.1\times10^{-6}$ Nm$^2$. In yet another exemplary material that may be used to form cannula (20) may require a force of 0.0192 N to achieve a deflection of 0.0122, providing a calculated bending stiffness about the x-axis of $7.1\times10^{-6}$ Nm$^2$. In yet another exemplary material that may be used to form cannula (20) may require a force of 0.0201 N to achieve a deflection of 0.0201, providing a calculated bending stiffness about the x-axis of $4.5\times10^{-6}$ Nm$^2$. Thus, by way of example only, the bending stiffness of cannula (20) may fall within the range of approximately $1.0\times10^{-6}$ Nm$^2$ to approximately $9.1\times10^{-6}$ Nm$^2$. It should be understood that in other examples, the bending stiffness of cannula may fall within the range of approximately $0.7\times10^{-6}$ Nm$^2$ to approximately $11.1\times10^{-6}$ Nm$^2$; or more particularly within the range of approximately $2.0\times10^{-6}$ Nm$^2$ to approximately $6.0\times10^{-6}$ Nm$^2$.

Needle (30) may have a bending stiffness that differs from the bending stiffness of cannula (20). By way of example only, needle (30) may be formed of a nitinol material that has an elastic modulus (E) of $7.9\times10^{10}$ N/m$^2$, and an area moment of inertia ($I_x$) of $2.12\times10^{-7}$ m$^4$, providing a calculated bending stiffness about the x-axis at $1.7\times10^{-6}$ Nm$^2$. By way of further example only, the bending stiffness of needle (30) may fall within the range of approximately $0.5\times10^{-6}$ Nm$^2$ to approximately $2.5\times10^{-6}$ Nm$^2$; or more particularly within the range of approximately $0.75\times10^{-6}$ Nm$^2$ to approximately $2.0\times10^{-6}$ Nm$^2$; or more particularly within the range of approximately $1.25\times10^{-6}$ Nm$^2$ to approximately $1.75\times10^{-6}$ Nm$^2$.

Figure 5:
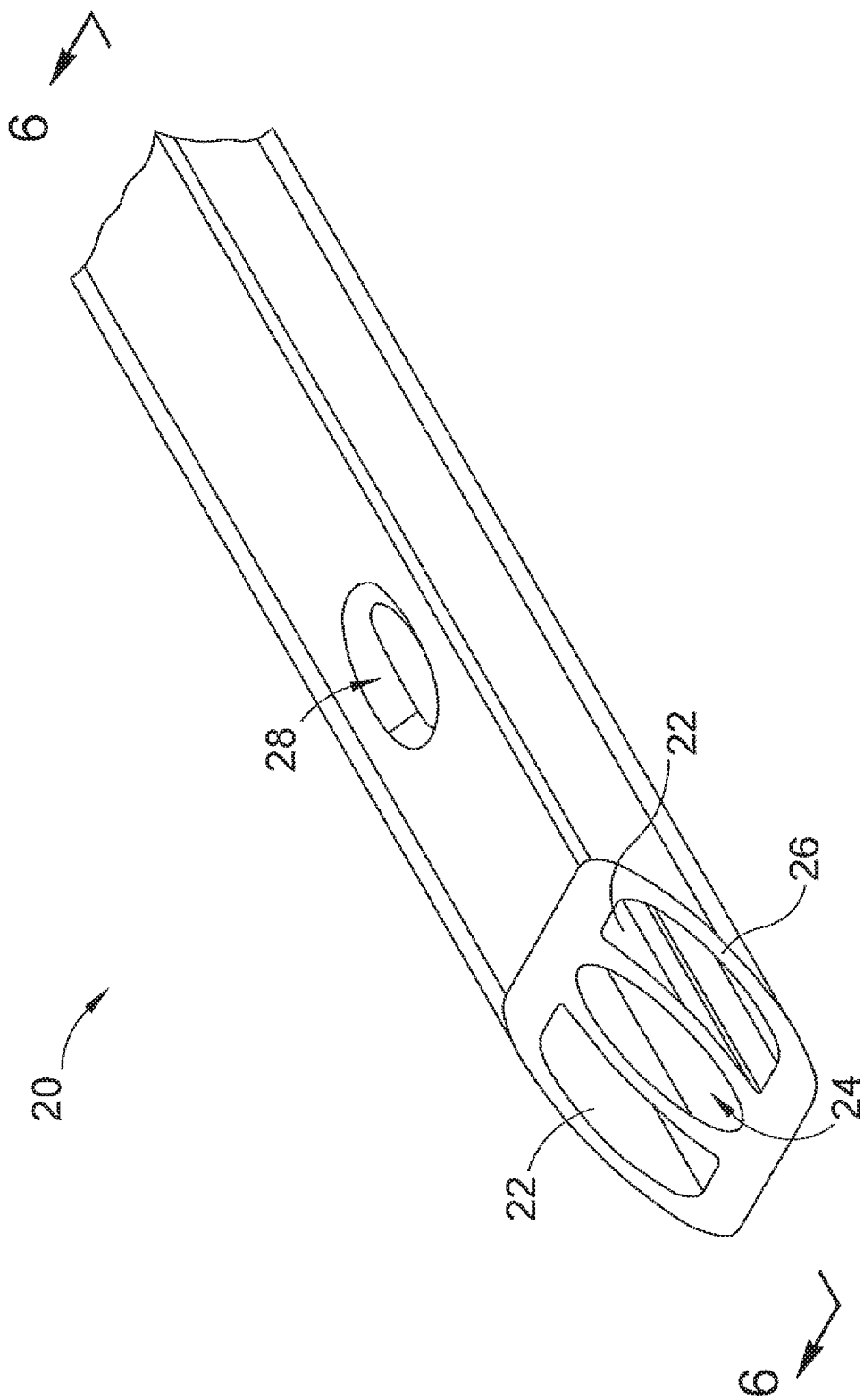
FIG. 5 depicts a perspective view of the distal end of an exemplary cannula that may be incorporated into the instrument of FIG. 1.
Figure 6:
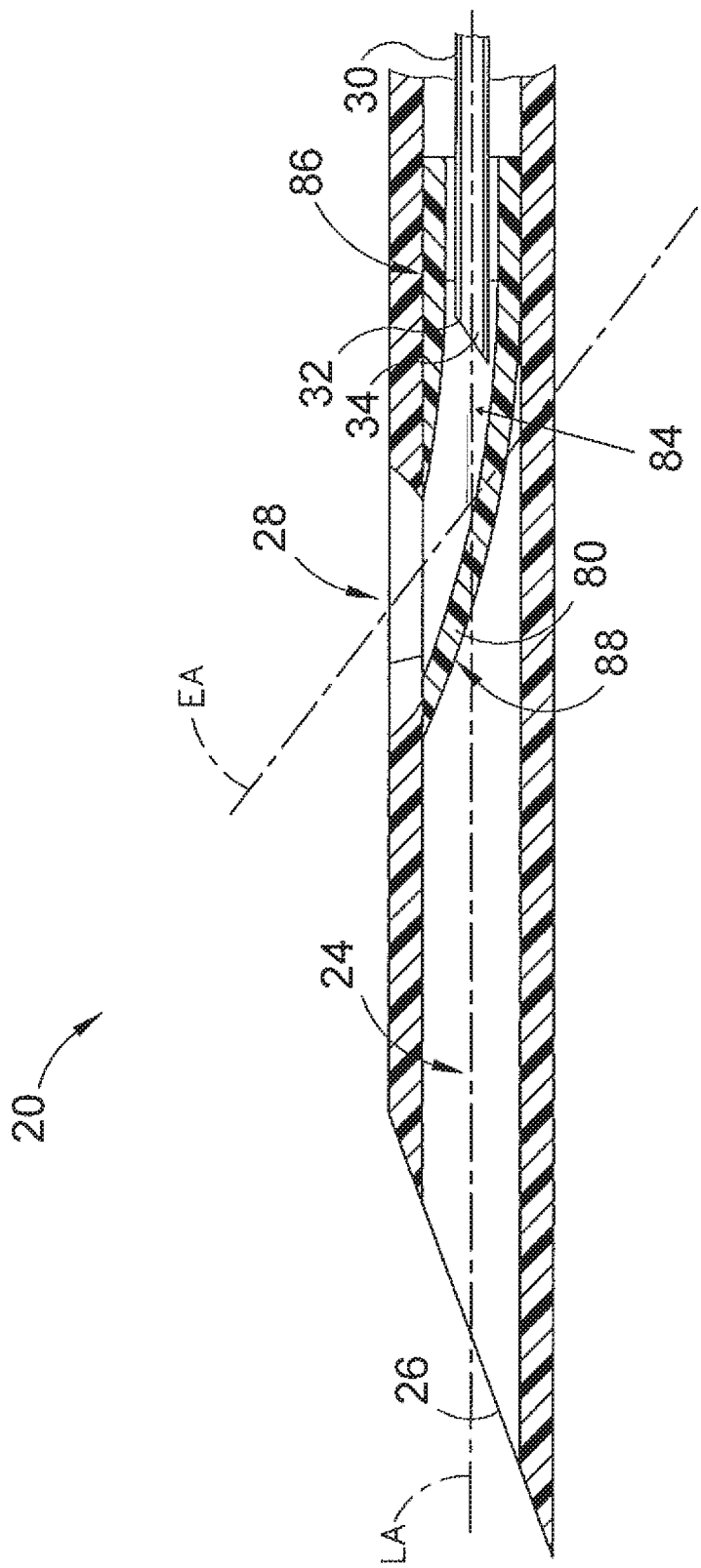
FIG. 6 depicts a cross-sectional view of the cannula of FIG. 5, with the cross-section taken along line 6-6 of FIG. 5.

As can be seen in FIGS. 5 and 6, cannula (20) comprises two side lumens (22) and a single central lumen (24) extending longitudinally through cannula (20) and terminating at an atraumatic, beveled distal end (26). A beveled lateral opening (28) is located proximal to beveled distal end (26). Side lumens (22) contribute to the flexibility of cannula (20). Although lumens (22, 24) are shown as being open at beveled distal end (26), it should be understood that in some examples, side lumens (22, 24) may be optionally closed at beveled distal end (26). As will be described in greater detail below, central lumen (24) is configured to receive needle (30) and a needle guide (80). In some versions, an optical fiber (not shown) is also disposed in central lumen (24) alongside needle (30). Such an optical fiber may be used to provide illumination and/or optical feedback.

Beveled distal end (26) is generally beveled to provide separation between the sclera and choroid layers to enable cannula (20) to be advanced between such layers while not inflicting trauma to the sclera or choroid layers. In the present example, beveled distal end (26) is beveled at an angle of approximately 15° relative to the longitudinal axis of cannula (20) in the present example. In other examples, beveled distal end (26) may have a bevel angle within the range of approximately 5° to approximately 50°; or more particularly within the range of approximately 5° to approximately 40°; or more particularly within the range of approximately 10° to approximately 30°; or more particularly within the range of approximately 10° to approximately 20°.

A needle guide (80) is disposed within lumen (24) such that the distal end of needle guide (80) abuts beveled lateral opening (28). Needle guide (80) is generally configured to direct needle (30) upwardly along an exit axis (EA) that is obliquely oriented relative to the longitudinal axis (LA) of cannula (20) through beveled opening (28) of cannula (20). Needle guide (80) may be formed of plastic, stainless steel, and/or any other suitable biocompatible material(s). The shape of needle guide (80) is configured for insertion into central lumen (24). In the present example, needle guide (80) is secured within central lumen (24) by a press or interference fit, although in other examples, adhesives and/or mechanical locking mechanisms may be used to secure needle guide (80).

As can best be seen in FIG. 6, needle guide (80) defines an internal lumen (84) that is configured to slidably receive needle (30). In particular, internal lumen (84) includes a generally straight proximal portion (86) and a curved distal portion (88). Straight proximal portion (86) corresponds to the longitudinal axis (LA) of cannula (20), while curved distal portion (88) curves upwardly away from the longitudinal axis of cannula (20). Curved distal portion (88) of the present example is curved to direct needle (30) along an exit axis (EA) that extends distally from cannula (20) at an angle of approximately 7° to approximately 9° relative to the longitudinal axis (LA) of cannula (20). It should be understood that such an angle may be desirable to deflect needle (30) in a direction to ensure penetration of needle into the choroid (306) and to minimize the possibility of needle (30) continuing beneath the choroid (306) through the suprachoroidal space (as opposed to penetrating through the choroid (306)) and the possibility of retinal perforation. By way of further example only, curved distal portion (88) may urge needle (30) to exit cannula (20) along an exit axis (EA) that is oriented at an angle within the range of approximately 5° to approximately 30° relative to the longitudinal axis (LA) of cannula (20); or more particularly within the range of approximately 5° to approximately 20° relative to the longitudinal axis (LA) of cannula (20); or more particularly within the range of approximately 5° to approximately 10° relative to the longitudinal axis (LA) of cannula (20).

Needle (30) is in the form of an inner cannula that has a sharp distal end (32) and defines an internal lumen (34). Distal end (32) of the present example has a lancet configuration. In some other versions, distal end (32) has a tri-bevel configuration or any other configuration as described in U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12, 2019, the disclosure of which is incorporated by reference herein. Still other suitable forms that distal end (32) may take will be apparent to those of ordinary skill in the art in view of the teachings herein. Needle (30) of the present example comprises a nitinol hypodermic needle that is sized to deliver the therapeutic agent while being small enough to create self sealing wounds as needle (30) penetrates tissue structures of the patient's eye, as will be described in greater detail below. By way of example only, needle (30) may be 35 gauge with a 100 µm inner diameter, although other suitable sizes may be used. For instance, the outer diameter of needle (30) may fall within the range of 27 gauge to 45 gauge; or more particularly within the range of 30 gauge to 42 gauge; or more particularly within the range of 32 gauge to 39 gauge. As another merely illustrative example, the inner diameter of needle (30) may fall within the range of approximately 50 µm to approximately 200 µm; or more particularly within the range of approximately 50 µm to approximately 150 µm; or more particularly within the range of approximately 75 µm to approximately 125 µm.

Referring back to FIGS. 1-2, body (40) is generally shaped as an elongate rectangle with a curved distal end. The particular shape of body (40) that is shown is configured to be grasped by an operator. Alternatively, body (40) may be mounted on a support device or robotic arm for ease of positioning instrument (10), as described in U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12 2019, the disclosure of which is incorporated by reference herein.

Actuation assembly (60) includes an actuation member (62) and a locking member (66). Locking member (66) is removably attachable to body engagement portion (50), between body (40) and actuation member (62). As will be described in greater detail below, locking member (66) fills a space between body (40) and actuation member (62) to prevent actuation member (62) from being advanced distally relative to body (40). However, locking member (66) can be removed to selectively permit actuation member (62) to be advanced distally relative to body (40).

Figure 2:
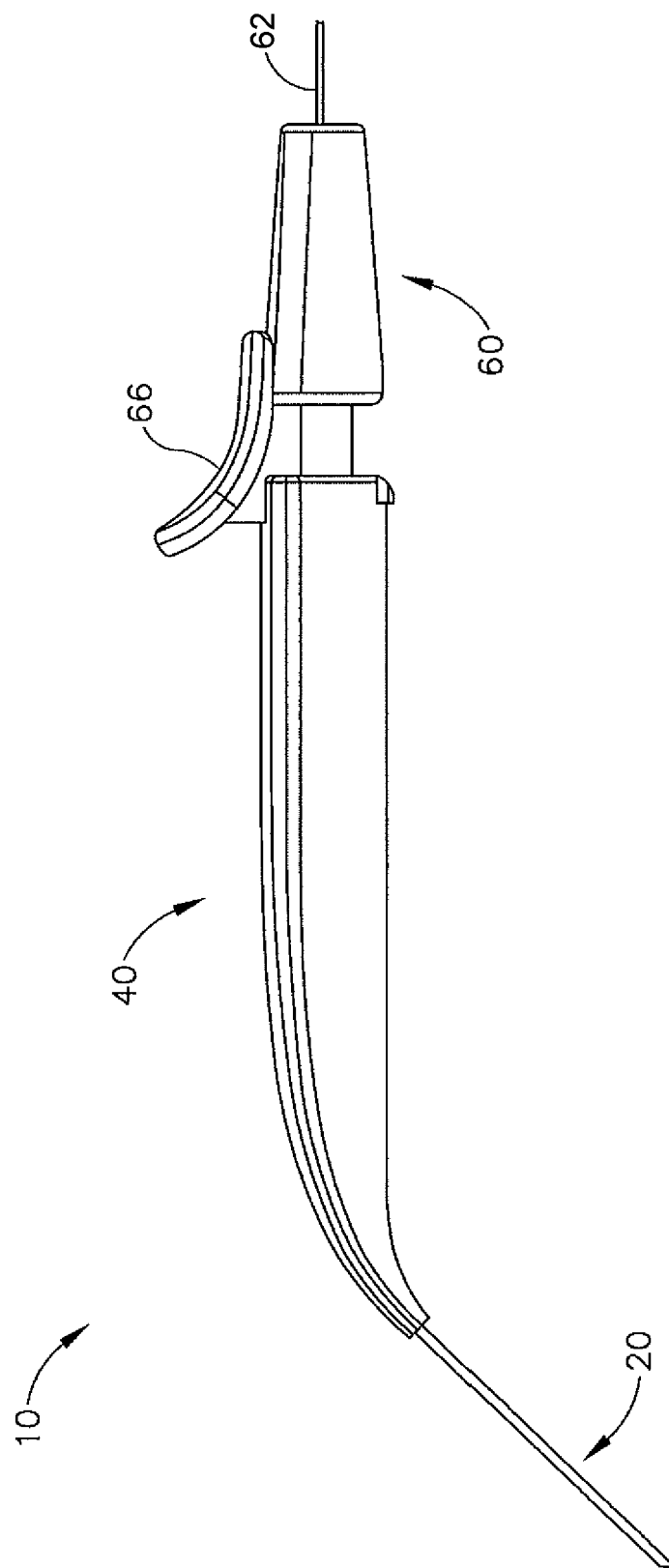
FIG. 2 depicts a side elevational view of the instrument of FIG. 1.
Figure 3:
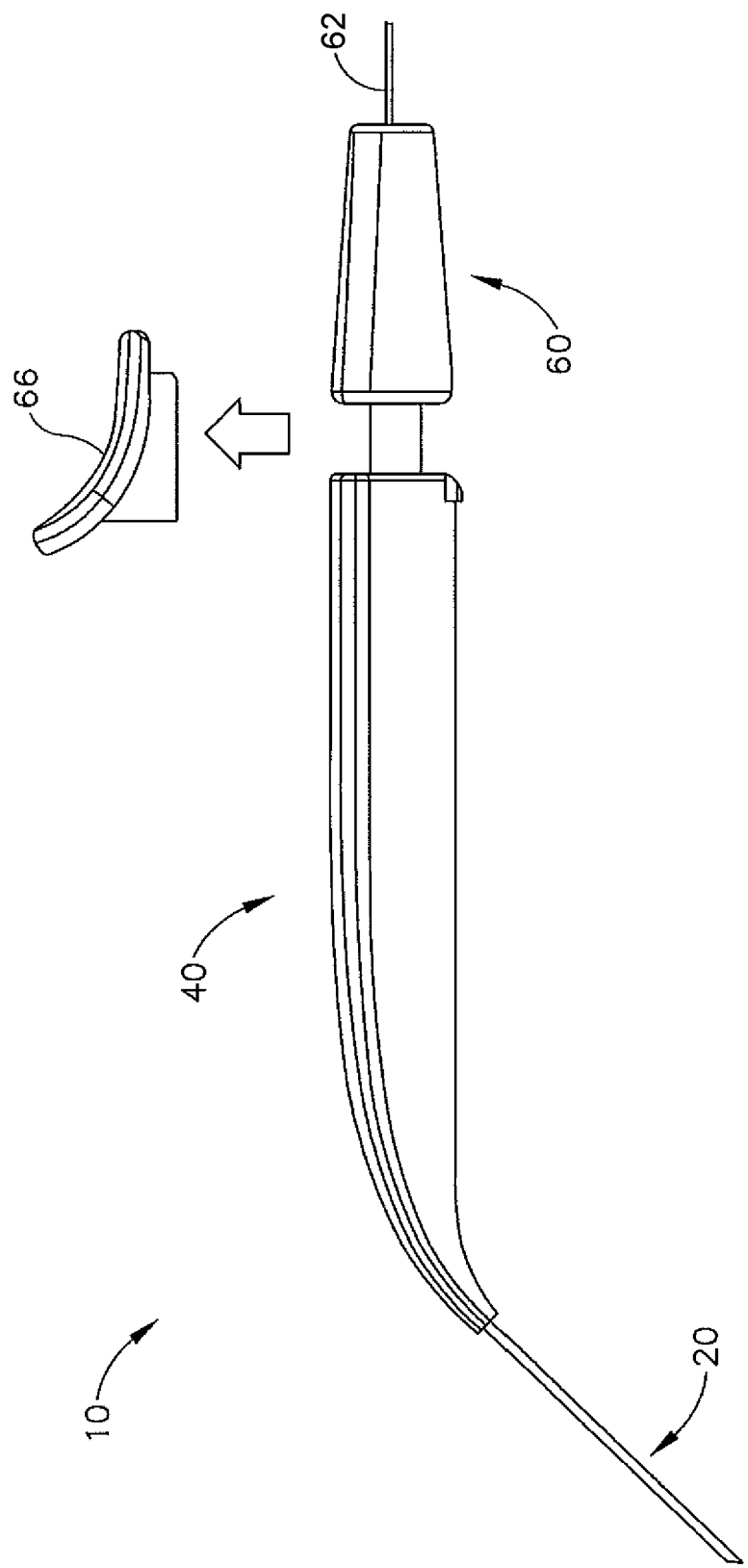
FIG. 3 depicts another side elevational view of the instrument of FIG. 1, with a locking member removed.
Figure 4:
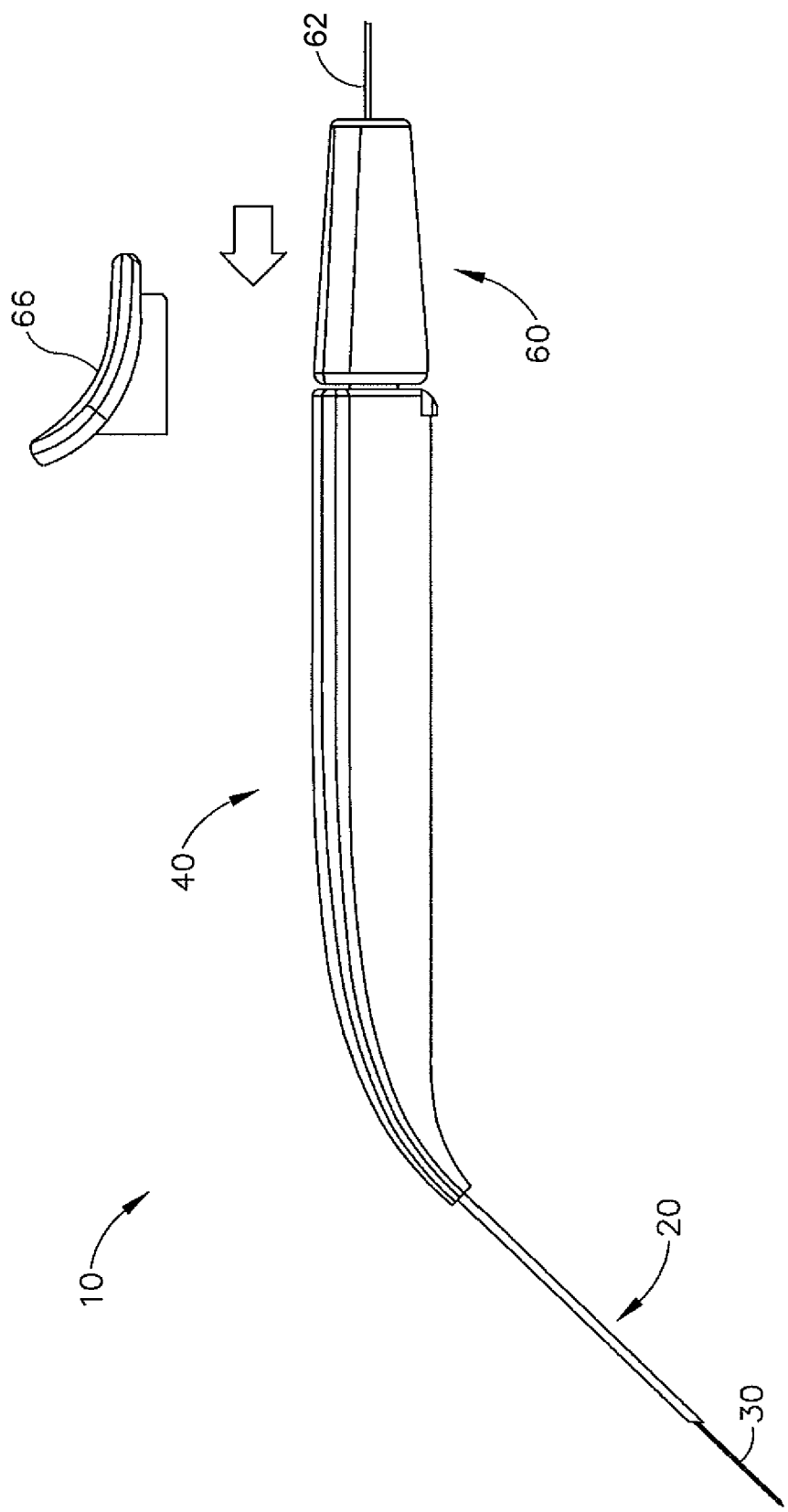
FIG. 4 depicts another side elevational view of the instrument of FIG. 1, with an actuation member advanced distally to extend the needle distally from the cannula.

FIGS. 2-4 show an exemplary actuation of instrument (10). In particular, as can be seen in FIG. 2, needle (30) is initially retracted into cannula (20) and locking member (66) is positioned between body (40) and actuation member (62), thereby preventing advancement of actuation member (62). With instrument (10) in this configuration, cannula (20) may be positioned within an eye of a patient as will be described in greater detail below.

Once cannula (20) is positioned within an eye of a patient, an operator may desire to advance needle (30) relative to cannula (20). To advance needle (30), an operator may first remove locking member (66) by pulling locking member (66) away from instrument (10), as can be seen in FIG. 3. Once locking member (66) is removed, actuation member (62) may be moved or translated relative to body (40) to advance needle (30) relative to cannula (20) as described in U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12, 2019, the disclosure of which is incorporated by reference herein. Actuation member (62) of the present example is only configured to translate needle (30) and not rotate needle (30). In other examples, it may be desirable to rotate needle (30). Accordingly, alternative examples may include features in actuation member (62) to rotate and translate needle (30).

In the present example, advancement of actuation member (62) into contact with body (40) as shown in FIG. 4 corresponds to advancement of needle (30) to a position relative to cannula (20) to a predetermined amount of penetration within an eye of a patient. In other words, instrument (10) is configured such that an operator only has to advance actuation member (62) into contact with body (40) to properly position needle (30) within an eye of a patient. In some examples, the predetermined amount of advancement of needle (30) relative to cannula (20) is between approximately 0.25 mm to approximately 10 mm; or more particularly within the range of approximately 0.1 mm to approximately 10 mm; or more particularly within the range of approximately 2 mm to approximately 6 mm; or more particularly to approximately 4 mm. In other examples, contact between actuation member (62) and body (40) may have no particular significance besides the maximum advancement of needle (30) relative to cannula (20). Instead, instrument (10) may be equipped with certain tactile feedback features to indicate to an operator when needle (30) has been advanced to certain predetermined distances relative to cannula (20). Accordingly, an operator may determine the desired depth of penetration of needle (30) into a patient's eye based on direct visualization of indicia on instrument and/or based on tactile feedback from instrument (10). Of course, such tactile feedback features may be combined with the present example, as will be apparent to those of ordinary skill in the art in view of the teachings herein.

II. EXEMPLARY ALTERNATIVE INSTRUMENTS AND FEATURES

In some examples, it may be desirable to vary certain components or features of the instruments described herein. For instance, it may be desirable to utilize instruments similar to instrument (10) with alternative mechanisms to actuate needle (30). Yet in other examples, it may be desirable to utilize instruments similar to instrument (10) equipped with different cannula (20) or needle (30) geometries. Instruments having the above referenced variations may be desirable for different surgical procedures, or surgical procedures similar to the procedure discussed above, to engage tissue structures having varying physical properties. While certain examples of variations are described herein, it should be understood that the instruments described herein may include any other alternative features as will be apparent to those of ordinary skill in the art in view of the teachings herein.

Figure 7:
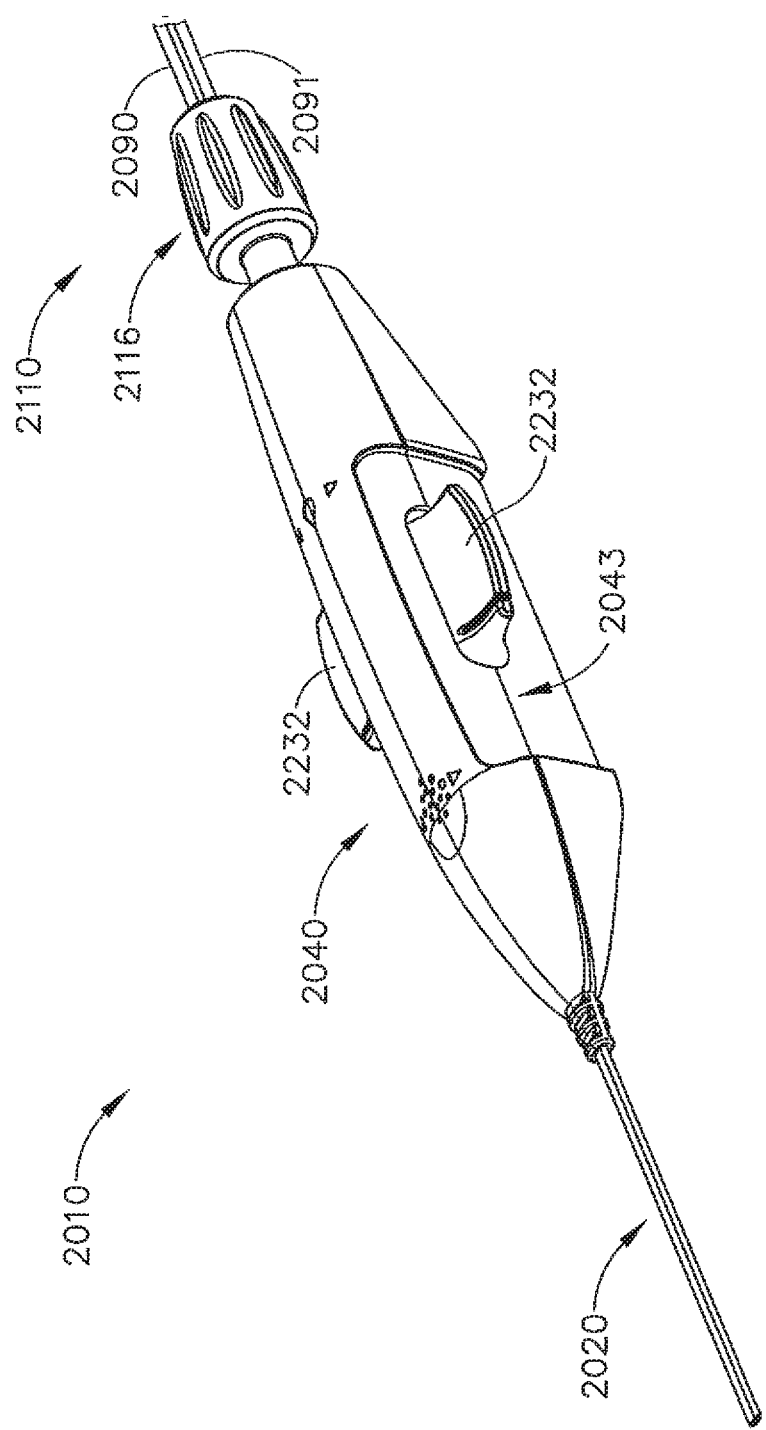
FIG. 7 depicts a perspective view of another exemplary alternative instrument for subretinal administration of a therapeutic agent from a suprachoroidal approach.

FIG. 7 shows an exemplary alternative instrument (2010) that is similar to instrument (10) described above. While certain features and operabilities of instrument (2010) are described below, it should be understood that, in addition to or in lieu of the following, instrument (2010) may be configured and/or operable in accordance with any of the teachings of U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12, 2019, the disclosure of which is incorporated by reference herein. Like with instrument (10), instrument (2010) of the present example is generally usable in the procedure described herein to deliver a therapeutic fluid subretinally to an eye of a patient from a suprachoroidal approach. It should therefore be understood that instrument (2010) may be readily used in place of instrument (10) to perform the medical procedures described herein. Like instrument (10), instrument (2010) of this example comprises a cannula (2020), a body (2040), and an actuation assembly (2100). Cannula (2020) includes a nitinol needle (2030) extending therethrough and is substantially the same as cannula (20) described above. In the present example, cannula (2020) and needle (2030) are substantially identical to cannula (20) and needle (30) described above.

The primary difference between instrument (10) and instrument (2010) is that actuation assembly (2100) of instrument (2010) is rotatable instead of being slidable. Additionally, instrument (2010) includes a valve assembly (not shown) that is operable to change the fluid state of needle (2030). Actuation assembly (2100) is generally operable to translate the valve assembly longitudinally to thereby translate needle (2030) longitudinally relative to cannula (2020) through rotation of a knob member (2110).

When actuation assembly (2100) is in the proximal position, an operator may rotate knob member (2110) in either a counter clockwise or clockwise direction. If knob member (2110) is rotated in the counter clockwise direction, rotation member (2110) will merely rotate freely. To begin advancement of actuation assembly (2100), the valve assembly, and needle (2030), an operator may rotate knob member (2110) in the clockwise direction. Clockwise rotation of knob member (2110) will act to translate knob member (2110) distally and will also act to translate the valve assembly and needle (2030) distally. An operator may continue clockwise rotation of knob member (2110) to drive needle (2030) out of the distal end of cannula (2020). Once needle (2030) has been advanced to its furthest distal position relative to the distal end of cannula (2020), further clockwise rotation of knob member (2110) will merely result in free rotation of knob member (2110) due to slipping of clutch features that are integrated into actuation assembly (2100). With needle (2030) in the distal position, the operator may actuate valve assembly to enable the delivery of therapeutic agent via needle (2030) as described in greater detail below.

After the therapeutic agent is delivered, the operator may then wish to retract needle (2030). Counter clockwise rotation of knob member (2110) will cause proximal translation of actuation assembly (2100), the valve assembly, and needle (2030) relative to body (2040). It should be understood that as actuation assembly (2100) is rotated to actuate the valve assembly, and needle (2030), the valve assembly and needle (2030) remain substantially rotationally stationary relative to body (2040). It should also be understood that although rotation member (2110) of the present example is described as being manually rotated, rotation member (2110) may be rotated via a motor and/or some other motive source. Thus, it should be understood that translation of needle (2030) may be mechanically/electrically driven via a servomotor. The actuation of a servomotor may be controlled by a servo controller as will be described in more detail below. Such a servo control may be manually operated. Additionally or alternatively, such a servo controller may be operated via a computer acting on feedback from instrument (2010) or any other component described herein.

III. EXEMPLARY SUTURE MEASUREMENT TEMPLATE

Figure 8:
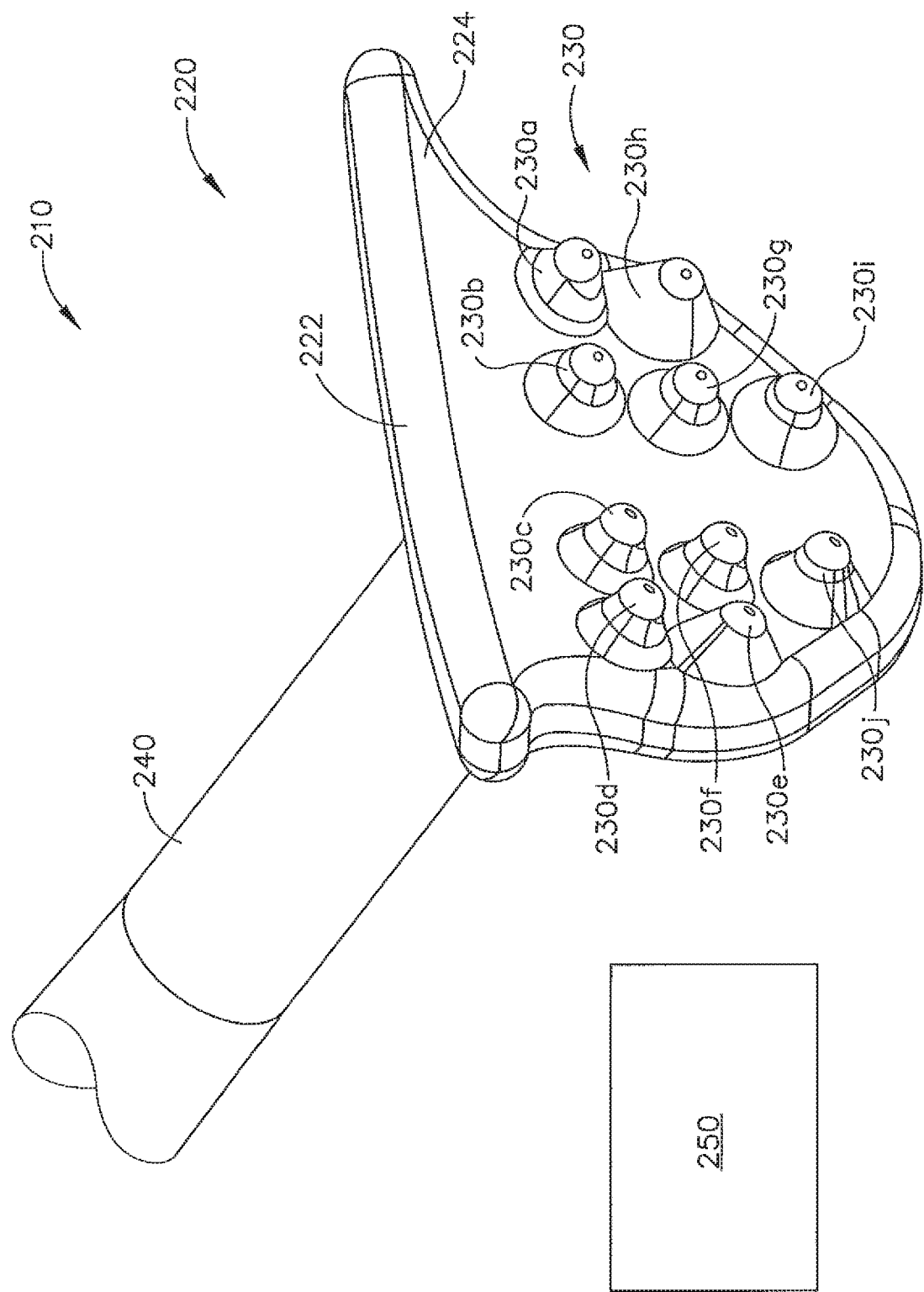
FIG. 8 depicts a perspective view of an exemplary suture measurement template for use in an exemplary method for the administration of a therapeutic agent from a suprachoroidal approach.

FIG. 8 shows an exemplary suture measurement template (210) that may be used in a procedure providing subretinal delivery of a therapeutic agent from a suprachoroidal approach, as will be described in greater detail below. Generally, template (210) is configured to be pressed against an eye of a patient to stamp a particular pattern of pigment onto the patient's eye. It should be understood that reference herein to pressing template (210) against an eye of a patent may include, but is not necessarily limited to, pressing template (210) directly against the sclera (304) surface (e.g., after the conjunctiva has been taken down or otherwise displaced). Template (210) comprises a rigid body (220) and a rigid shaft (240). As will be described in greater detail below, body (220) is generally contoured to correspond to the curvature of a patient's eye such that body (220) may be pressed or placed onto at least a portion of the patient's eye. Body (220) comprises an upper guide portion (222) and a plurality of protrusions (230) extending distally from an eye face (224) of body (220).

Upper guide portion (222) is generally semi-circular in shape and is disposed at the top of body (220). The semi-circular shape of upper guide portion (222) has a radius that corresponds to the curvature of the limbus of a patient's eye. In other words, upper guide portion (222) curves proximally along a first radius corresponding to a radius of curvature of a patient's eyeball; and downwardly (toward the longitudinal axis of shaft (240)) along a second radius corresponding to a radius of curvature of the limbus of the patient's eye. As will be described in greater detail below, upper guide portion (222) may be used to properly locate template (210) relative to the limbus of the patient's eye. Accordingly, any pigmentation that may be deposited onto a patient's eye by template may be positioned relative to the limbus of the patient's eye.

Protrusions (230) are spaced a predetermined distance from upper guide portion (222). In particular, protrusions (230) form a pattern that may correspond to relevant marks for use during the method described below. Protrusions (230) of the present example comprise four suture loop protrusions (230a-230h) and two sclerotomy protrusions (230i, 230j). Suture loop protrusions (230a-320h) and sclerotomy protrusions (230i, 230j) extend outwardly from body (220) an equal distance such that protrusions (230) collectively maintain the curvature defined by body (220). In other words, the tips of protrusions (230a-230j) all lie along a curved plane that is defined by a radius of curvature complementing the radius of curvature of the patient's eyeball. The tips of protrusions (230a-230j) are rounded and atraumatic such that protrusions (230a-230j) may be pressed against the eye without damaging the sclera or other portions of the patient's eye.

Shaft (240) extends proximally from body (220). Shaft (240) is configured to permit an operator to grasp template (210) and manipulate body (220). In the present example, shaft (240) is integral with body (220). In other examples, shaft (240) may be selectively attachable to body by a mechanical fastening means such as a threaded coupling or a mechanical snap fit, etc. In some versions, an operator may be presented with a kit comprising a shaft (240) and a plurality of bodies (220). The bodies (220) may have different curvatures to correspond with different eyeballs having different radii of curvature. The operator may thus select an appropriate body (220) from the kit based on the anatomy of the particular patient before the operator; and the operator may then secure the selected body (220) to the shaft (240). Although not shown, it should be understood that the proximal end of shaft (240) may additionally include a t-grip, knob, or other gripping feature to permit an operator to more readily grip shaft (240).

In an exemplary use, suture loop protrusions (232) and sclerotomy protrusions (234) each correspond to a particular portion of the method described below. In particular, prior to, or during the method described below, an operator may coat protrusions (230) with a biocompatible pigment or ink by pressing protrusions (230) onto a pigment or ink pad (250), by brushing the pigment or ink onto protrusions (230), or by otherwise applying the pigment or ink to protrusions (230). Once protrusions (230) have received the pigment or ink, an operator may mark an eye of a patent by pressing protrusions (230) of template (210) onto the eye of the patient, as will be described in greater detail below. Once template (210) is removed from an eye of a patient, the pigment from protrusions may remain adhered to the eye to mark particular points of interest, as will be described in greater detail below.

IV. EXEMPLARY METHOD FOR SUBRETINAL DELIVERY OF THERAPEUTIC AGENT FROM A SUPRACHOROIDAL APPROACH

FIGS. 9A-11C show an exemplary procedure for subretinal delivery of therapeutic agent from a suprachoroidal approach using instrument (10) described above. It should be understood however, that instrument (2010) may be readily used in addition to or in lieu of instrument (10) in the procedure described below. By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

As can be seen in FIG. 9A, the procedure begins by an operator immobilizing tissue surrounding a patient's eye (301) (e.g., the eyelids) using a speculum (312), and/or any other instrument suitable for immobilization. While is immobilization described herein with reference to tissue surrounding eye (301), it should be understood that eye (301) itself may remain free to move. Once the tissue surrounding eye (301) has been immobilized, an eye chandelier port (314) is inserted into eye (301) to provide intraocular illumination when the interior of eye (301) is viewed through the pupil. In the present example, eye chandelier port (314) is positioned in the inferior medial quadrant such that a superior temporal quadrant sclerotomy may be preformed. As can be seen in FIG. 10A, eye chandelier port (314) is positioned to direct light onto the interior of eye (314) to illuminate at least a portion of the retina (e.g., including at least a portion of the macula). As will be understood, such illumination corresponds to an area of eye (301) that is being targeted for delivery of therapeutic agent. In the present example, only chandelier port (314) is inserted at this stage, without yet inserting an optical fiber (315) into port (314). In some other versions, an optical fiber (315) may be inserted into chandelier port (314) at this stage. In either case, a microscope may optionally be utilized to visually inspect the eye to confirm proper positioning of eye chandelier port (314) relative to the target site. In some examples, the target region may be identified by a relative lack of retinal pigmentation. Although FIG. 9A shows a particular positioning of eye chandelier port (314), it should be understood that eye chandelier port (314) may have any other positioning as will be apparent to those of ordinary skill in the art in view of the teachings herein.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. Template (210), described above, may then be used to mark eye (301).

Figure 9B:
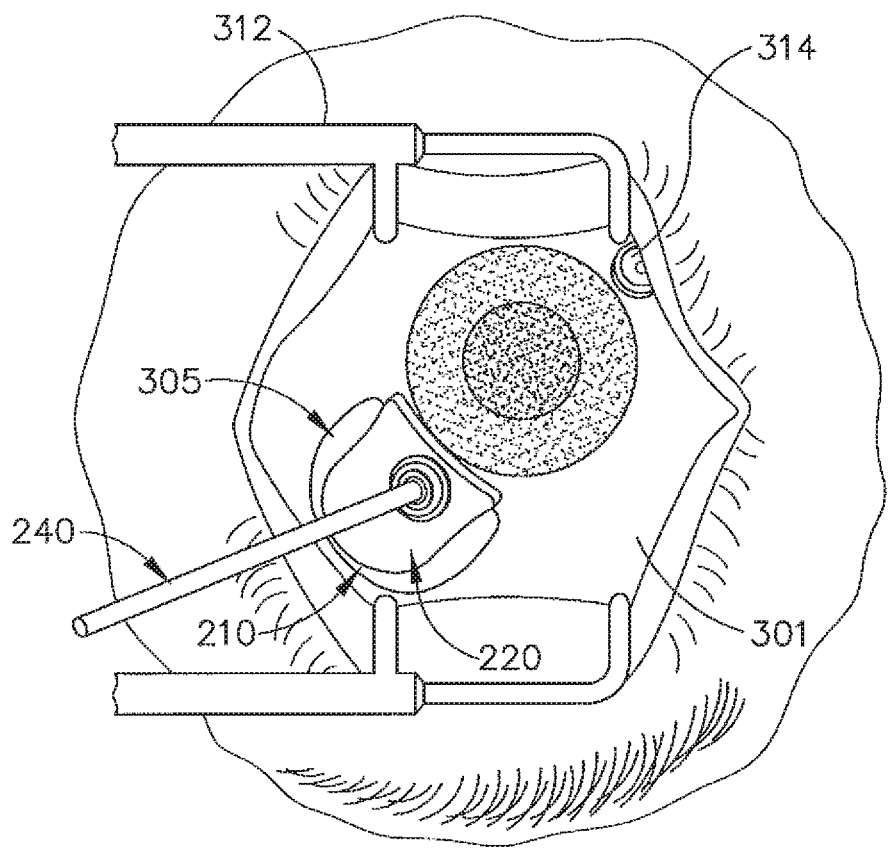
FIG. 9B depicts a top plan view of the eye of FIG. 9A, with the template of FIG. 8 disposed on the eye.
Figure 9C:
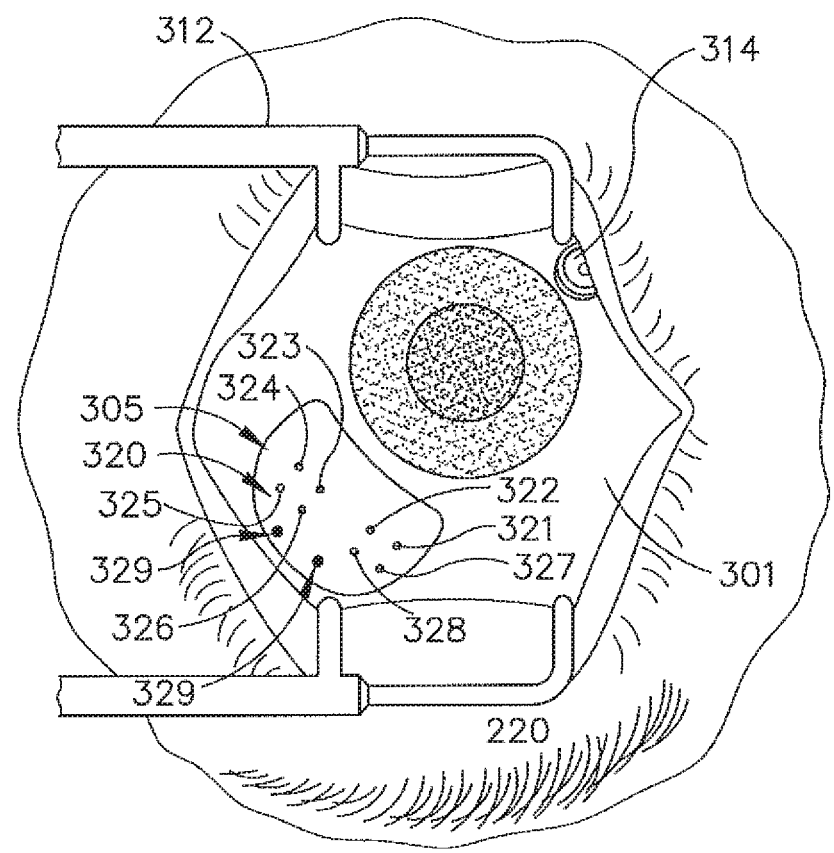
FIG. 9C depicts a top plan view of the eye of FIG. 9A, with a plurality of markers disposed on the eye.
Figure 10A:
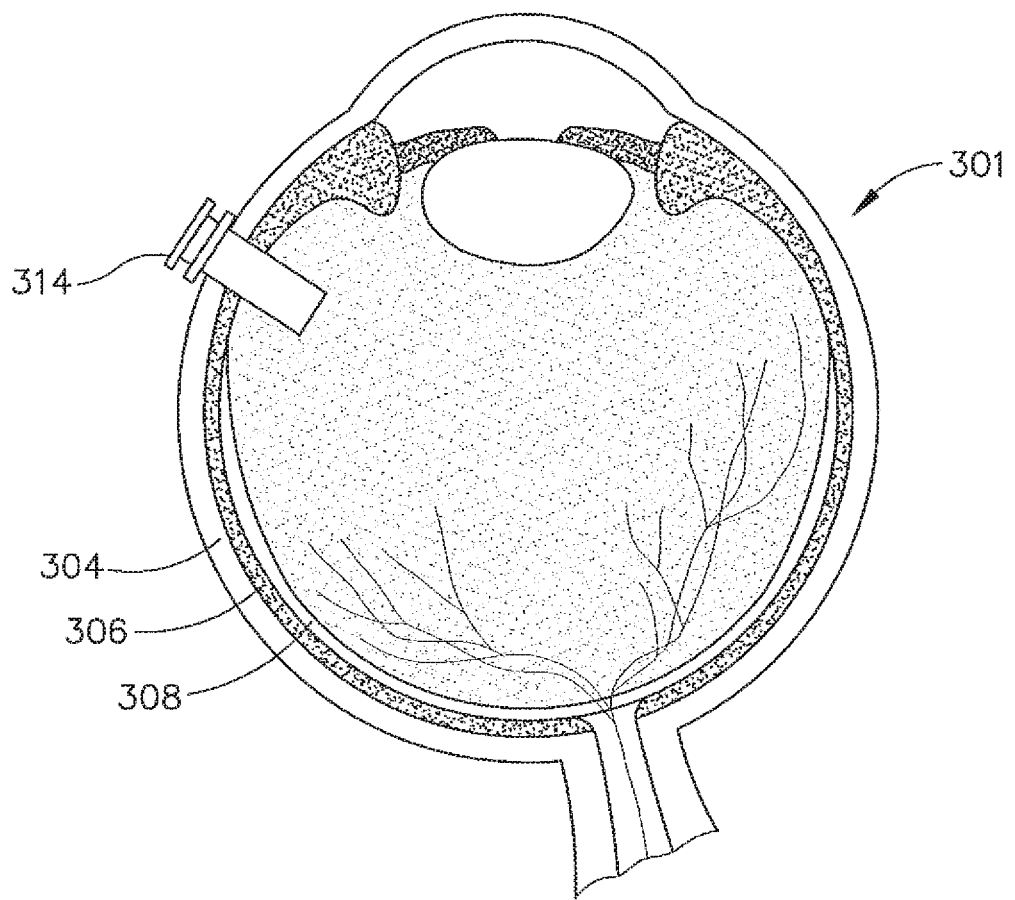
FIG. 10A depicts a cross-sectional view of the eye of FIG. 9A, with the cross-section taken about line 10A-10A of FIG. 9A.
Figure 10B:
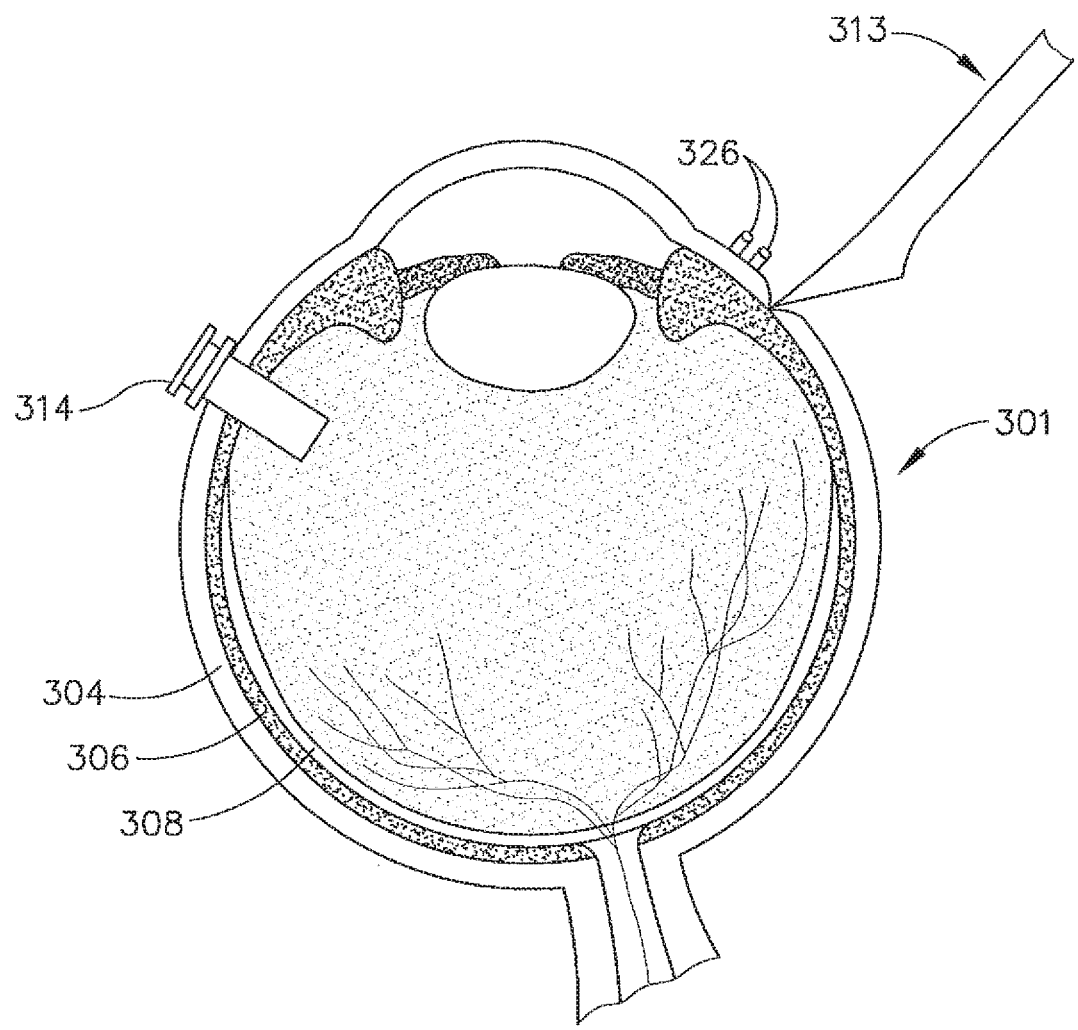
FIG. 10B depicts a cross-sectional view of the eye of FIG. 9A, with the cross-section taken about line 10B-10B of FIG. 9E.

As can be seen in FIG. 9B, template (210) is positioned to align with the limbus of eye (301). An operator may apply a light force to template (210) to apply pigment to eye (301). Template (210) is then removed, leaving pigment adhered to the exposed surface (305) of the sclera (304) to provide a visual guide (320) for an operator, as can be seen in FIG. 9C. An operator may then use visual guide (320) to attach a suture loop assembly (330) and to perform a sclerotomy. Visual guide (320) comprises a set of suture loop markers (321, 322, 323, 324, 325, 326, 327) and a pair of sclerotomy markers (329).

Figure 9D:
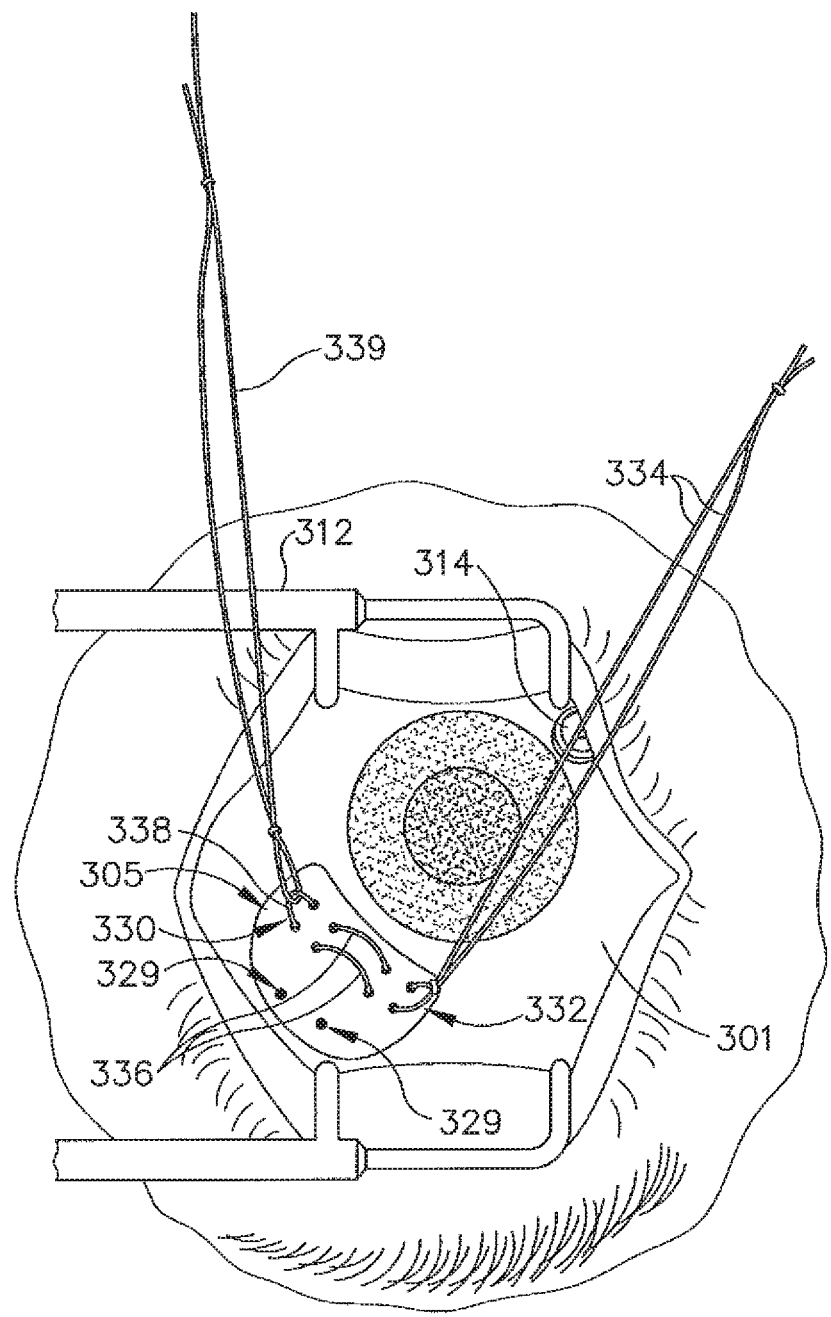
FIG. 9D depicts a top plan view of the eye of FIG. 9A, with a suture loop attached to the eye.
Figure 9E:
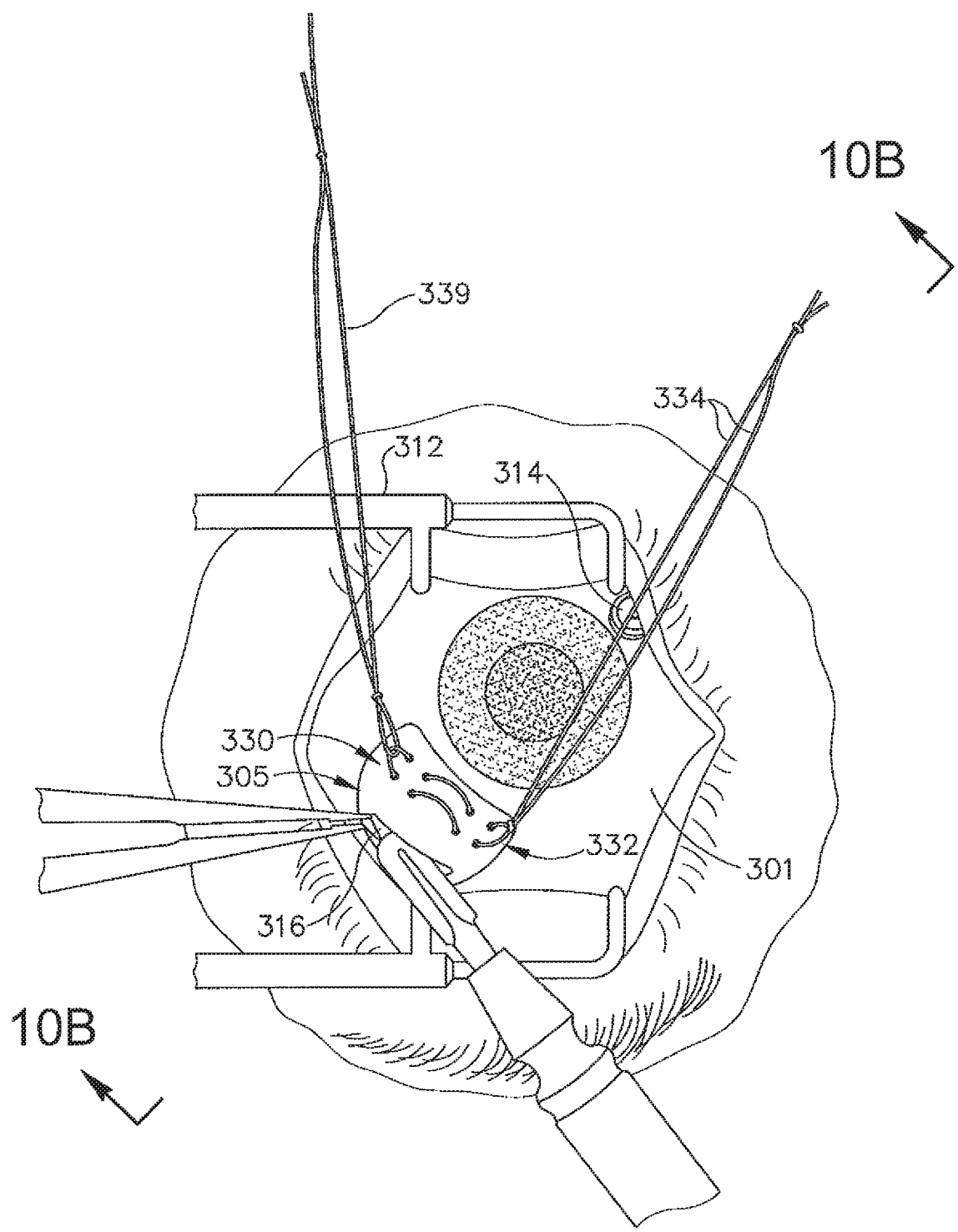
FIG. 9E depicts a top plan view of the eye of FIG. 9A, with a sclerotomy being performed.

FIG. 9D shows a completed suture loop assembly (330). As will be described in greater detail below, suture loop assembly (330) is generally configured to guide cannula (20) of instrument (10) through a sclerotomy and into eye (301). An exemplary procedure that may be employed to create the suture loop assembly (330) that is shown in FIG. 9D is described in U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12, 2019, the disclosure of which is incorporated by reference herein. Once suture loop assembly (330) has been attached to eye (301), a sclerotomy may be performed on eye (301). As seen in FIG. 9E, eye (301) is cut between sclerotomy markers (329) using a conventional scalpel (313) or other suitable cutting instrument. Although sclerotomy markers (329) are shown as comprising two discrete dots, it should be understood that in other examples, markers (329) may comprise any other type of markings such as a solid, dotted or dashed line. The sclerotomy procedure forms a small incision (316) through sclera (304) of eye (301). As can best be seen in FIG. 10B, the sclerotomy is preformed with particular care to avoid penetration of the choroid (306). Thus, the sclerotomy procedure provides access to the space between sclera (304) and choroid (306). Once incision (316) is made in eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 9F:
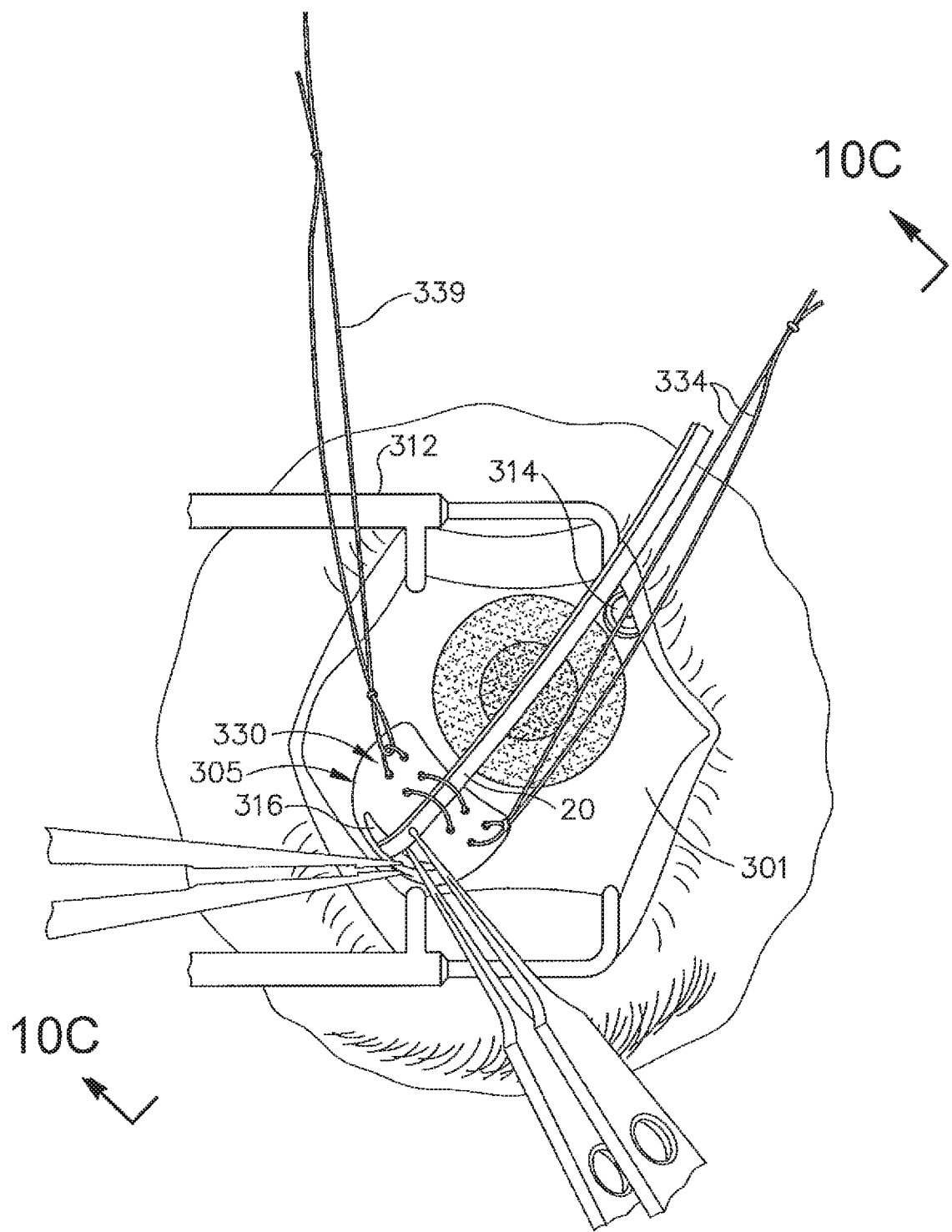
FIG. 9F depicts a top plan view of the eye of FIG. 9A, with the instrument of FIG. 1 being inserted through the sclerotomy opening and in between the sclera and choroid of the eye.

With the sclerotomy procedure performed, an operator may insert cannula (20) of instrument (10) through incision (316) and into the space between sclera (304) and choroid (306). As can be seen in FIG. 9F, cannula (20) is directed through guide loops (336) of suture loop assembly (330) and into incision (316). As described above, guide loops (336) may stabilize cannula (20). Additionally, guide loops (336) maintain cannula (20) in a generally tangential orientation relative to incision (316). Such tangential orientation may reduce trauma as cannula (20) is guided through incision (316) to stabilize cannula (20) and to prevent damage to surrounding tissue. As cannula (20) is inserted into incision (316) through guide loops (336), an operator may use forceps or other instruments to further guide cannula (20) along an atraumatic path. Of course, use of forceps or other instruments is merely optional, and may be omitted in some examples. Although not shown, it should be understood that in some examples cannula (20) may include one or more markers on the surface of cannula (20) to indicate various depths of insertion. While merely optional, such markers may be desirable to aid an operator in identifying the proper depth of insertion as cannula (20) is guided along an atraumatic path. For instance, the operator may visually observe the position of such markers in relation to guide loops (336) and/or in relation to incision (316) as an indication of the depth to which cannula (20) is inserted in eye (301). By way of example only, one such marker may correspond to an approximately 6 mm depth of insertion of cannula (20).

Once cannula (20) is at least partially inserted into eye (301), an operator may insert an optical fiber (315) into eye chandelier port (314) the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (20) may optionally be made at this point to ensure proper positioning relative to the area of geographic atrophy of retina (308). In some instances, the operator may wish to rotate the eye (301), such as by pulling on sutures (334, 339), to direct the pupil of the eye (301) toward the operator in order to optimize visualization of the interior of the eye (301) via the pupil.

Figure 9G:
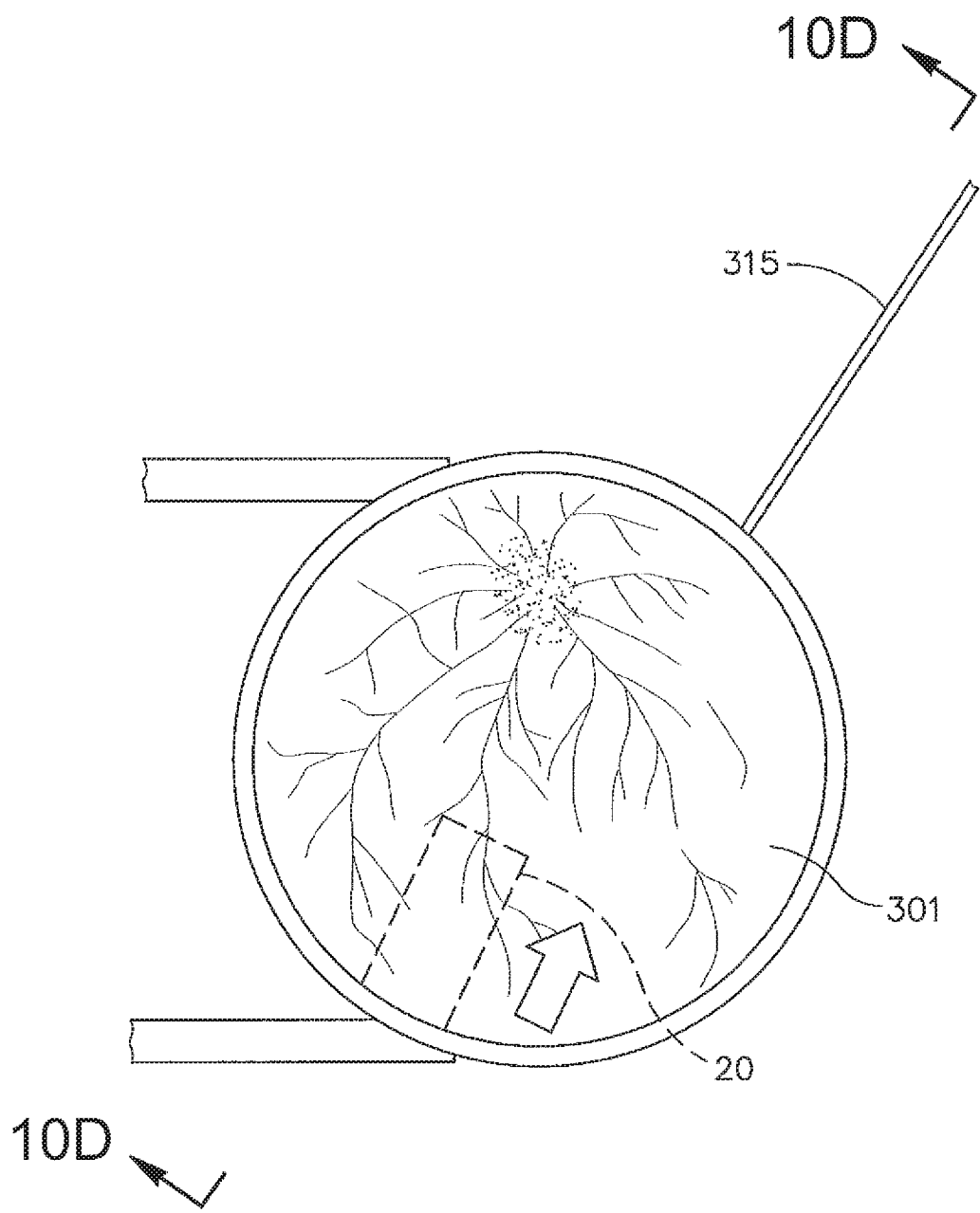
FIG. 9G depicts a top plan view of the eye of FIG. 9A, with the instrument of FIG. 1 under direct visualization at the back of the eye, between the sclera and choroid.
Figure 10C:
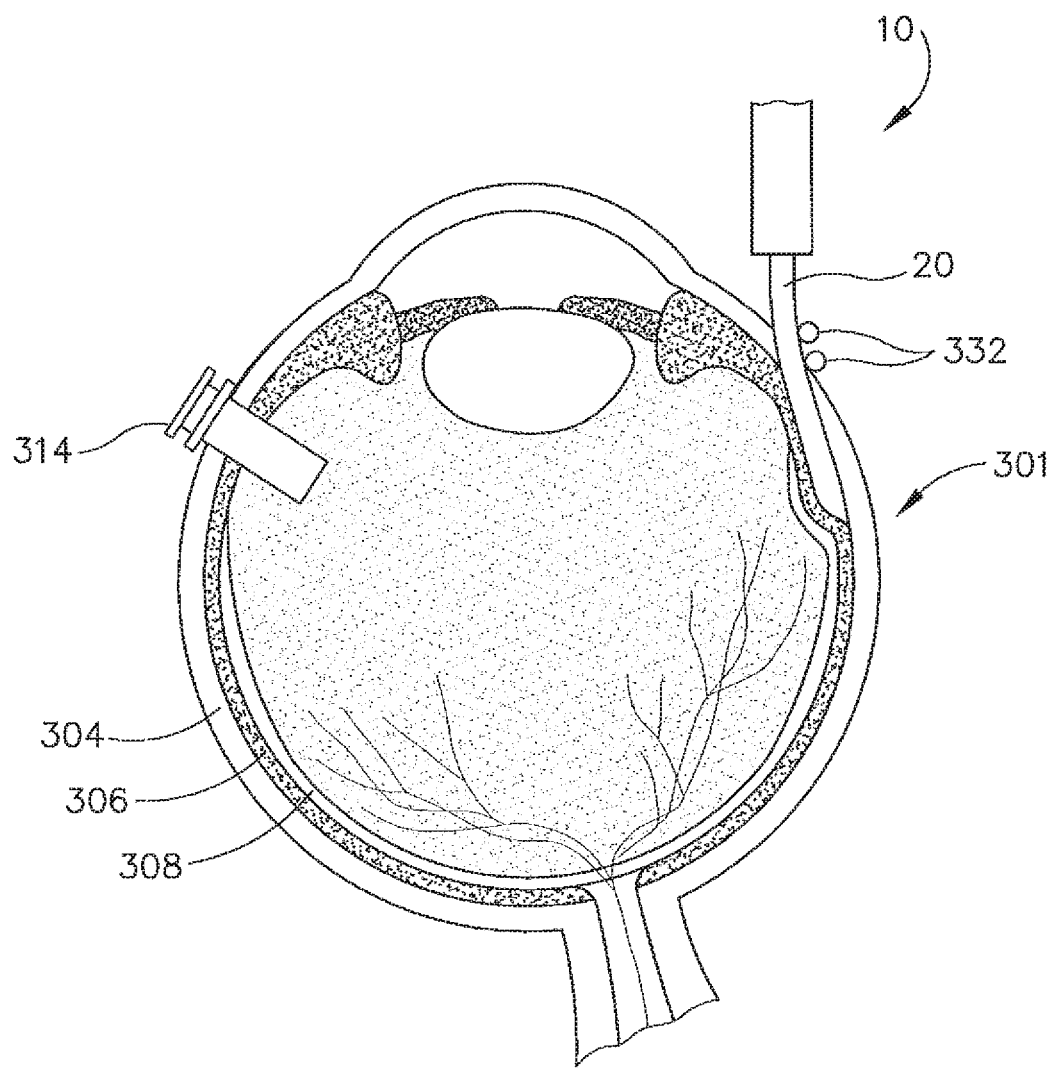
FIG. 10C depicts a cross-sectional view of the eye of FIG. 9A, with the cross-section taken about line 10C-10C of FIG. 9F.
Figure 10D:
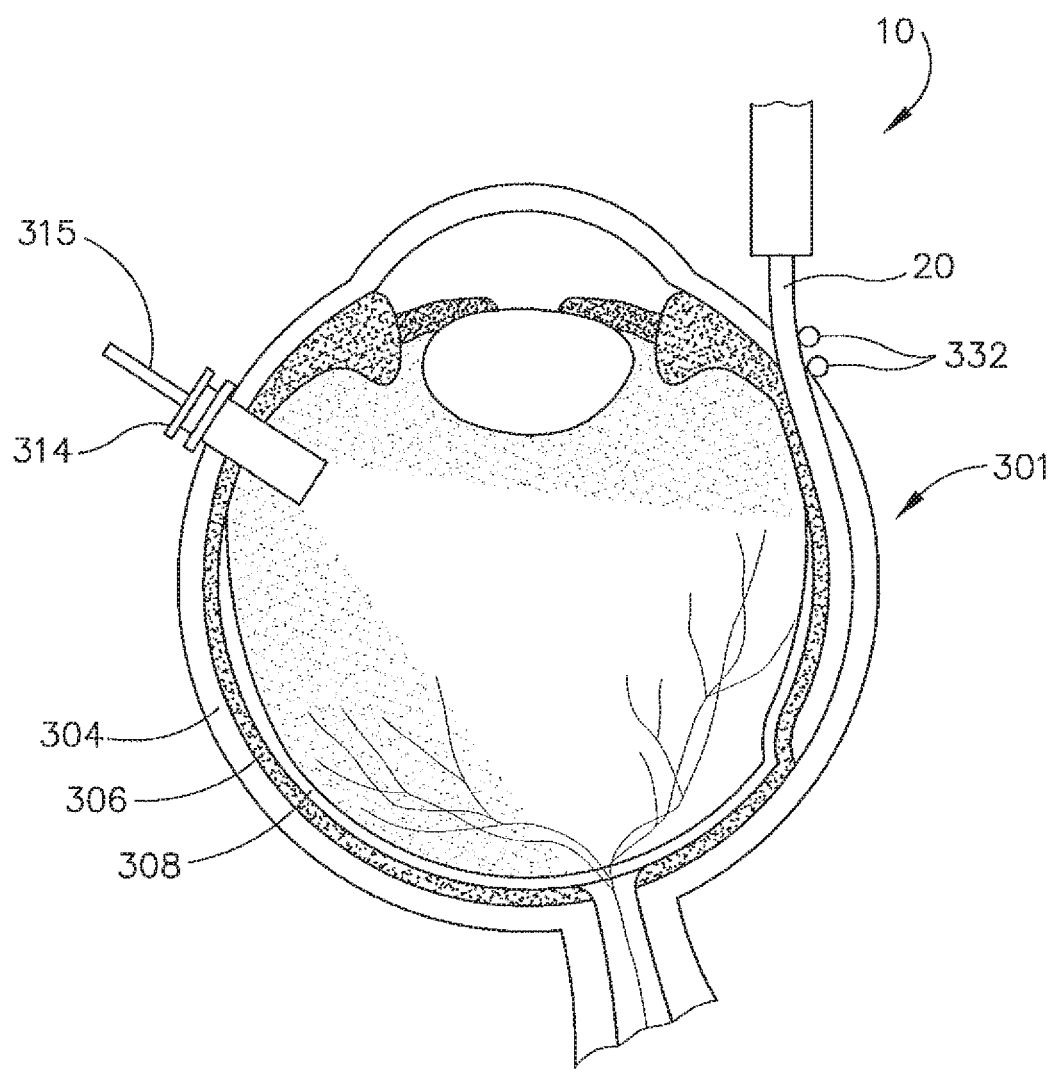
FIG. 10D depicts a cross-sectional view of the eye of FIG. 9A, with the cross-section taken about line 10D-10D of FIG. 9G.
Figure 10E:
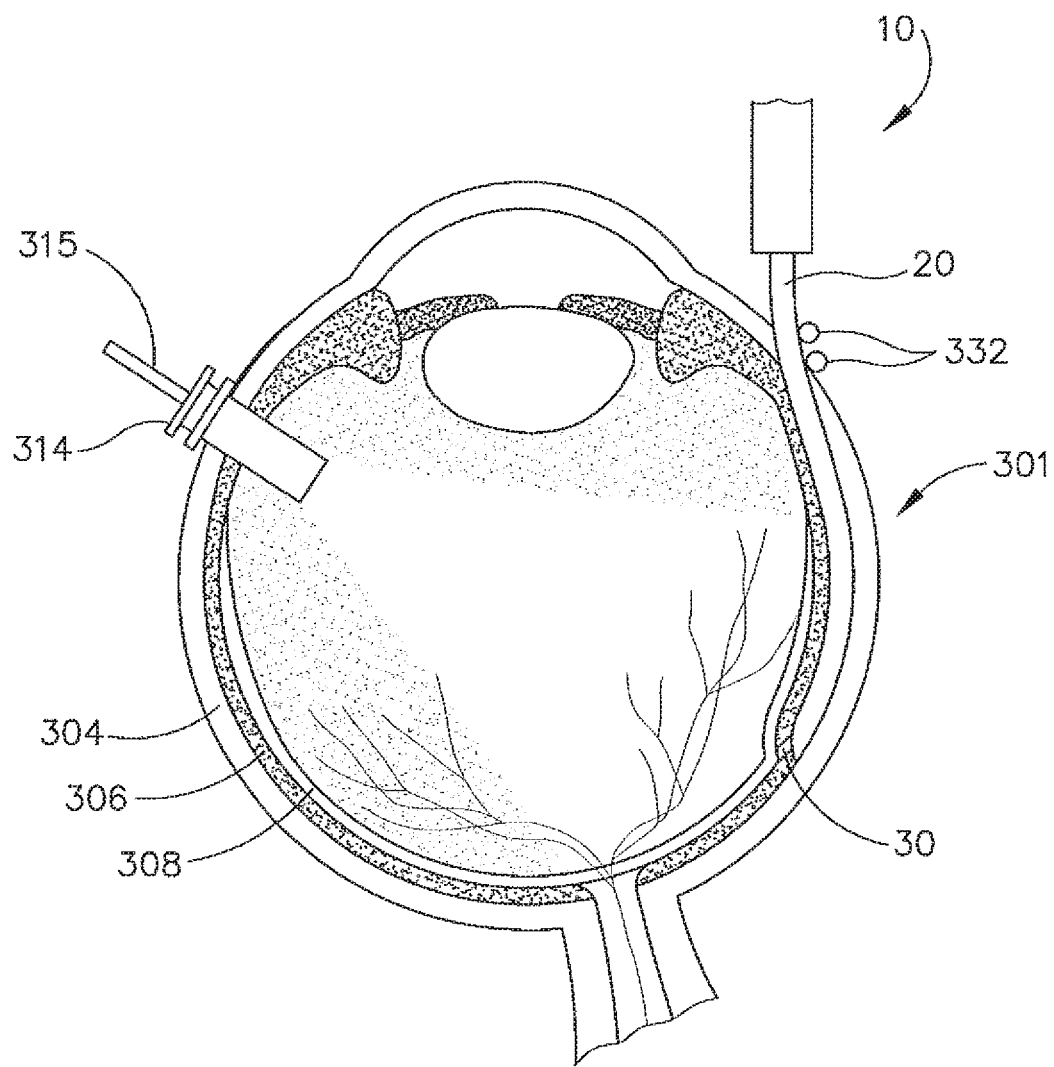
FIG. 10E depicts a cross-sectional view of the eye of FIG. 9A, with the cross-section taken about line 10E-10E of FIG. 9H.

FIGS. 9G and 10C-10D show cannula (20) as it is guided between sclera (304) and choroid (306) to the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. FIG. 9G shows eye (301) under direct visualization through a microscope directed through the pupil of eye (301), with illumination provided through fiber (315) and port (314). As can be seen, cannula (20) is at least partially visible through a retina (308) and choroid (306) of eye (301). Thus, an operator may track cannula (20) as it is advanced through eye (301) from the position shown in FIG. 10C to the position shown in 10D. Such tracking may be enhanced in versions where an optical fiber (34) is used to emit visible light through the distal end of cannula (20).

Figure 9H:
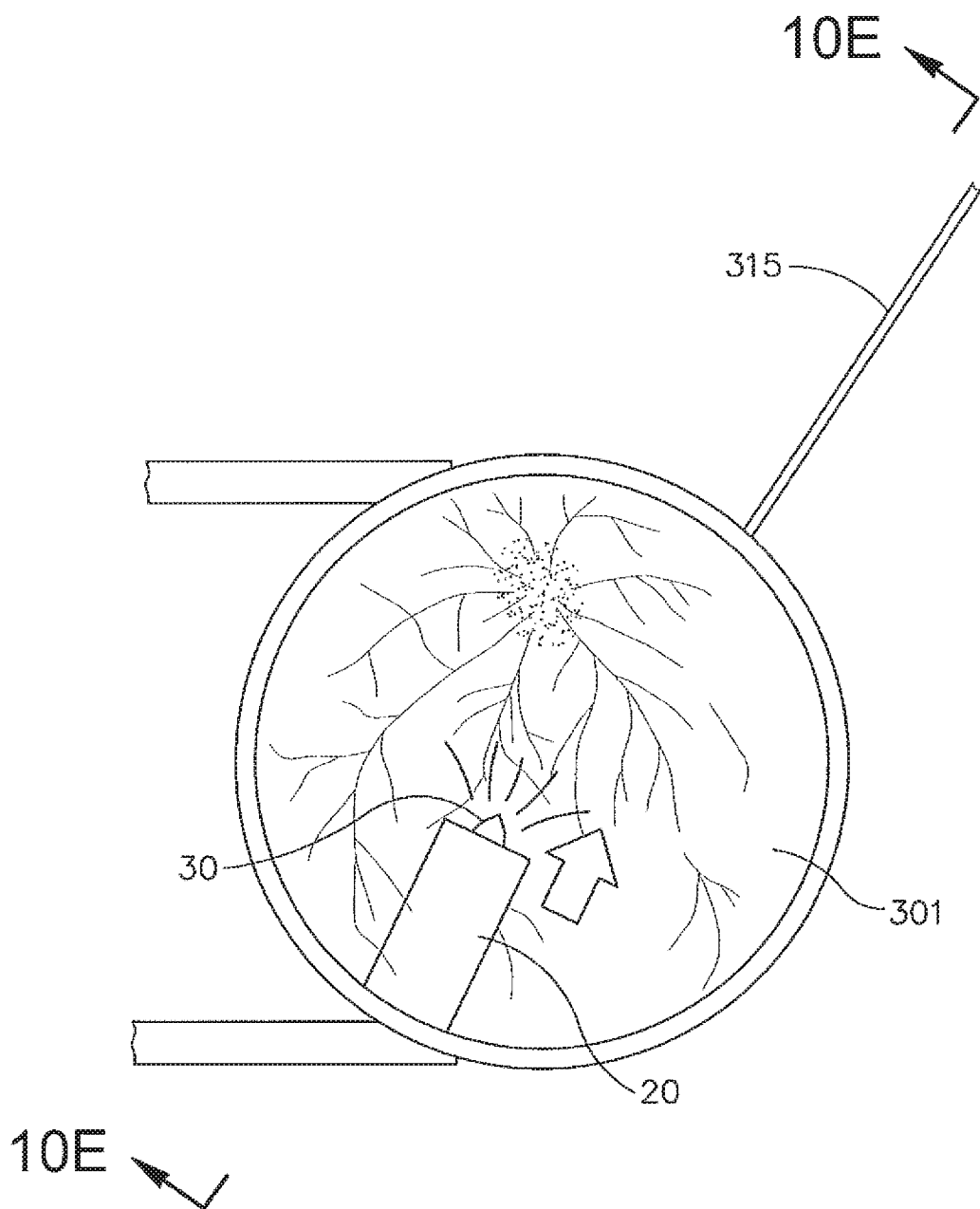
FIG. 9H depicts a top plan view of the eye of FIG. 9A, with the needle of the instrument of FIG. 1 being advanced under direct visualization at the back of the eye, pressing against the outer surface of the choroid causing the choroid to 'tent'.

Once cannula (20) has been advanced to the delivery site as shown in FIG. 10D, an operator may advance needle (30) of instrument (10) as described above with respect to FIGS. 3-4. As can be seen in FIGS. 9H-9I, 10E, and 11A, needle (30) is advanced relative to cannula (20) such that needle (30) pierces through choroid (306) without penetrating retina (308). Immediately prior to penetrating choroid (306), needle (30) may appear under direct visualization as "tenting" the surface of choroid (306), as can be seen in FIG. 9H. In other words, needle (30) may deform choroid (306) by pushing upwardly on choroid, providing an appearance similar to a tent pole deforming the roof of a tent. Such a visual phenomenon may be used by an operator to identify whether choroid (306) is about to be pierced and the location of any eventual piercing. The particular amount of needle (30) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, a merely exemplary range of needle (30) advancement may be between approximately 0.25 mm and approximately 10 mm; or more particularly between approximately 2 mm and approximately 6 mm.

Figure 9I:
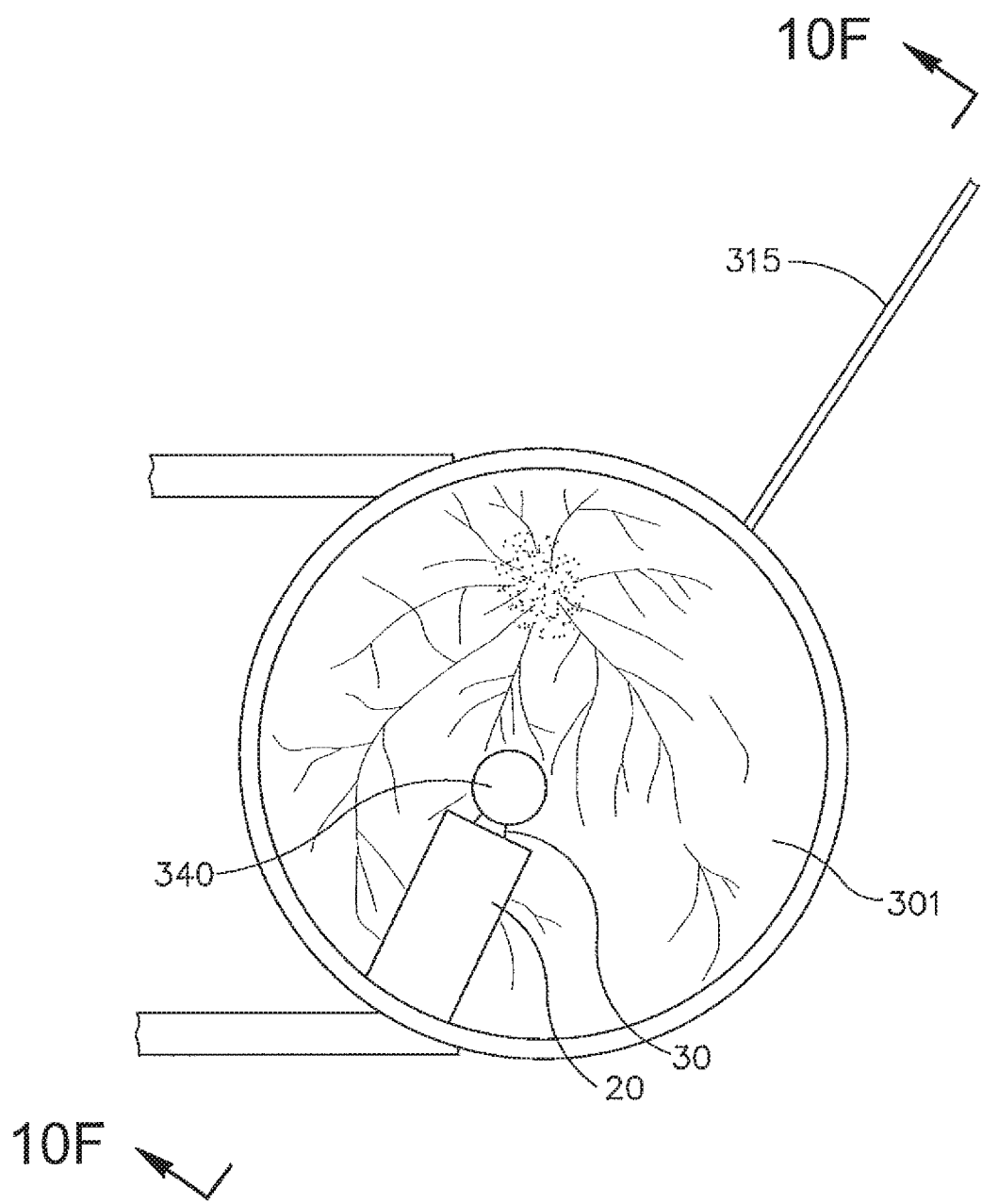
FIG. 9I depicts a top plan view of the eye of FIG. 9A, with the needle dispensing a leading bleb under direct visualization at the back of the eye, the needle between the sclera and choroid, and the leading bleb in the sub retinal space between the choroid and a retina.
Figure 10F:
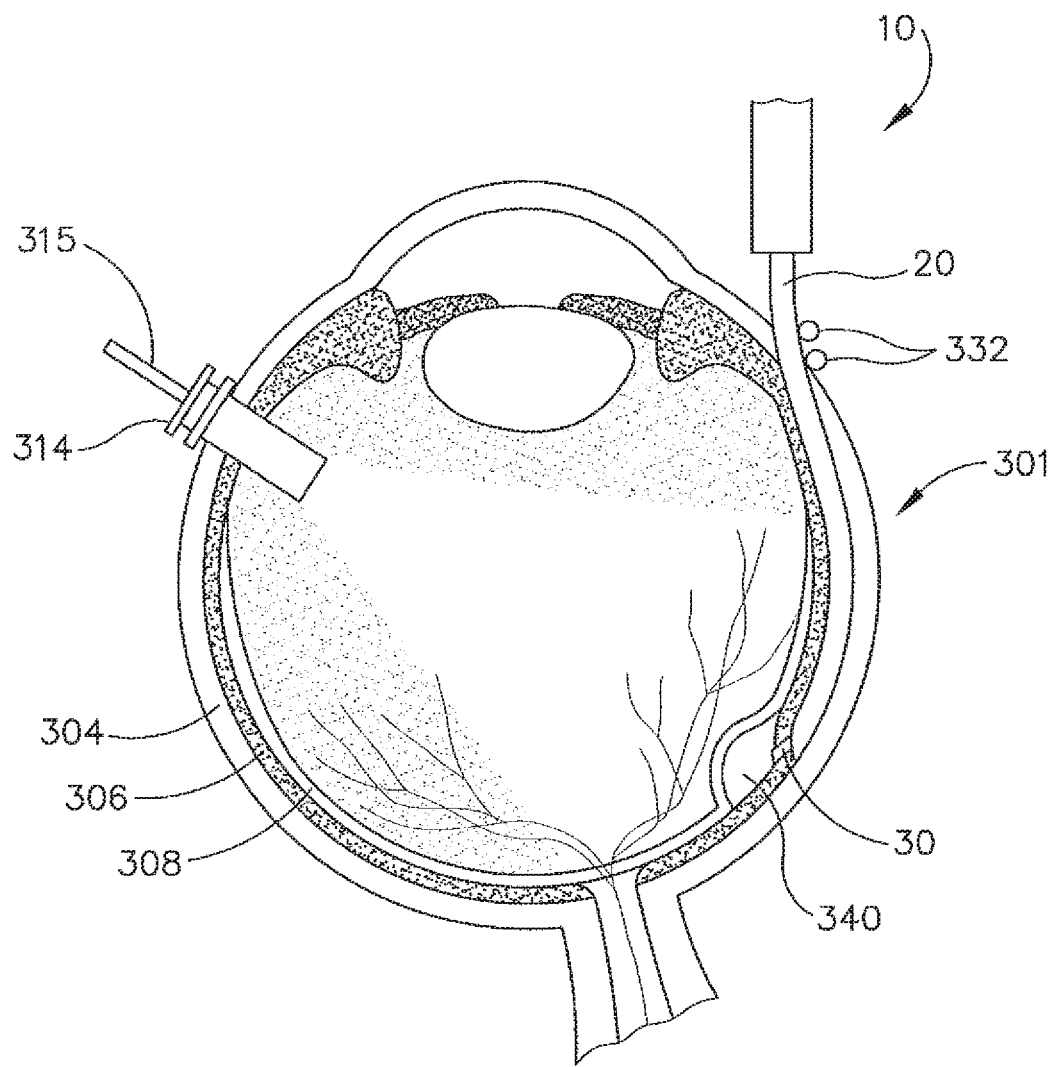
FIG. 10F depicts a cross-sectional view of the eye of FIG. 9A, with the cross-section taken about line 10F-10F of FIG. 9I.
Figure 11A:
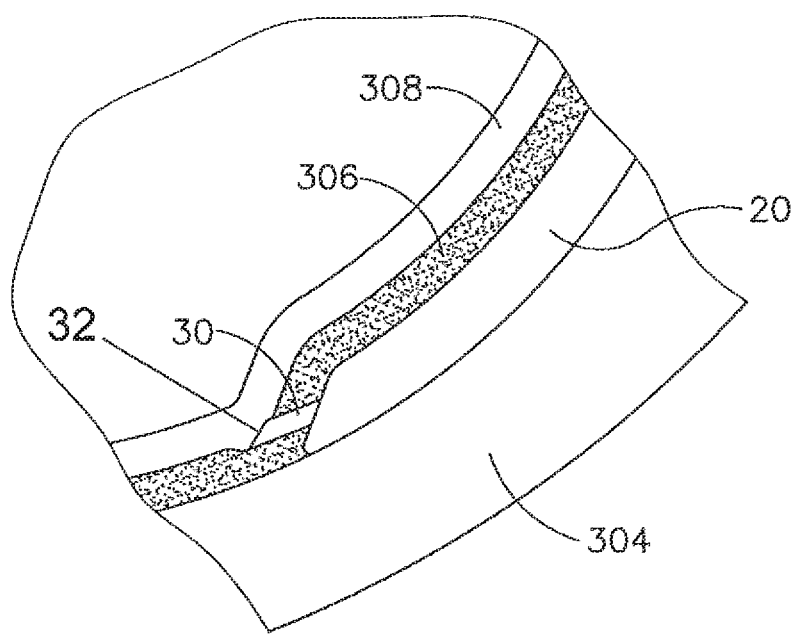
FIG. 11A depicts a detailed cross-sectional view of the eye of FIG. 9A depicted in the state shown in FIG. 10E.
Figure 11B:
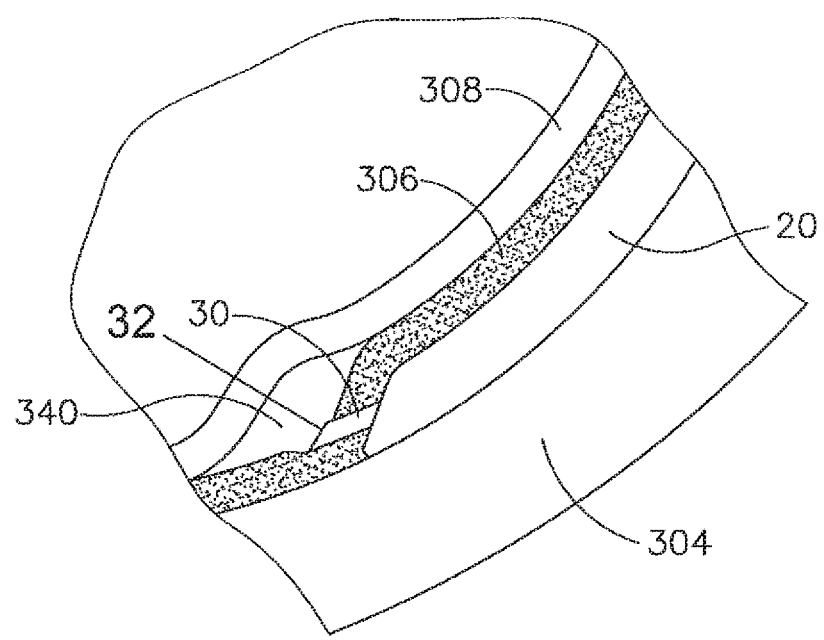
FIG. 11B depicts a detailed cross-sectional view of the eye of FIG. 9A depicted in the state shown in FIG. 10F.

In the present example, after the operator has confirmed that needle (30) has been properly advanced by visualizing the tenting effect described above, the operator infuses a balanced salt solution (BSS) or other similar solution as needle (30) is advanced relative to cannula (20). Such a BSS solution may form a leading bleb (340) ahead of needle (30) as needle (30) is advanced through choroid (306). Leading bleb (340) may be desirable for two reasons. First, as shown in FIGS. 9I, 10F, and 11B, leading bleb (340) may provide a further visual indicator to an operator to indicate when needle (30) is properly positioned at the delivery site. Second, leading bleb (340) may provide a barrier between needle (30) and retina (308) once needle (30) has penetrated choroid (306). Such a barrier may push the retinal wall outwardly (as is best seen in FIGS. 10F and 11B), thereby minimizing the risk of retinal perforation as needle (30) is advanced to the delivery site. In some versions, a foot pedal is actuated in order to drive leading bleb (340) out from needle (30). Alternatively, other suitable features that may be used to drive leading bleb (340) out from needle (30) will be apparent to those of ordinary skill in the art in view of the teachings herein.

Once the operator visualizes leading bleb (340), the operator may cease infusion of BSS, leaving a pocket of fluid as can be seen in FIGS. 9I, 10F, and 11B. Next, a therapeutic agent (341) may be infused by actuating a syringe or other fluid delivery device as described above with respect to instrument (10). The particular therapeutic agent (341) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, and/or any other suitable therapeutic agent as will be apparent to those of ordinary skill in the art in view of the teachings herein. By way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein.

Figure 9J:
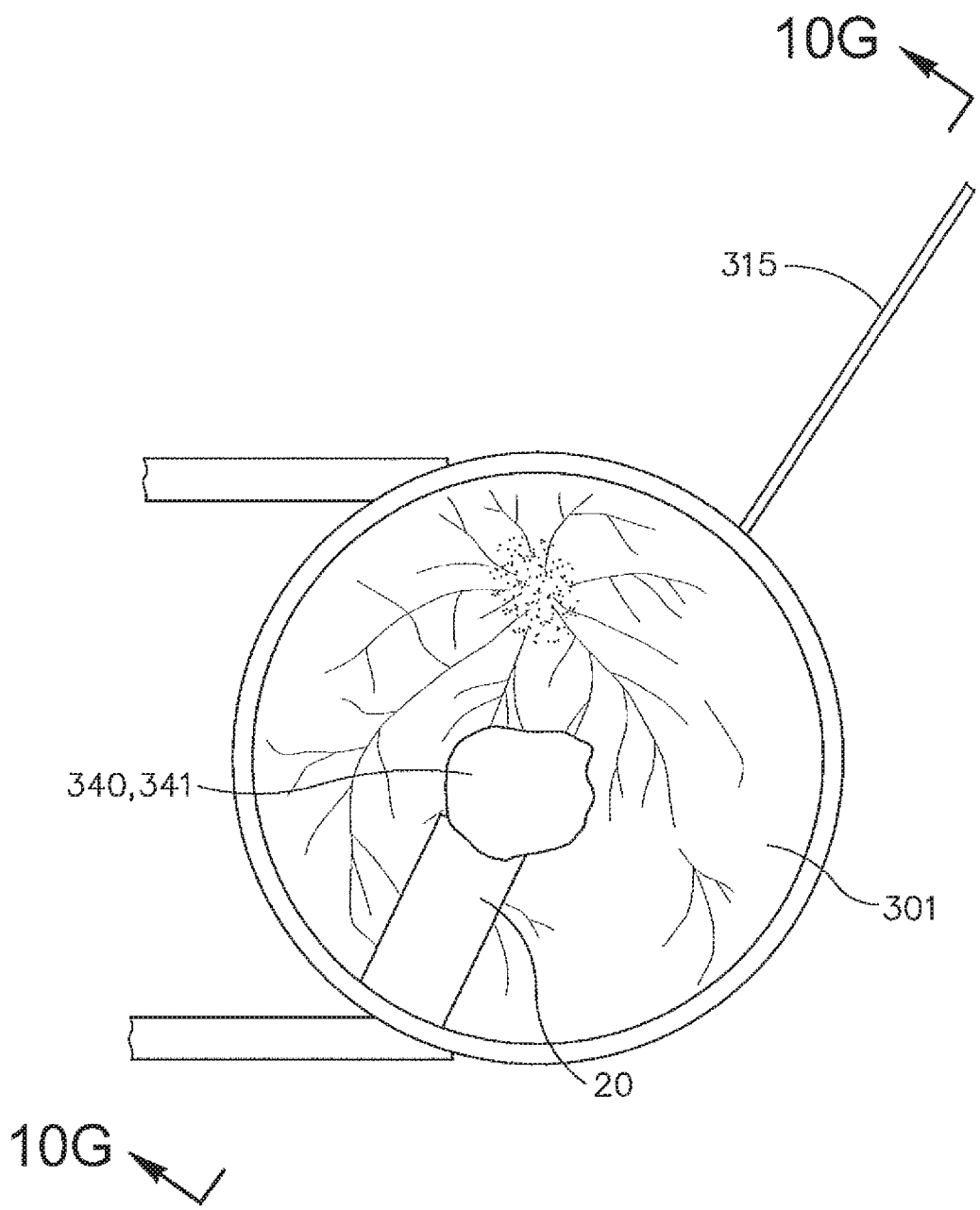
FIG. 9J depicts a top plan view of the eye of FIG. 9A, with the needle dispensing a therapeutic agent to the eye at the back of the eye, between the sclera and choroid.
Figure 10G:
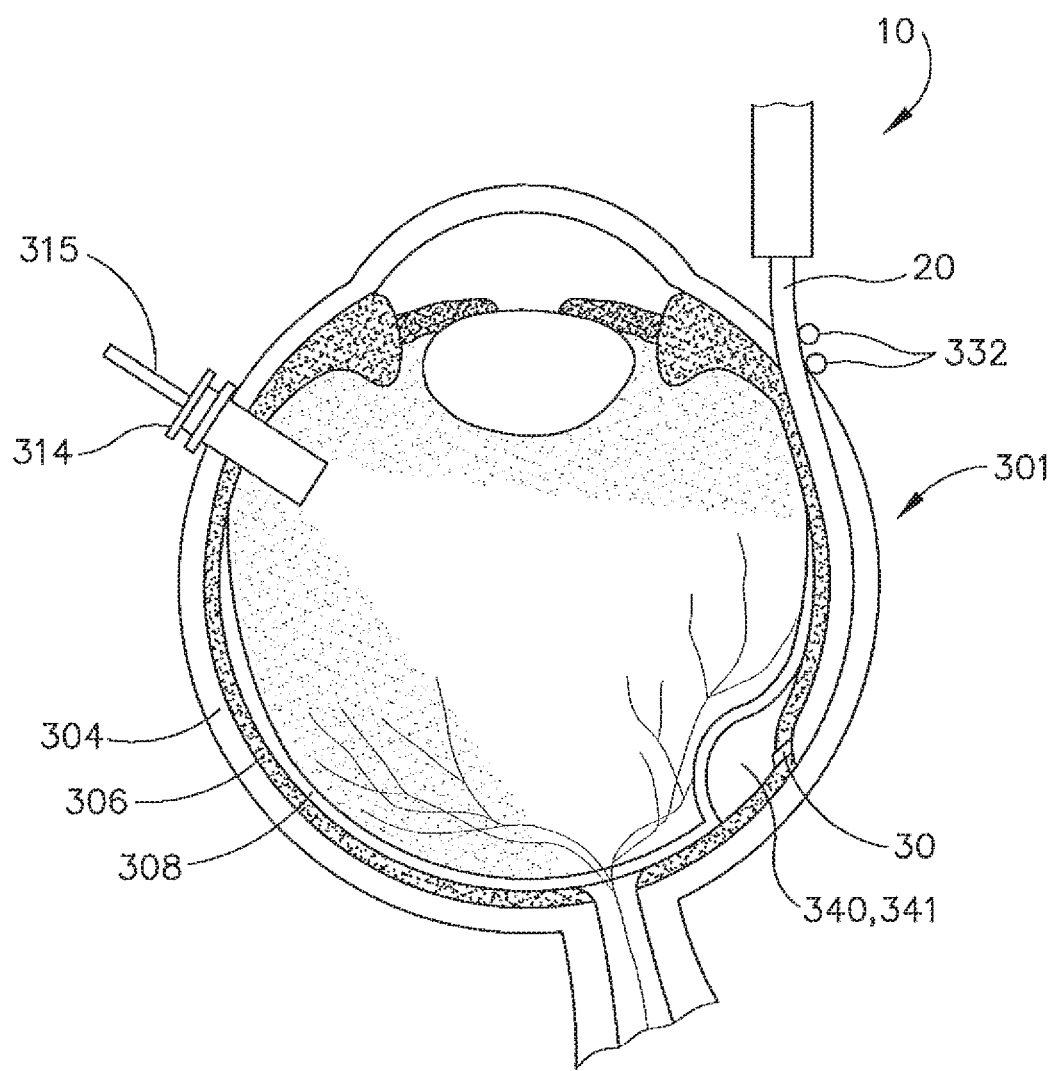
FIG. 10G depicts a cross-sectional view of the eye of FIG. 9A, with the cross-section taken about line 10G-10G of FIG. 9J.
Figure 11C:
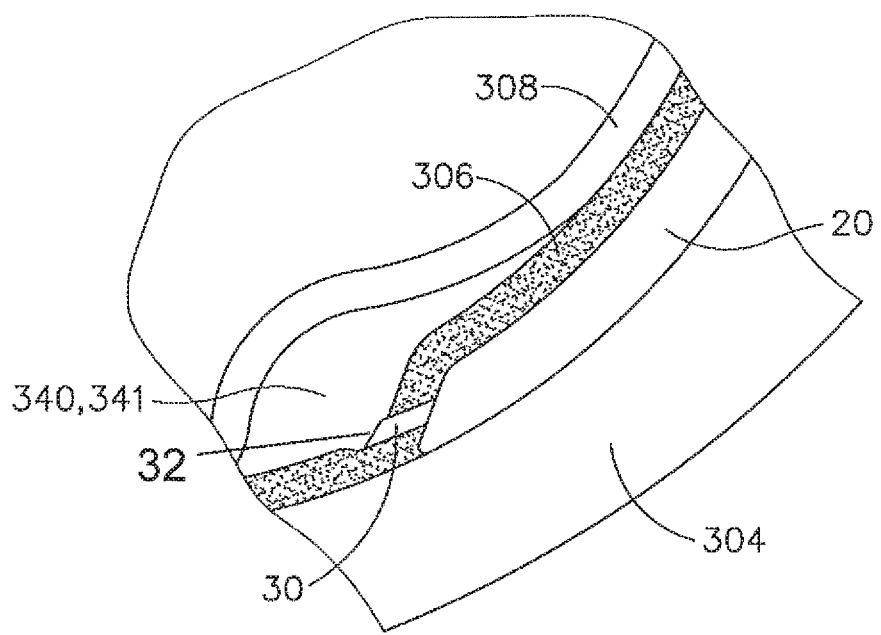
FIG. 11C depicts a detailed cross-sectional view of the eye of FIG. 9A depicted in the state shown in FIG. 10G.

In the present example, the amount of therapeutic agent (341) that is ultimately delivered to the delivery site is approximately 50 µL, although any other suitable amount may be delivered. In some versions, a foot pedal is actuated in order to drive agent (341) out from needle (30). Alternatively, other suitable features that may be used to drive agent (341) out from needle (30) will be apparent to those of ordinary skill in the art in view of the teachings herein. Delivery of therapeutic agent may be visualized by an expansion of the pocket of fluid as can be seen in FIGS. 9J, 10G, and 11C. As shown, therapeutic agent (341) essentially mixes with the fluid of leading bleb (340) as therapeutic agent (341) is injected into the suprachoroidal space.

Once delivery is complete, needle (20) may be retracted by sliding actuation assembly (60) proximally relative to body (40); and cannula (30) may then be withdrawn from eye (301). It should be understood that because of the size of needle (20), the site where needle (20) penetrated through choroid (306) is self sealing, such that no further steps need be taken to seal the delivery site through choroid (306). Suture loop assembly (330) and chandelier (314) may be removed, and incision (316) in the sclera (304) may be closed using any suitable conventional techniques.

As noted above, the foregoing procedure may be carried out to treat a patient having macular degeneration. In some such instances, the therapeutic agent (341) that is delivered by needle (20) may comprise cells that are derived from postpartum umbilicus and placenta. As noted above, and by way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (20) may be used to deliver any other suitable substance or substances, in addition to or in lieu of those described in U.S. Pat. No. 7,413,734 and/or elsewhere herein. By way of example only, therapeutic agent (341) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

V. EXEMPLARY INSTRUMENT WITH MICRO-CATHETER

In some instances, it may be desirable to vary certain components or features of the instruments described herein in order to vary the technique for delivering therapeutic agent to the subretinal space of an eye. In some examples, it may further be desirable to vary certain steps or features of the surgical procedures described herein. For instance, it may be desirable to vary the surgical procedures described herein by utilizing instruments similar to instruments (10, 2010) with features configured to limit the need to cut the eye using a scalpel or other cutting instrument as described above. Instruments having the above referenced variations may be desirable for different surgical procedures, or surgical procedures similar to the procedure discussed above, to engage tissue structures having varying physical properties. While certain examples of variations are described herein, it should be understood that the instruments described herein may include any other alternative features as will be apparent to those of ordinary skill in the art in view of the teachings herein.

A. Exemplary Instrument with Manually Slid Micro-Catheter

Figure 12:
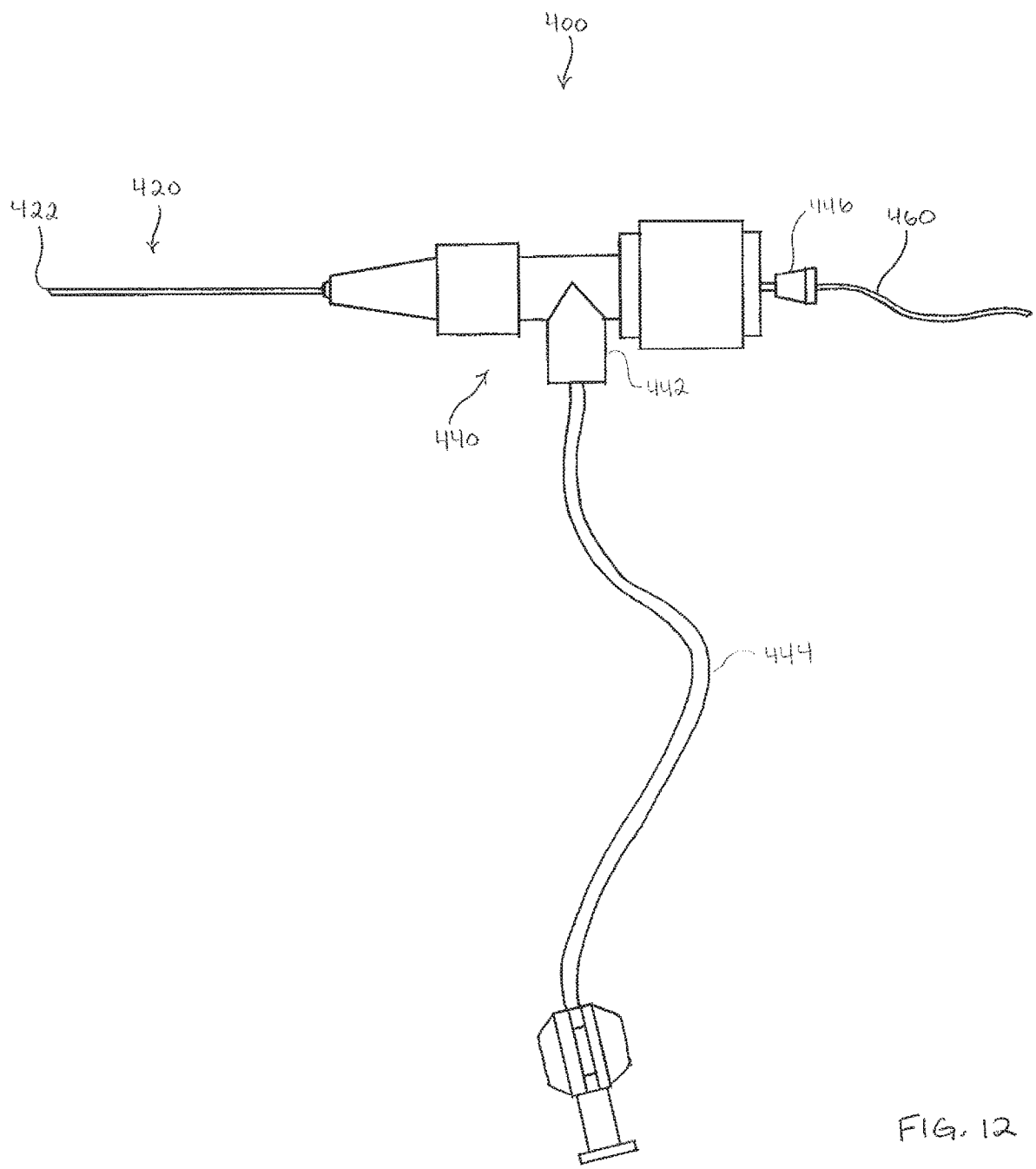
FIG. 12 depicts a side elevational view of another exemplary instrument for subretinal administration of a therapeutic agent.
Figure 13:
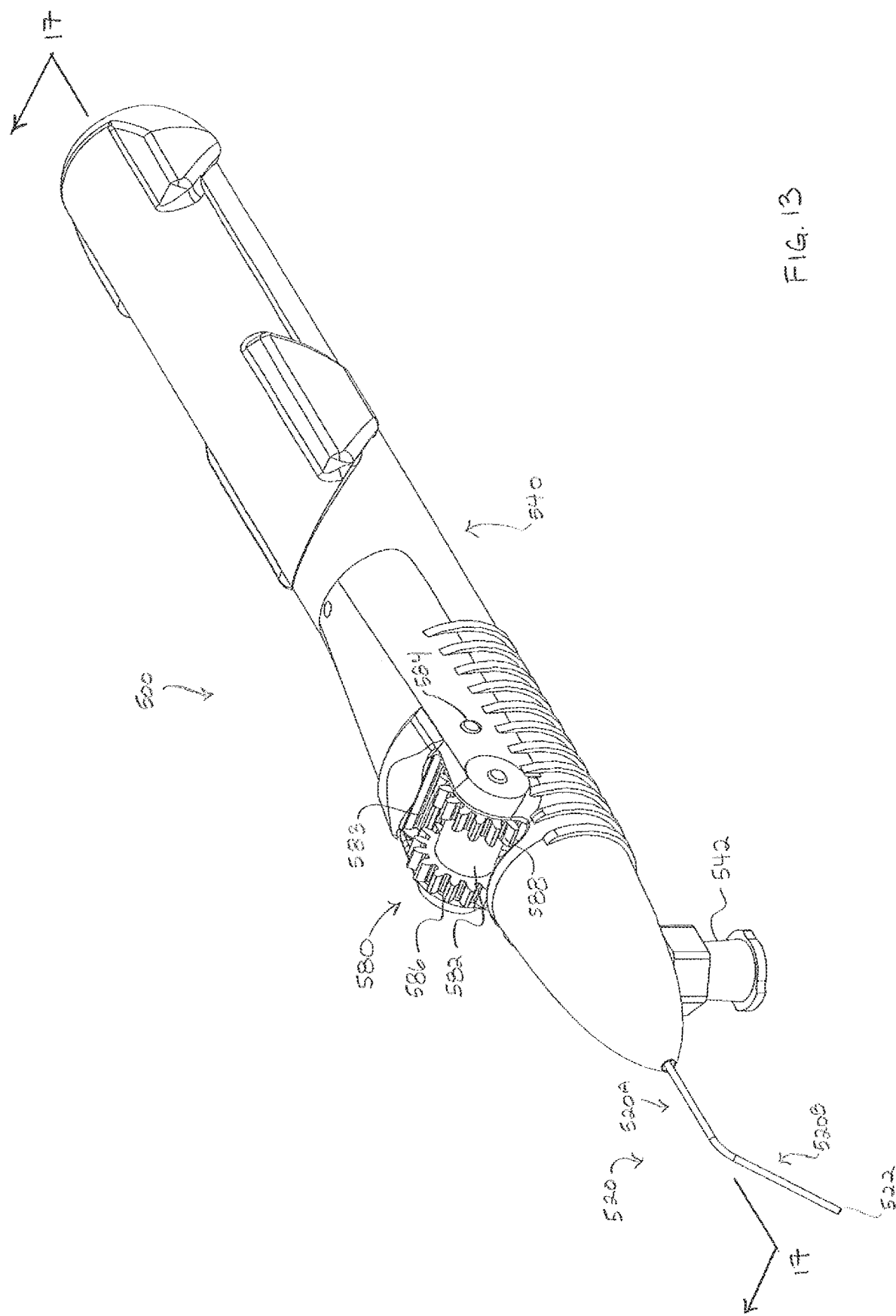
FIG. 13 depicts a perspective view of yet another exemplary instrument for subretinal administration of a therapeutic agent.
Figure 14:
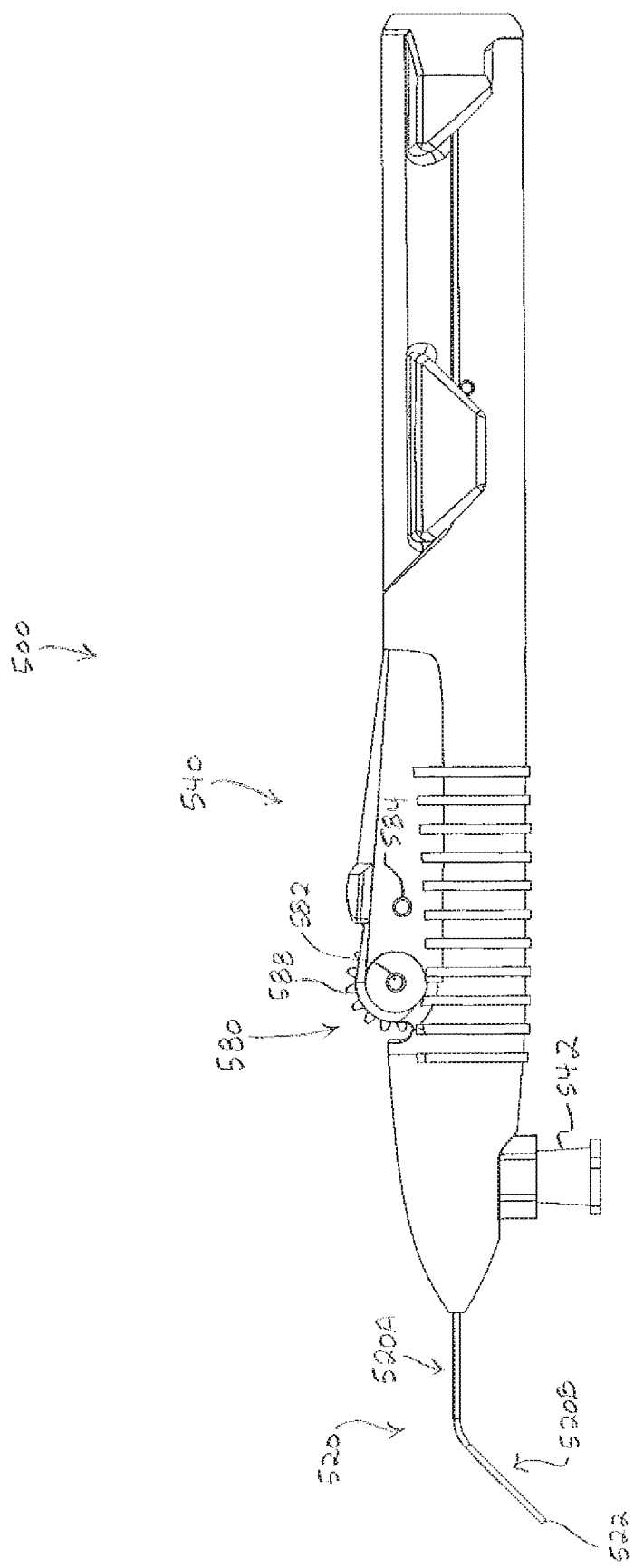
FIG. 14 depicts a side elevational view of the instrument of FIG. 13.
Figure 15:
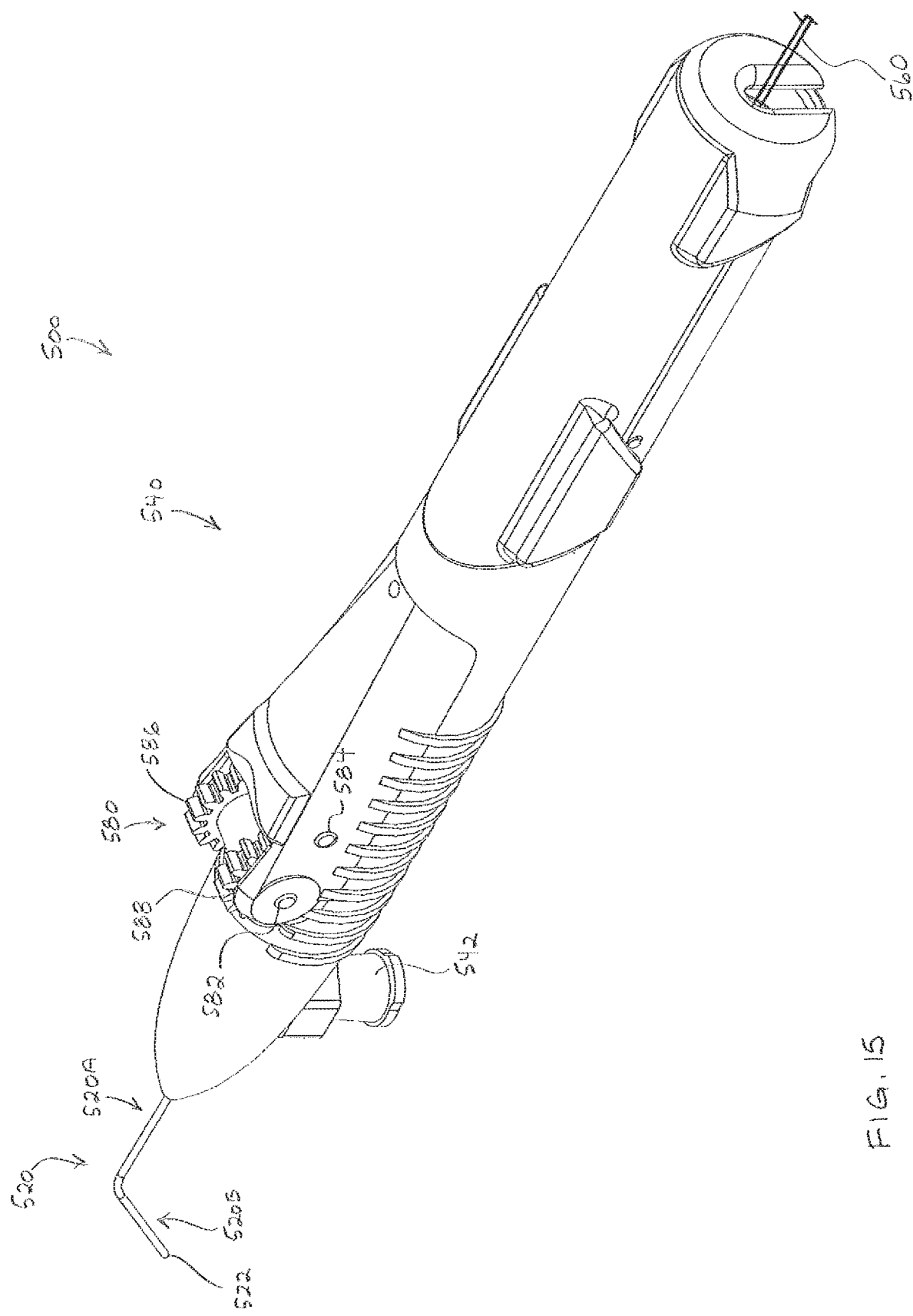
FIG. 15 depicts another perspective view of the instrument of FIG. 13.
Figure 21:
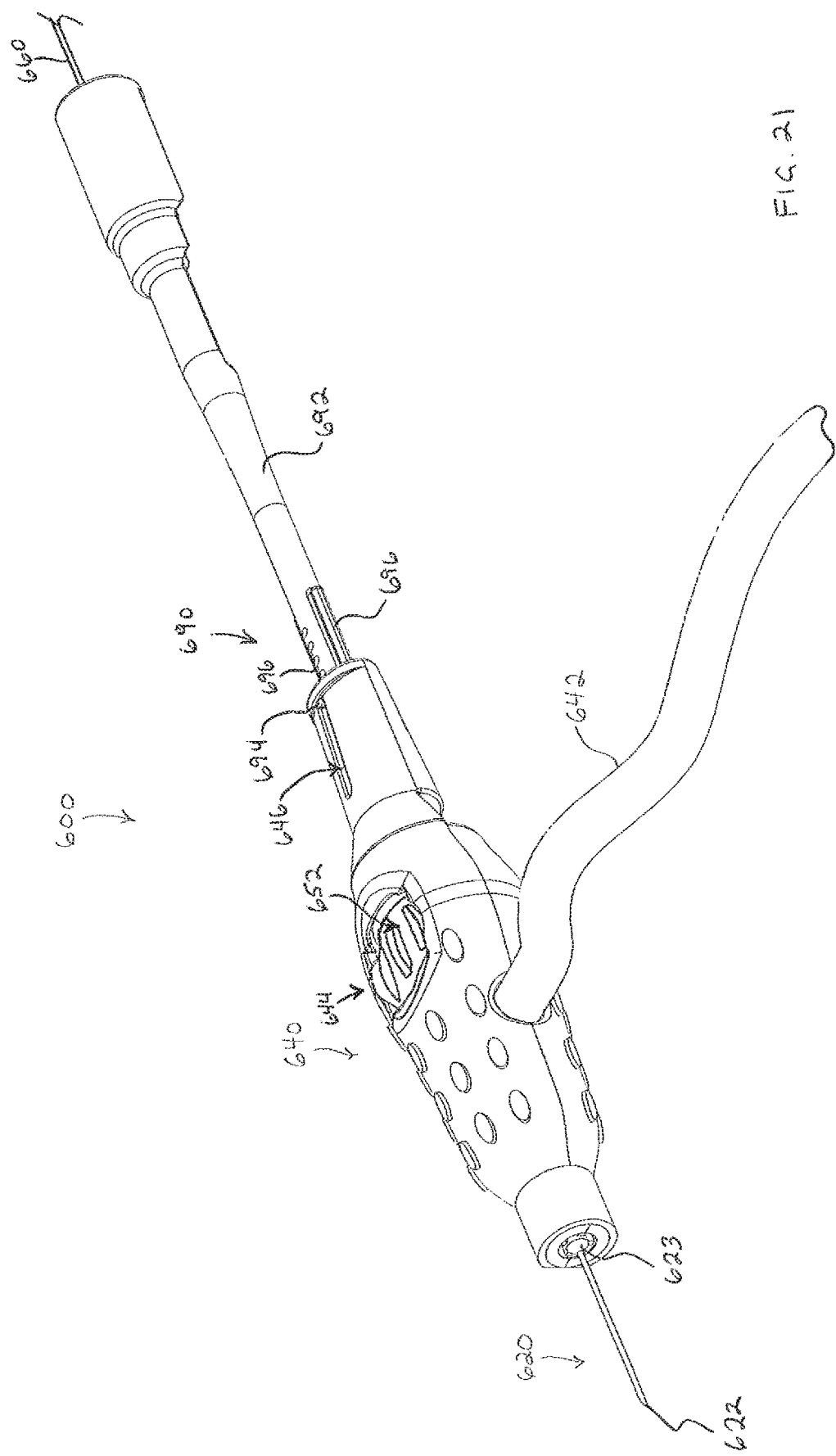
FIG. 21 depicts a perspective view of yet another exemplary instrument for subretinal administration of a therapeutic agent.
Figure 24B:
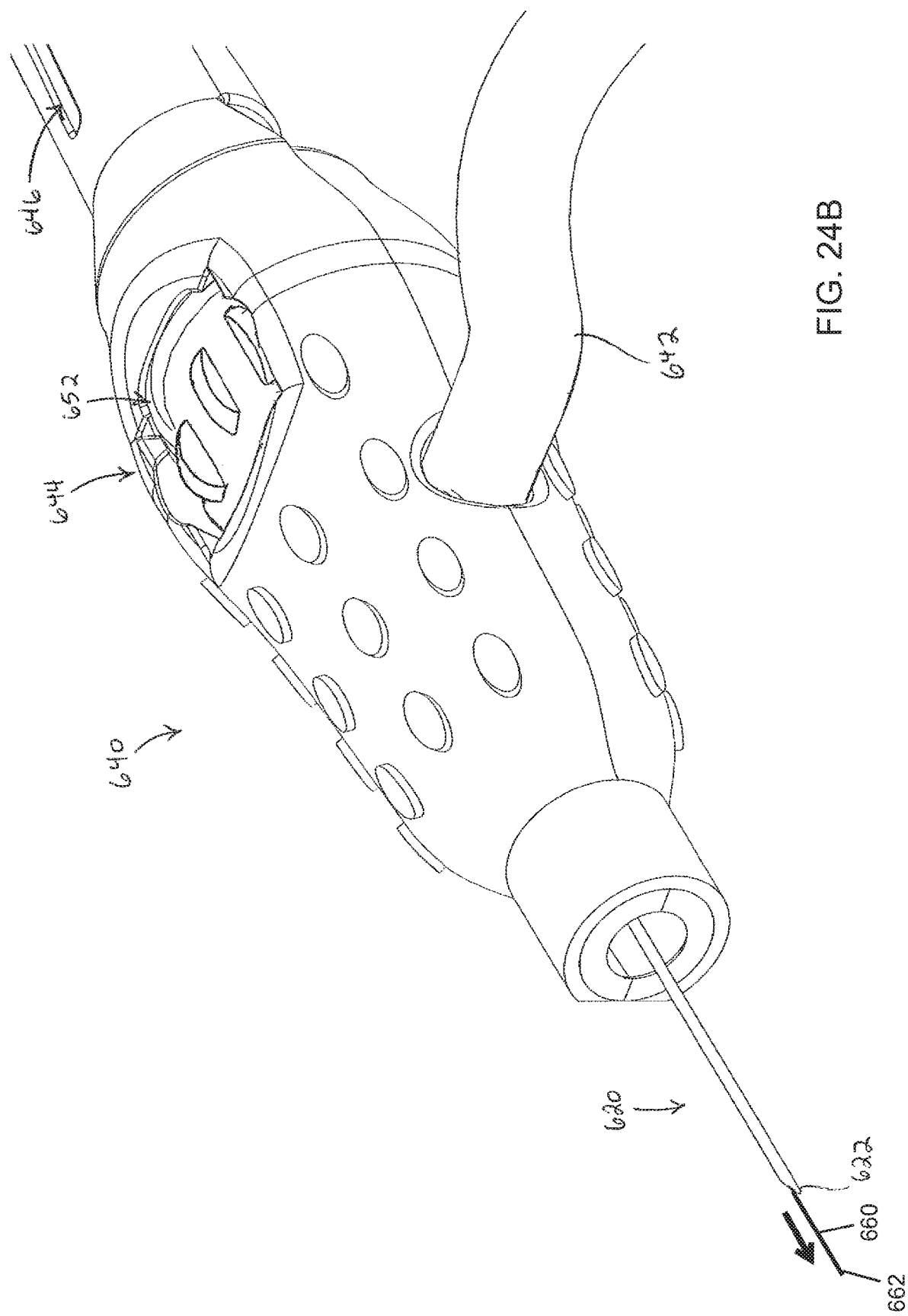
FIG. 24B depicts a detailed perspective view of the instrument of FIG. 21, with the micro-catheter advanced distally from the needle of FIG. 24A.

FIG. 12 shows an exemplary instrument (400) that is configured for use in a procedure for the subretinal administration of a therapeutic agent to an eye of a patient. Instrument (400) comprises a needle (420), a body (440), and a micro-catheter (460). Needle (420) extends distally from body (440). Needle (420) is generally configured to support micro-catheter (460), as will be described in more detail below. Also as will be described in more detail below, needle (420) has sufficient column strength to permit piercing and advancement of needle (420) through the sclera and the choroid to the subretinal space of a patient's eye without buckling. Needle (420) has a sharp distal end (422) and defines an internal lumen (not shown) extending longitudinally through needle (420). As will be described in more detail below, the lumen of needle (420) is configured to slidably receive micro-catheter (460).

Sharp distal end (422) is configured to provide for piercing and penetration of the sclera and choroid layers to enable needle (420) to be advanced through such layers to the subretinal space while not inflicting other incidental trauma to the sclera or choroid layers. Distal end (422) of the present example has a lancet configuration. In some other versions, distal end (422) has a tri-bevel configuration or any other configuration as described in U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12, 2019, the disclosure of which is incorporated by reference herein. Still other suitable forms that distal end (422) may take will be apparent to those of ordinary skill in the art in view of the teachings herein. Needle (420) of the present example comprises a stainless steel hypodermic needle that is sized to receive micro-catheter (460) while being small enough to minimize incidental trauma as needle (420) penetrates tissue structures of the patient's eye, as will be described in greater detail below. By way of example only, needle (420) may be 23 gauge, although other suitable sizes may be used.

Body (440) is generally T-shaped with an outwardly projecting fluid port (442). The particular shape of body (440) that is shown is configured to be grasped by an operator. Alternatively, body (440) may be mounted on a support device or arm for ease of positioning instrument (400), as described in U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12, 2019, the disclosure of which is incorporated by reference herein. Fluid port (442) provides fluid access to an interior of body (440). In the present example, a fluid supply line (444) is coupled with fluid port (442) and configured to provide fluid to the interior of body (440). As will be described in more detail below, needle (420) is in fluid communication with the interior of body (440) such that fluid (e.g., Healon® OVD manufactured by Abbott Medical Optics) provided via fluid supply line (444) is communicated to the distal end of needle (420) via the lumen formed within needle (420).

A proximal portion of body (440) includes a ferrule (446). Ferrule (446) provides access to the interior of body (440). Ferrule (446) is configured to slidably receive micro-catheter (460) such that micro-catheter (460) may be passed through ferrule (446) into the interior of body (440). A portion of micro-catheter (460) is exposed relative to ferrule (446) such that an operator may engage and manually translate micro-catheter (460). Ferrule (446) includes a sealing element (e.g., a wiper seal or an o-ring, etc.) (not shown), which permits translation of micro-catheter (460) within and relative to ferrule (446) while preventing inadvertent leakage of fluid from the interior of body (440). Needle (420) is configured to slidably receive micro-catheter (460). Micro-catheter (460) is thus configured to pass through ferrule (446), through the interior of body (440), and into the lumen of needle (420). Needle (420) of the present example is sized such that even with micro-catheter (460) positioned within the lumen of needle (420), fluid may nevertheless pass through needle (420) about micro-catheter (460). Micro-catheter (460) may be manually translated within and relative to needle (420). For instance, micro-catheter (460) may be translated distally relative to needle (420) to a point where micro-catheter (460) extends distally from the distal end of needle (420).

As will be described in more detail below, with needle (420) positioned such that the distal end of needle (420) is within the subretinal space, micro-catheter (460) may be advanced distally from the distal end of needle (420) between the choroid and the retina of a patient's eye to a position at the back of the patient's eye. This advancement of micro-catheter (460) is performed by an operator manually translating micro-catheter (460). Micro-catheter (460) is flexible enough to conform to specific structures and contours of the patient's eye, yet micro-catheter (460) has sufficient column strength to permit advancement of micro-catheter (460) between the choroid and the retina of a patient's eye without buckling. Needle (420) is generally configured to direct micro-catheter (460) along an exit axis that is angularly oriented obliquely relative to a longitudinal axis of needle (420). It should be understood that such an angle may be desirable to deflect micro-catheter (460) in a direction to ensure that micro-catheter (460) continues beneath the retina (308) through the subretinal space (as opposed to penetrating the retina (308)) and to prevent penetration of micro-catheter (460) into the retina (308).

As will be described in more detail below, micro-catheter (460) defines an internal lumen (not shown). With micro-catheter (460) positioned at the back of the patient's eye, the lumen of micro-catheter (460) is configured to permit the flow of fluid (e.g., a therapeutic agent) through micro-catheter (460) to the distal end of micro-catheter (460) so as to deliver the fluid to the back of the patient's eye. Once the fluid has been delivered to the back of the patient's eye, micro-catheter (460) may be drawn proximally back into the distal end of needle (420). This proximal translation of micro-catheter (460) is performed by an operator manually translating micro-catheter (460). Also as will be described in more detail below with reference to FIGS. 53B-53D, micro-catheter (460) includes an illuminating element (462) that is configured to assist in tracking or positioning of micro-catheter (460) within the patient's eye.

B. Exemplary Instrument with Gear Assembly Actuator to Drive Micro-Catheter

FIGS. 13-20B show an exemplary alternative instrument (500) that is similar to instrument (400) described above. While certain features and operabilities of instrument (500) are described below, it should be understood that, in addition to or in lieu of the following, instrument (500) may be configured and/or operable in accordance with any of the teachings of U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12, 2019, the disclosure of which is incorporated by reference herein. Like with instrument (400), instrument (500) of the present example is generally usable in the procedure described herein to deliver a therapeutic fluid subretinally to an eye of a patient. It should therefore be understood that instrument (500) may be readily used in place of instrument (400) to perform the medical procedures described herein. Like instrument (400), instrument (500) of this example comprises a needle (520), body (540), and a micro-catheter (560). Needle (520) comprises a stainless steel hypodermic needle that is substantially the same as needle (420) described above. In the present example, needle (520) and micro-catheter (560) are substantially identical to needle (420) and micro-catheter (460) described above.

Needle (520) extends distally from body (540). Needle (520) is generally configured to support micro-catheter (560), as will be described in more detail below. Also as will be described in more detail below, needle (520) has sufficient column strength to permit piercing and advancement of needle (520) through the sclera and the choroid to the subretinal space of a patient's eye without buckling. Needle (520) includes a generally straight proximal portion (520A) and a bent distal portion (520B). Bent distal portion (520B) of the present example is bent to improve the ergonomics of instrument (500), enabling the operator to insert needle (520) at an appropriate angle relative to the eye without having to hold instrument at an awkward angle relative to the operator. It should be understood that such an angle may be desirable to deflect micro-catheter (560) in a direction to ensure that micro-catheter (560) continues beneath the retina (308) through the subretinal space and to prevent penetration of micro-catheter (560) through the retina (308).

As best seen in FIGS. 20A-20B, needle (520) has a sharp distal end (522) and defines an internal lumen (524) extending through needle (520). As will be described in more detail below, lumen (524) of needle (520) is configured to slidably receive micro-catheter (560). Sharp distal end (522) is configured to provide for piercing of the sclera and choroid layers to enable needle (520) to be advanced through such layers to the subretinal space while not inflicting other incidental trauma to the sclera or choroid layers. Distal end (522) of the present example has a lancet configuration. In some other versions, distal end (522) has a tri-bevel configuration or any other configuration as described in U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12, 2019, the disclosure of which is incorporated by reference herein. Still other suitable forms that distal end (522) may take will be apparent to those of ordinary skill in the art in view of the teachings herein. Needle (520) of the present example comprises a stainless steel hypodermic needle that is sized to receive micro-catheter (560) while being small enough to minimize incidental trauma as needle (520) penetrates tissue structures of the patient's eye, as will be described in greater detail below. By way of example only, needle (520) may be 23 gauge, although other suitable sizes may be used.

Body (540) is generally elongate shaped and includes an outwardly projecting fluid port (542) extending from a distal portion of body (540). The particular shape of body (540) that is shown is configured to be grasped by an operator. Alternatively, body (540) may be mounted on a support device or arm for ease of positioning instrument (500), as described in U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12, 2019, the disclosure of which is incorporated by reference herein. As best seen in FIGS. 17 and 20A-20B, fluid port (542) provides fluid access to an interior (541) of body (540). In the present example, a fluid supply line (not shown) may be coupled with fluid port (542) and configured to provide fluid to the interior (541) of body (540). As will be described in more detail below, needle (520) is in fluid communication with the interior (541) of body (540) such that fluid (e.g., Healon® OVD manufactured by Abbott Medical Optics) provided via the fluid supply line is communicated to the distal end of needle (520) via lumen (524) formed within needle (520).

The primary difference between instrument (400) and instrument (500) is that instrument (500) includes a gear assembly (580) that is configured to drive translation of micro-catheter (560) relative to needle (520). Body (540) includes a sled (550) that is slidably disposed within a cylindrical bore (546) formed in a proximal portion of body (540). Sled (550) is operable to translate longitudinally within cylindrical bore (546) between a proximal longitudinal position (FIG. 20A) and a distal longitudinal position (FIG. 20B). Body (540) includes a pin (548) positioned within an elongate slot (552) formed in a bottom surface of sled (550) (FIG. 19). Pin (548) is operable to limit longitudinal translation of sled (550) based upon the longitudinal length of slot (552).

Gear assembly (580) includes a pair of rotatable members (582, 584). Rotatable member (582) includes a pair of gears (586, 588) positioned at opposite ends of rotatable member (582). Rotatable member (582) is partially exposed relative to body (540) such that an operator may engage rotatable member (582) using his or her fingers or thumb to thereby cause rotation of rotatable member (582). Rotatable member (584) includes an elongate gear (583), which extends substantially the length of rotatable member (584). Teeth of gears (586, 588) of rotatable member (582) engage teeth of gear (583) of rotatable member (584) such that rotation of rotatable member (582) causes concurrent rotation of rotatable member (584). Rotatable member (582) is rotatable about an axis that is perpendicular to the longitudinal axis of body (540).

As best seen in FIG. 18, sled (550) includes a plurality of gear teeth (558) extending longitudinally along a length of sled (550). Teeth (558) of sled (550) engage teeth of gear (583) of rotatable member (584) in a rack and pinion relationship. Thus, rotation of rotatable member (584) causes longitudinal translation of sled (550) between the proximal longitudinal position (FIG. 20A) and the distal longitudinal position (FIG. 20B). It should be appreciated that rotation of rotatable member (582) in a first direction will cause distal longitudinal translation of sled (550) relative to body (540) and that rotation of rotatable member (582) in a second direction will cause proximal longitudinal translation of sled (550) relative to body (540).

As best seen in FIG. 17, micro-catheter (560) is coupled with sled (550) such that translation of sled (550) causes concurrent translation of micro-catheter (560). Micro-catheter (560) extends distally through a bore (554) formed in sled (550) and extends distally therefrom. It should therefore be appreciated that rotation of rotatable member (582) in a first direction will cause distal longitudinal translation of micro-catheter (560) relative to needle (520) and that rotation of rotatable member (582) in a second direction will cause proximal longitudinal translation of micro-catheter (560) relative to needle (520).

Micro-catheter (560) passes through a bore (549) formed in body (540), through the interior (541) of body (540), into lumen (524) of needle (520). Bore (549) of body (540) may include a sealing element (e.g., a wiper seal, an o-ring, etc.) (not shown) that permits translation of micro-catheter (560) within and relative to bore (549) while preventing inadvertent leakage of fluid from the interior (541) of body (540). Needle (520) of the present example is sized such that even with micro-catheter (560) positioned within the lumen of needle (520), fluid may nevertheless pass through needle (520) about micro-catheter (560). Micro-catheter (560) may be translated within and relative to needle (520) via translation of sled (550). For instance, micro-catheter (560) may be translated distally relative to needle (520) to a point where micro-catheter (560) extends distally from the distal end of needle (520).

As will be described in more detail below, with needle (520) positioned such that the distal end of needle (520) is within the subretinal space, micro-catheter (560) may be advanced distally from the distal end of needle (520) between the choroid and the retina of a patient's eye to a position at the back of the patient's eye. This advancement of micro-catheter (560) is performed by rotation of rotatable member (582) in a first direction shown in FIGS. 20A and 20B. Micro-catheter (560) is flexible enough to conform to specific structures and contours of the patient's eye, yet micro-catheter (560) has sufficient column strength to permit advancement of micro-catheter (560) between the choroid and the retina of a patient's eye without buckling. Needle (520) is generally configured to direct micro-catheter (560) along an exit axis that is angularly oriented obliquely relative to a longitudinal axis of needle (520). It should be understood that such an angle may be desirable to deflect micro-catheter (560) in a direction to ensure that microcatheter (560) continues beneath the retina (308) through the subretinal space and to prevent penetration of micro-catheter (560) through the retina (308).

As will be described in more detail below, micro-catheter (560) defines an internal lumen. With micro-catheter (560) positioned at the back of the patient's eye, the lumen of micro-catheter (560) is configured to permit the flow of fluid (e.g., a therapeutic agent) through micro-catheter (560) to the distal end of micro-catheter (560) so as to deliver the fluid to the back of the patient's eye. Once the fluid has been delivered to the back of the patient's eye, micro-catheter (560) may be drawn proximally back into the distal end of needle (520). This proximal translation of micro-catheter (560) is performed by rotation of rotatable member (582) in a second direction. Also as will be described in more detail below, micro-catheter (560) may include an illuminating element that is configured to assist in tracking or positioning of micro-catheter (560) within the patient's eye.

C. Exemplary Instrument with Threaded Assembly Actuator to Drive Micro-Catheter

FIGS. 21-27B show an exemplary alternative instrument (600) that is similar to instruments (400, 500) described above. While certain features and operabilities of instrument (600) are described below, it should be understood that, in addition to or in lieu of the following, instrument (600) may be configured and/or operable in accordance with any of the teachings of U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12, 2019, the disclosure of which is incorporated by reference herein. Like with instruments (400, 500), instrument (600) of the present example is generally usable in the procedure described herein to deliver a therapeutic fluid subretinally to an eye of a patient. It should therefore be understood that instrument (600) may be readily used in place of instruments (400, 500) to perform the medical procedures described herein. Like instruments (400, 500), instrument (600) of this example comprises a needle (620), body (640), and a micro-catheter (660). Needle (620) comprises a stainless steel hypodermic needle that is substantially the same as needles (420, 520) described above. In the present example, needle (620) and micro-catheter (660) are substantially identical to needles (420, 520) and micro-catheters (460, 560) described above.

Needle (620) extends distally from body (640). Needle (620) is generally configured to support micro-catheter (660), as will be described in more detail below. Also as will be described in more detail below, needle (620) has sufficient column strength to permit piercing and advancement of needle (620) through the sclera and the choroid to the subretinal space of a patient's eye without buckling. Needle (620) has a sharp distal end (622) and defines an internal lumen (624) extending through needle (620). As will be described in more detail below, lumen (624) of needle (620) is configured to slidably receive micro-catheter (660). Sharp distal end (622) is configured to provide for piercing of the sclera and choroid layers to enable needle (620) to be advanced through such layers to the subretinal space while not inflicting other incidental trauma to the sclera or choroid layers. Distal end (622) of the present example has a lancet configuration. In some other versions, distal end (622) has a tri-bevel configuration or any other configuration as described in U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12, 2019, the disclosure of which is incorporated by reference herein. Still other suitable forms that distal end (622) may take will be apparent to those of ordinary skill in the art in view of the teachings herein. Needle (620) of the present example comprises a stainless steel hypodermic needle that is sized to receive micro-catheter (660) while being small enough to minimize incidental trauma as needle (620) penetrates tissue structures of the patient's eye, as will be described in greater detail below. By way of example only, needle (620) may be 23 gauge, although other suitable sizes may be used.

Body (640) is generally elongate shaped and includes an outwardly extending fluid supply line (642). The particular shape of body (640) that is shown is configured to be grasped by an operator. Alternatively, body (640) may be mounted on a support device or arm for ease of positioning instrument (600), as described in U.S. patent application Ser. No. 14/619,256, entitled "Method and Apparatus for Suprachoroidal Administration of Therapeutic Agent," filed Feb. 11, 2015, issued as U.S. Pat. No. 10,226,379 on Mar. 12 2019, the disclosure of which is incorporated by reference herein.

Figure 25:
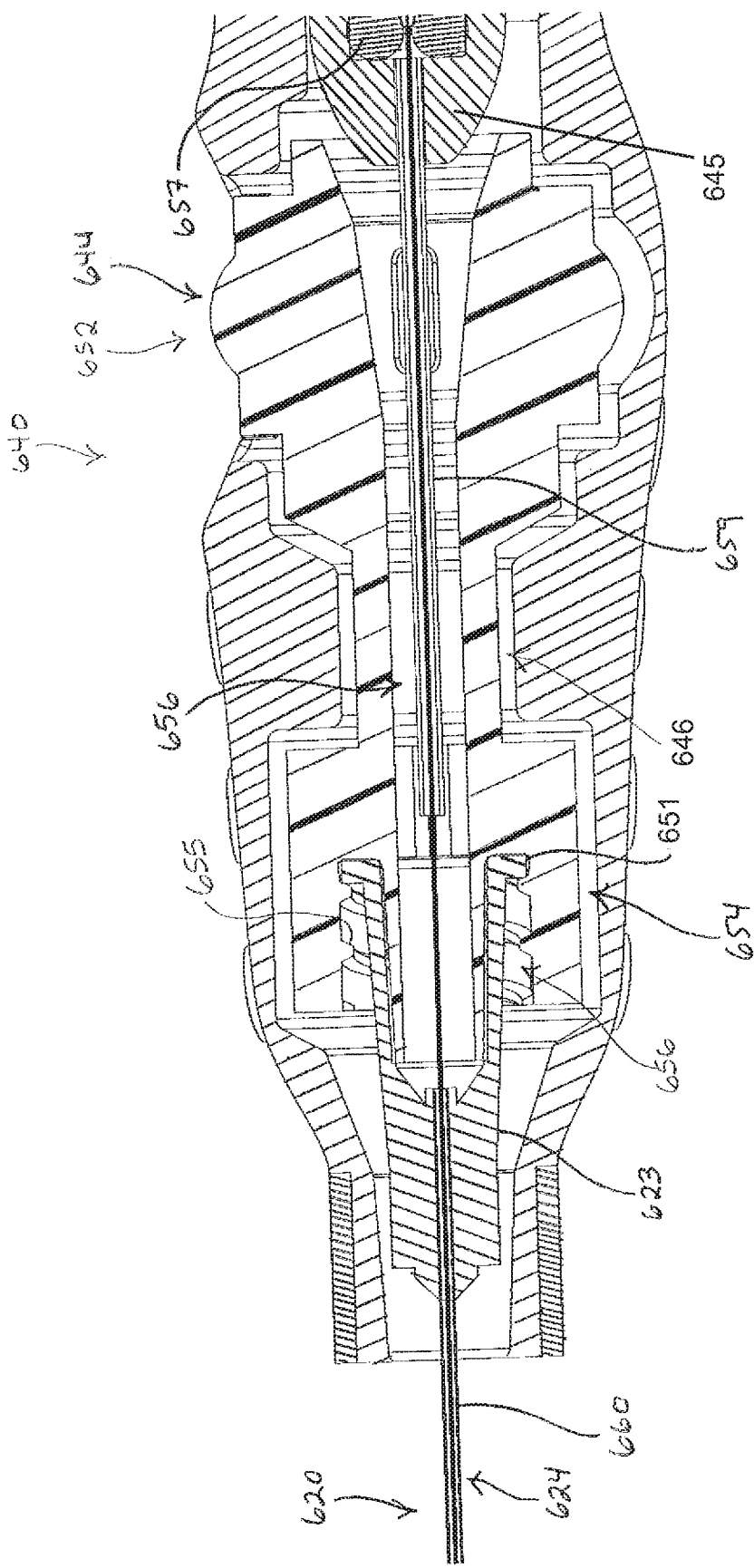
FIG. 25 depicts a detailed cross-sectional side view of the instrument of FIG. 21.

The primary difference between instruments (400, 500) and instrument (600) is that instrument (600) includes a dumbbell-shaped rotatable member (652) that is operable to control a Tuohy-Borst valve; and a plunger assembly (690) that is configured to cause translation of micro-catheter (660). As shown in FIG. 25, rotatable member (652) is rotatably disposed within a similarly shaped bore (646) formed in body (640). Rotatable member (652) is operable to rotate within bore (646). A proximal portion of rotatable member (652) is exposed relative to body (640) via an opening (644) formed in a top surface of body (640) such that an operator may engage rotatable member (652) using his or her fingers or thumb to thereby cause rotation of rotatable member (652). A distal portion (654) of rotatable member (652) includes interior threading (655) formed in a cylindrical bore (656) of distal portion (654). A proximal end of needle (620) is coupled with a conical hub (623), which includes an outwardly extending flange (651). Flange (651) is coupled with threading (655) to form a luer fitting, thereby fixedly securing needle (620) relative to rotatable member (652) in a fluid tight manner. Of course, needle (620) may be secured to rotatable member (652) in any other suitable fashion.

A tube (659) extends through cylindrical bore (656) of rotatable member (650) ante terminates in a ferrule member (645), which includes an internal seal (657) in the form of an o-ring. Seal (657) permits translation of micro-catheter (660) within and relative to tube (659) while selectively preventing inadvertent leakage of fluid from the interior of tube (659). In particular, rotatable member (652), ferrule member (645), and seal (657) cooperate to form a Tuohy-Borst valve in a manner as will be apparent to those of ordinary skill in the art in view of the teachings herein. That is, rotatable member (652) is operable to cinch down on the assembly of tube (659), ferrule member (645), and seal (657) to thereby prevent fluid communication to/from the interior of tube (659) via the proximal end of the assembly of tube (659), ferrule member (645), and seal (657).

Rotatable member (652) is rotatable relative to body (640). Since needle (620) is fixedly secured to rotatable member (652), needle (620) also thus rotatable relative to body (640). In other words, an operator may rotate rotatable member (652) relative to body (640) to thereby rotate needle (620) relative to body (640). Such rotation of needle may be desirable in order to position distal end (622) at a desired angular position about the longitudinal axis of needle (620) relative to the eye of the patient. In addition or in the alternative, an operator may wish to rotate needle (620) relative to body (640) while driving needle (620) through the sclera (304), as such rotation of needle (620) may reduce the longitudinal force required to penetrate the sclera (304) with needle (620).

Fluid supply line (642) provides fluid access to cylindrical bore (656) of rotatable member (652). As will be described in more detail below, needle (620) is in fluid communication with cylindrical bore (656) of rotatable member (652) via hub (623) such that fluid (e.g., Healon® OVD manufactured by Abbott Medical Optics) provided via fluid supply line (642) is communicated to the distal end of needle (620) via lumen (624) formed within needle (620).

Plunger assembly (690) includes a plunger (692) that is slidably disposed within a proximal portion of body (640). Plunger (692) is operable to translate longitudinally relative to body (640) between a proximal longitudinal position (FIG. 26A) and a distal longitudinal position (FIG. 26B). Plunger (692) includes a pin (694) positioned within an elongate slot (646) formed in a top surface of body (640). Pin (694) is operable to limit longitudinal translation of plunger (692) based upon the longitudinal length of slot (646). As best seen in FIG. 23, plunger (692) includes a pair of elongate projections (696) that are disposed on opposite sides of and extending from an exterior surface of plunger (692). Projections (696) are slidably disposed within a pair of mating elongate slots (648) that are formed in an interior surface of body (640) so as to prevent rotation of plunger (692) while permitting translation of plunger (692) relative to body (640).

Figure 27A:
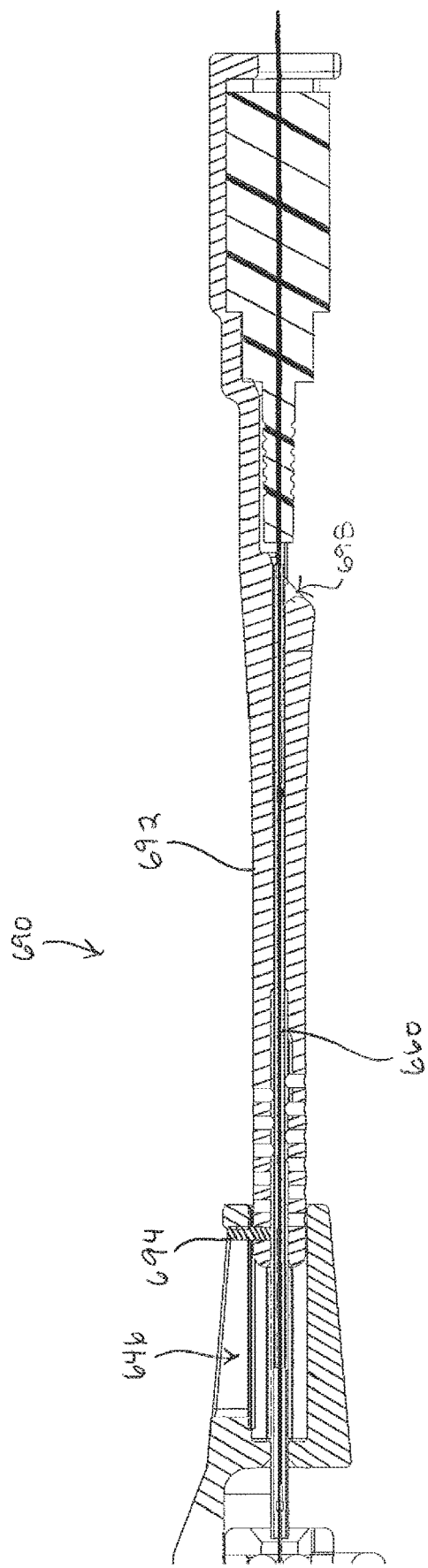
FIG. 27A depicts a detailed cross-sectional side view of the instrument of FIG. 21, with the catheter actuator of FIG. 26A in the proximal longitudinal position of FIG. 26A.
Figure 30:
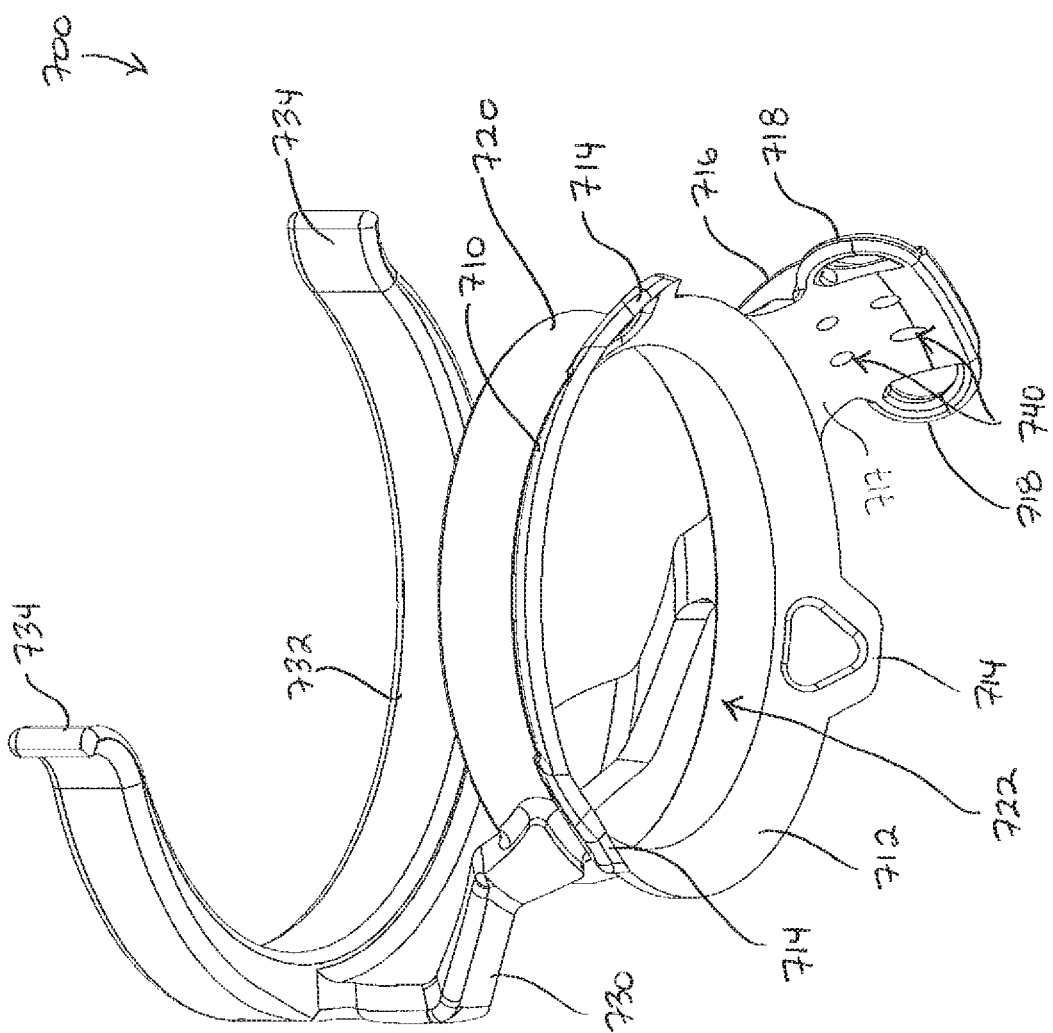
FIG. 30 depicts yet another perspective view of the guidance device of FIG. 28.
Figure 31:
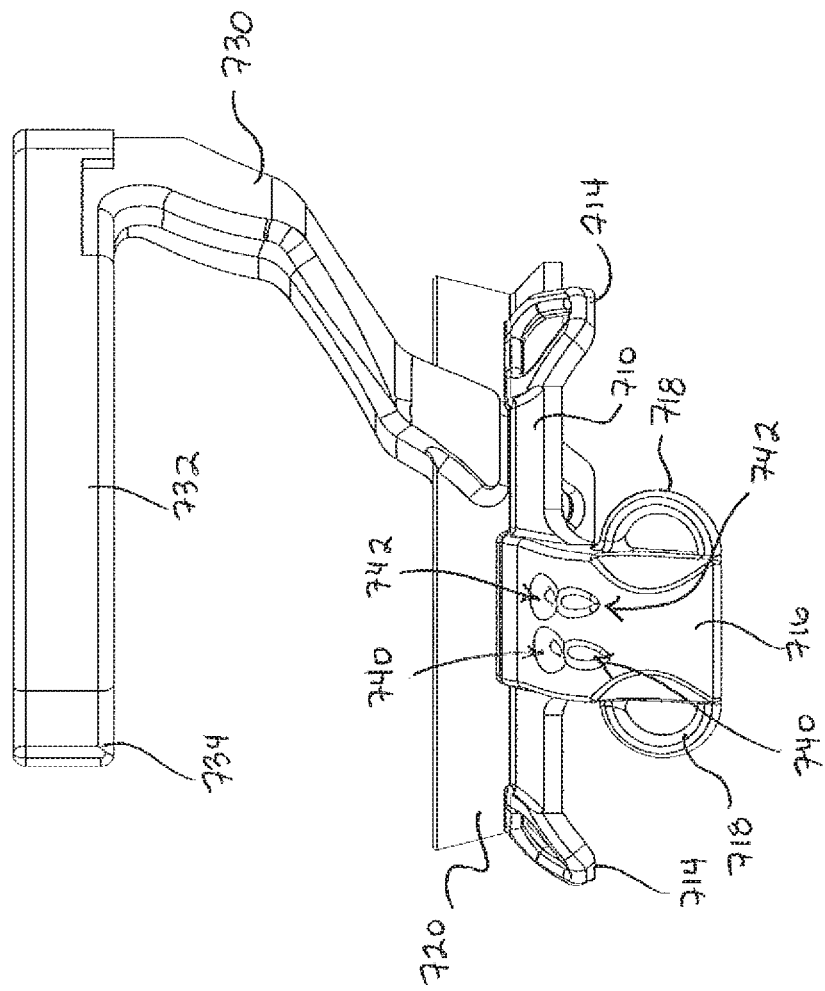
FIG. 31 depicts a side elevational view of the guidance device of FIG. 28.
Figure 32:
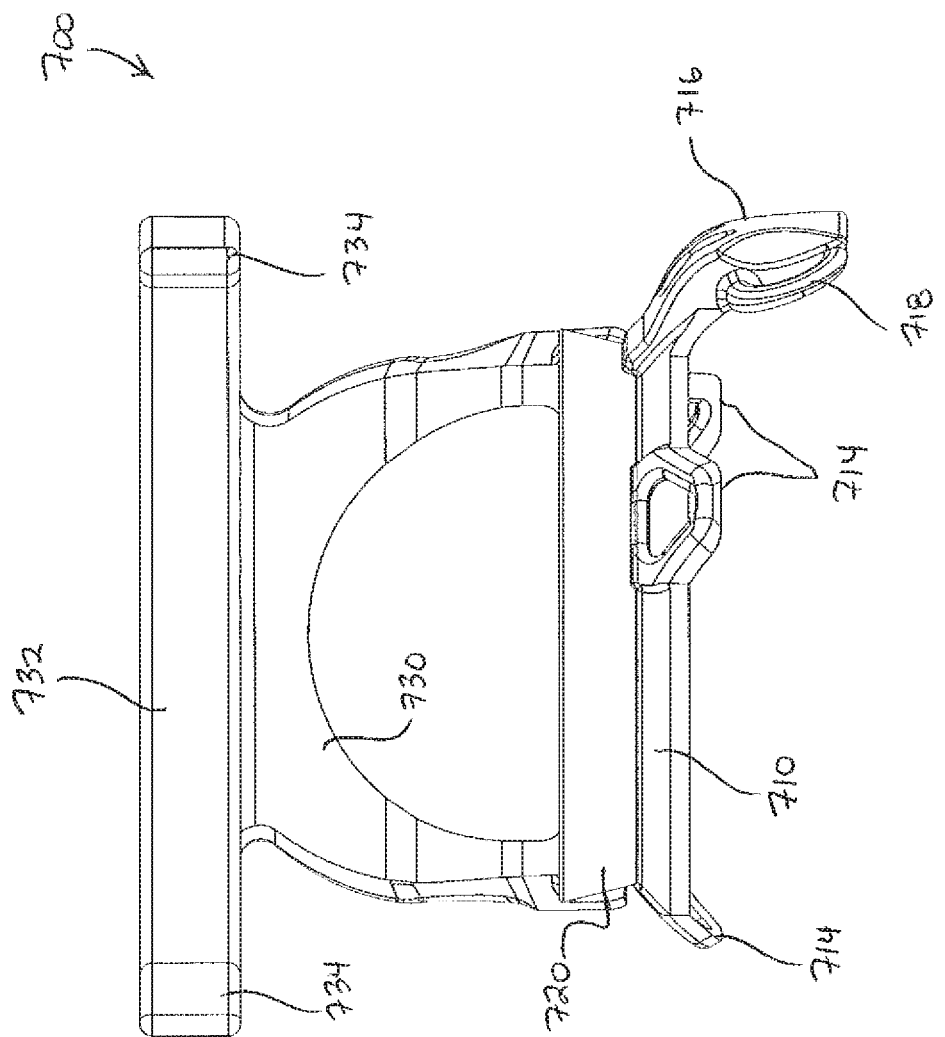
FIG. 32 depicts another side elevational view of the guidance device of FIG. 28.

As best seen in FIGS. 27A and 27B, micro-catheter (660) is coupled with plunger (692) such that translation of plunger (692) relative to body (640) causes concurrent translation of micro-catheter (660) relative to body (640). Micro-catheter (660) extends distally through a bore (698) formed in plunger (692) and extends distally therefrom. Micro-catheter (660) then passes through tube (659) and into lumen (624) of needle (620). Seal (657) permits translation of micro-catheter (660) within and relative to tube (659) while preventing inadvertent leakage of fluid from the interior of tube (659).

Needle (620) of the present example is sized such that even with micro-catheter (660) positioned within lumen (624) of needle (620), fluid may nevertheless pass through needle (620) about micro-catheter (660). Micro-catheter (660) may be translated within and relative to needle (620) via translation of plunger (692). For instance, micro-catheter (660) may be translated distally relative to needle (620) to a point where micro-catheter (660) extends distally from the distal end of needle (620).

As will be described in more detail below, with needle (620) inserted into the eye to a position such that the distal end (622) of needle (620) is within the subretinal space, micro-catheter (660) may be advanced distally from the distal end (622) of needle (620) between the choroid (306) and the retina (308) of a patient's eye to a position at the back of the patient's eye. The insertion of needle (620) is performed by advancing the entire instrument (600) distally; while the advancement of micro-catheter (660) is performed by distal translation of plunger (692) relative to body (640). Micro-catheter (660) is flexible enough to conform to specific structures and contours of the patient's eye, yet micro-catheter (660) has sufficient column strength to permit advancement of micro-catheter (660) between the choroid and the retina of a patient's eye without buckling. Needle (620) is generally configured to direct micro-catheter (660) along an exit axis that is angularly oriented obliquely relative to a longitudinal axis of needle (620). It should be understood that such an angle may be desirable to deflect micro-catheter (660) in a direction to ensure that micro-catheter (660) continues beneath the retina (308) through the subretinal space (as opposed to penetrating the retina (308)) and to minimize penetration of micro-catheter (660) into the retina (308).

As also will be described in more detail below, micro-catheter (660) defines an internal lumen. With micro-catheter (660) positioned at the back of the patient's eye, the lumen of micro-catheter (660) is configured to permit the flow of fluid (e.g., a therapeutic agent) through micro-catheter (660) to the distal end of micro-catheter (660) so as to deliver the fluid to the back of the patient's eye. Once the fluid has been delivered to the back of the patient's eye, micro-catheter (660) may be drawn proximally back into the distal end of needle (620). This proximal translation of micro-catheter (660) is performed by proximal translation of plunger (692). Needle (620) is then withdrawn from within the patient's eye by pulling the entire instrument (600) proximally. As will also be described in more detail below, micro-catheter (660) may include an illuminating element that is configured to assist in tracking or positioning of micro-catheter (660) within the patient's eye.

D. Exemplary Needle Guidance Devices

In some instances, it may be desirable to provide guidance devices that are operable to assist an operator in properly aligning needle (420, 520, 620) of instrument (400, 500, 600) relative to a patient's eye (301). For instance, such guidance devices may be configured to guide needle (420, 520, 620) into a patient's eye (301) along a path that is tangential to the retina (308), such that upon penetration of the patient's eye (301), needle (420, 520, 620) advances along a path such that a distal end of needle (420, 520, 620) advances through the sclera (304) and the choroid (306) to the subretinal space of the eye (301). Such guidance devices may come in different sizes and dimensions and may provided for different paths of advancement to accommodate the anatomical differences in each patient's eyes (301). While certain examples of variations are described herein, it should be understood that the instruments described herein may include any other alternative features as will be apparent to those of ordinary skill in the art in view of the teachings herein.

Figure 37:
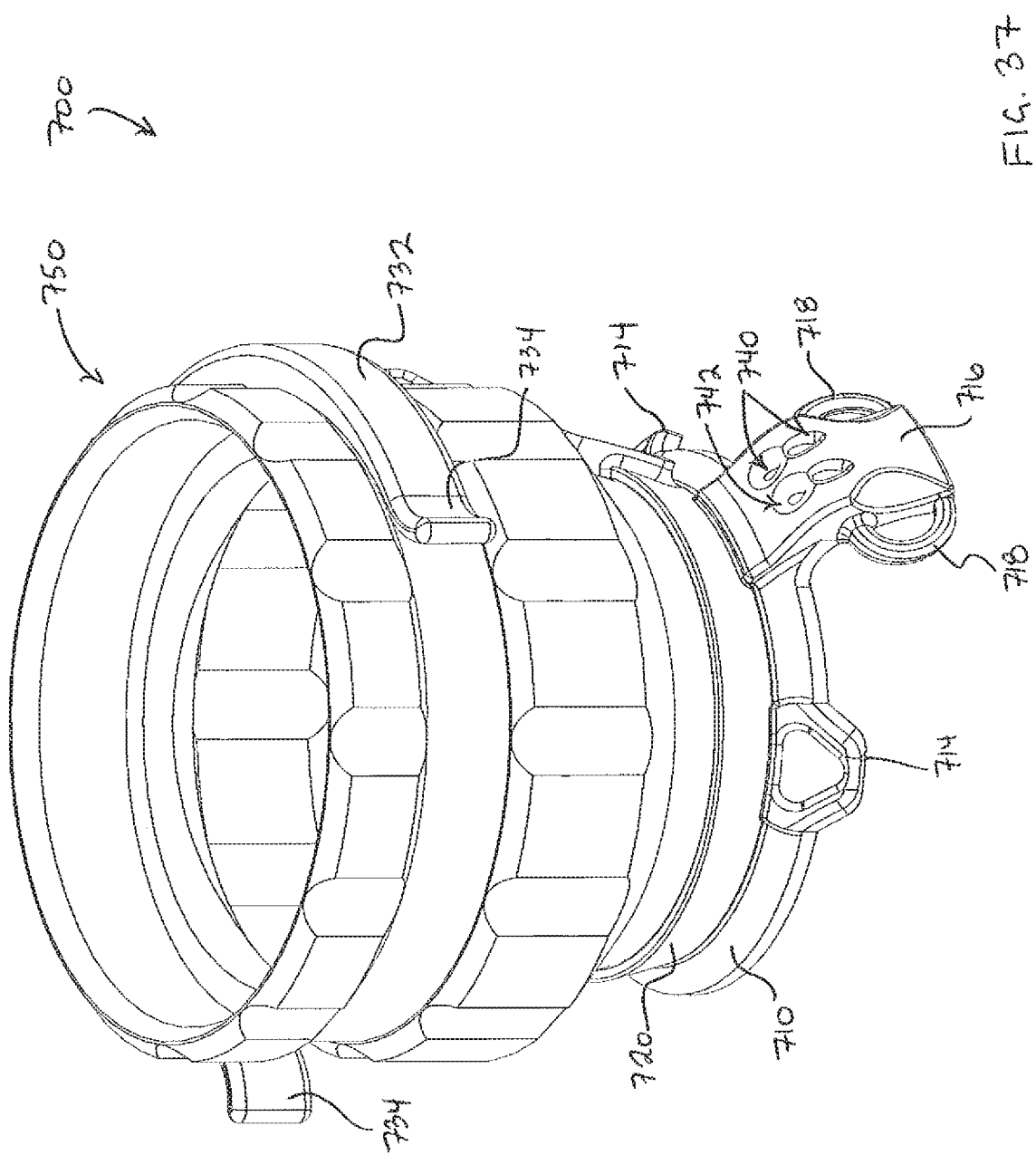
FIG. 37 depicts a perspective view of the guidance device of FIG. 28 with a viewing lens coupled within the guidance device.
Figure 38:
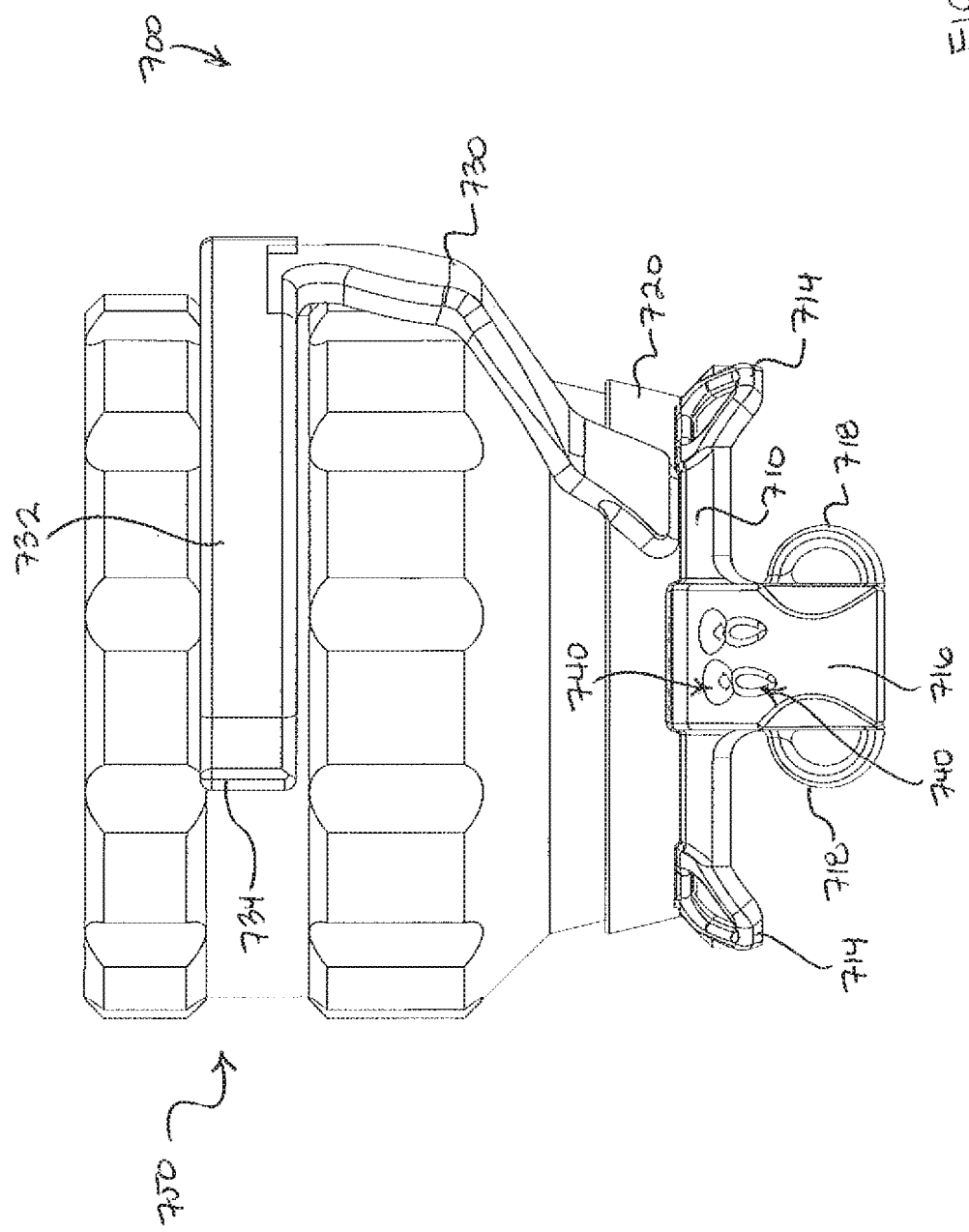
FIG. 38 depicts a side elevational view of the guidance device of FIG. 28 with the viewing lens of FIG. 37 coupled within the guidance device.
Figure 39:
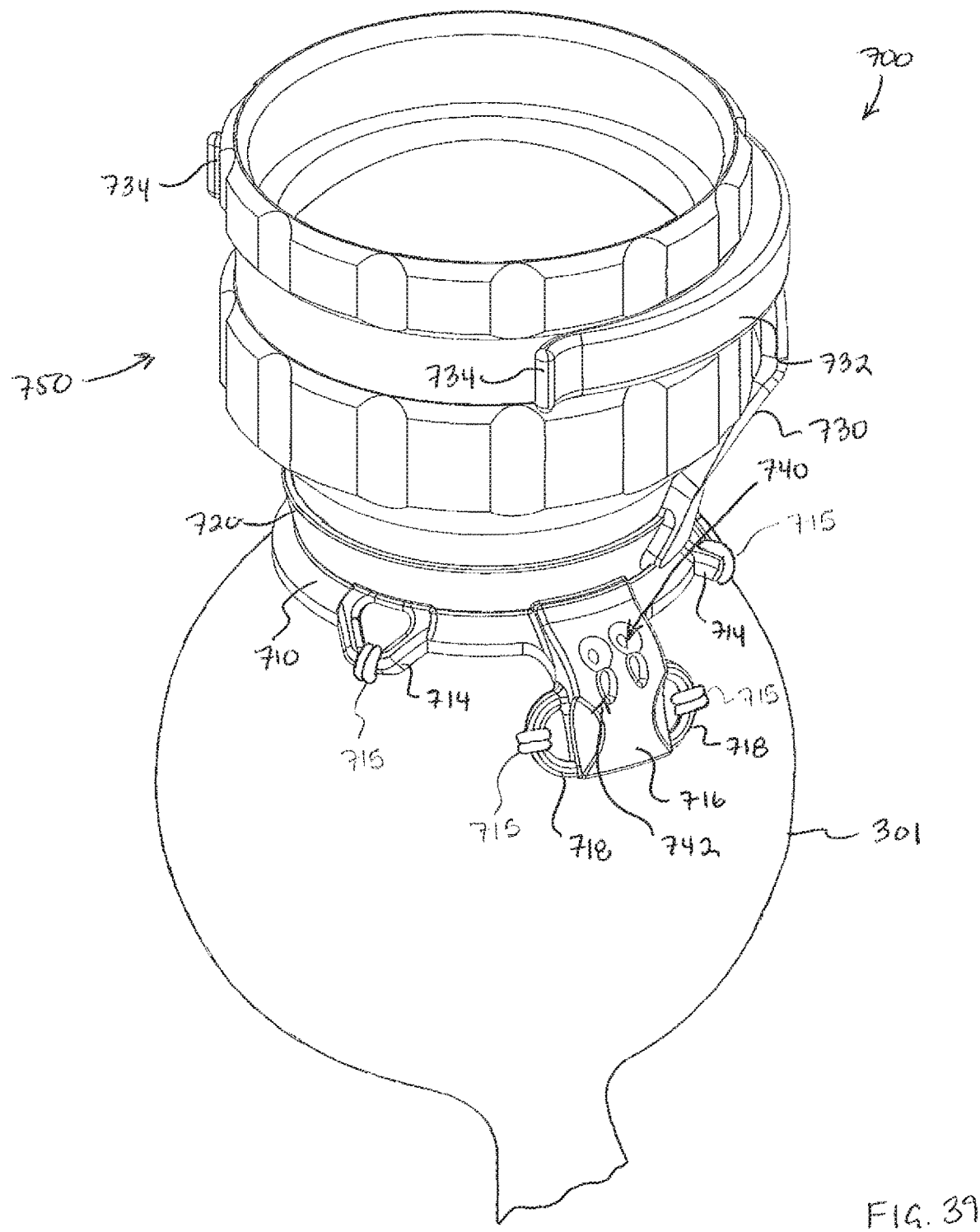
FIG. 39 depicts a perspective view of the guidance device of FIG. 28 attached to an eye, and with the viewing lens of FIG. 37 coupled within the guidance device.
Figure 40:
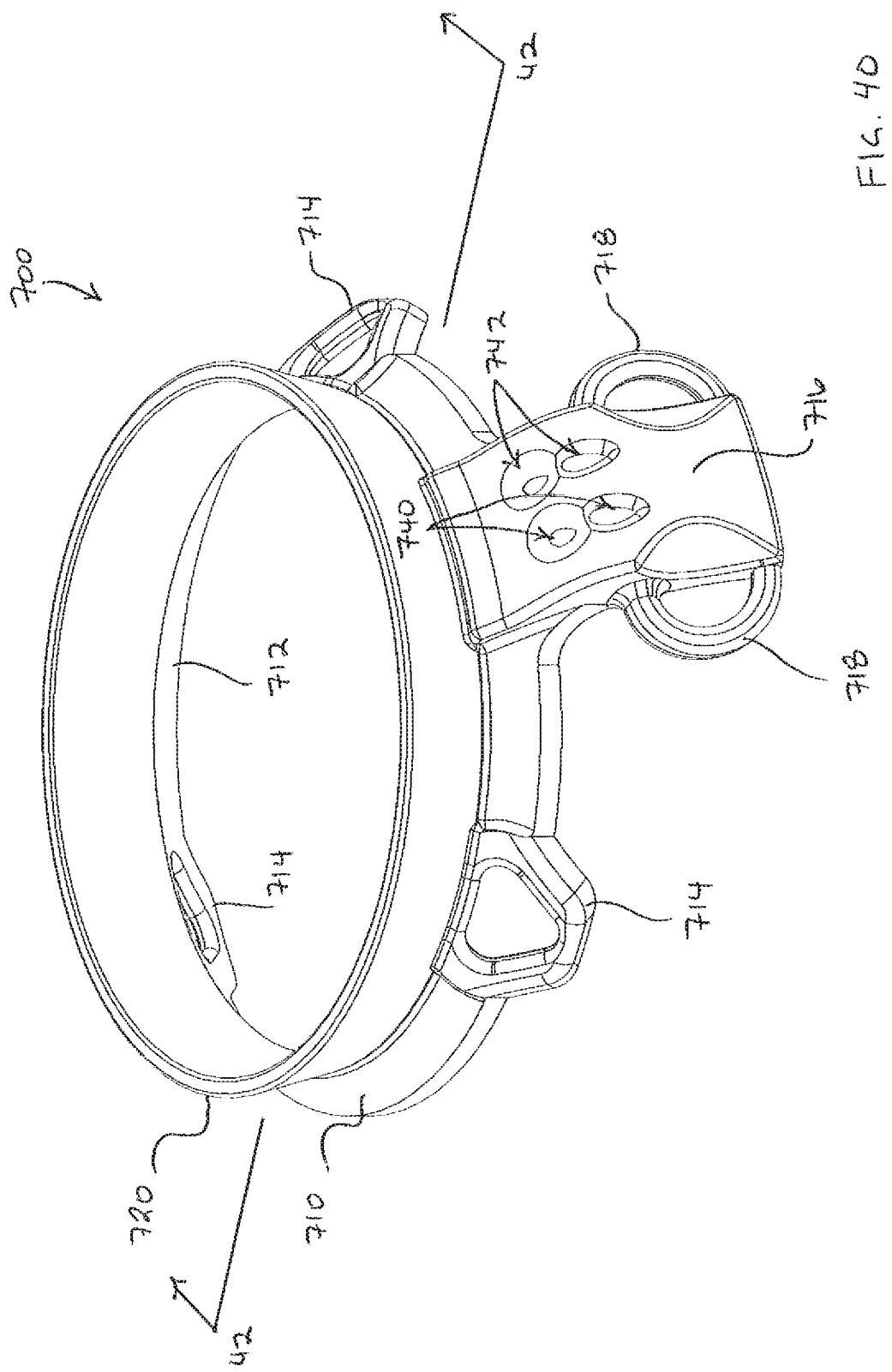
FIG. 40 depicts a perspective view of another exemplary guidance device.
Figure 41:
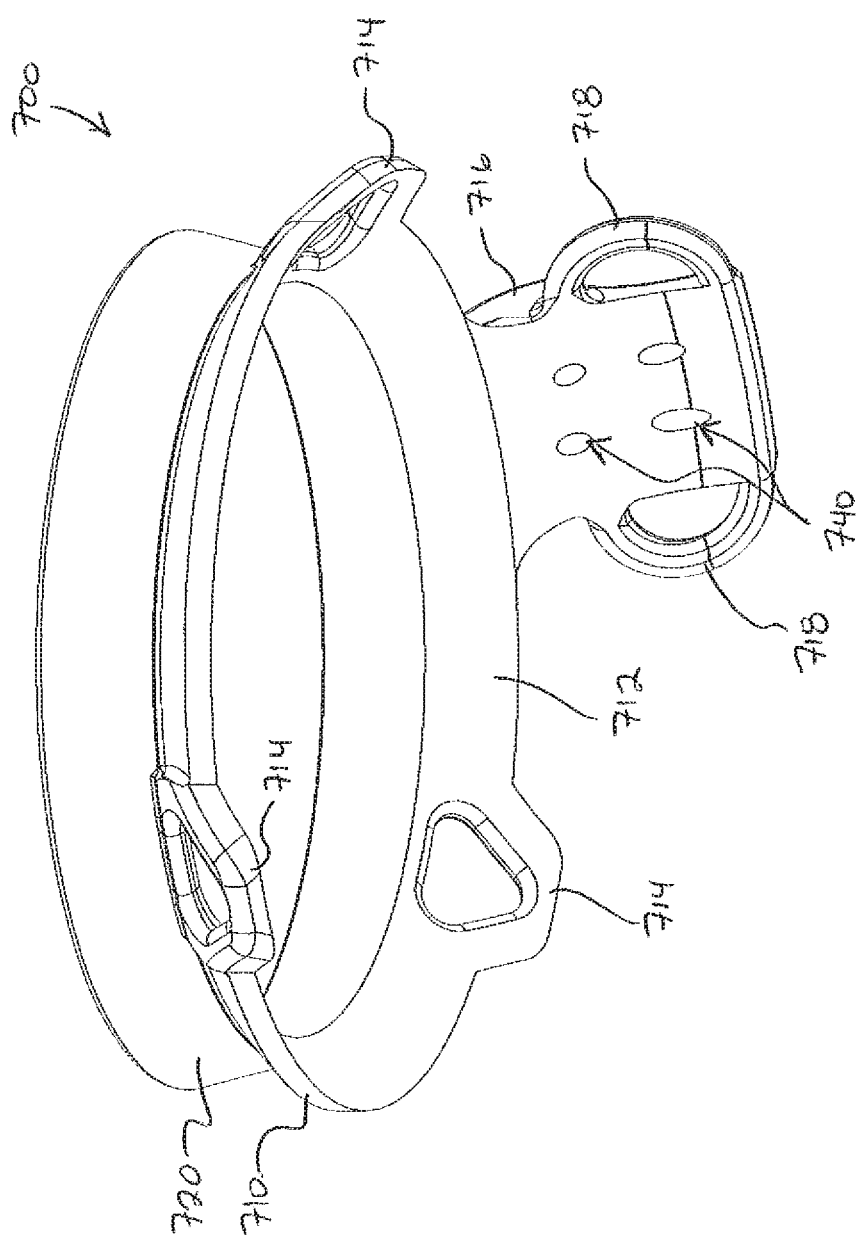
FIG. 41 depicts another perspective view of the guidance device of FIG. 40.
Figure 42:
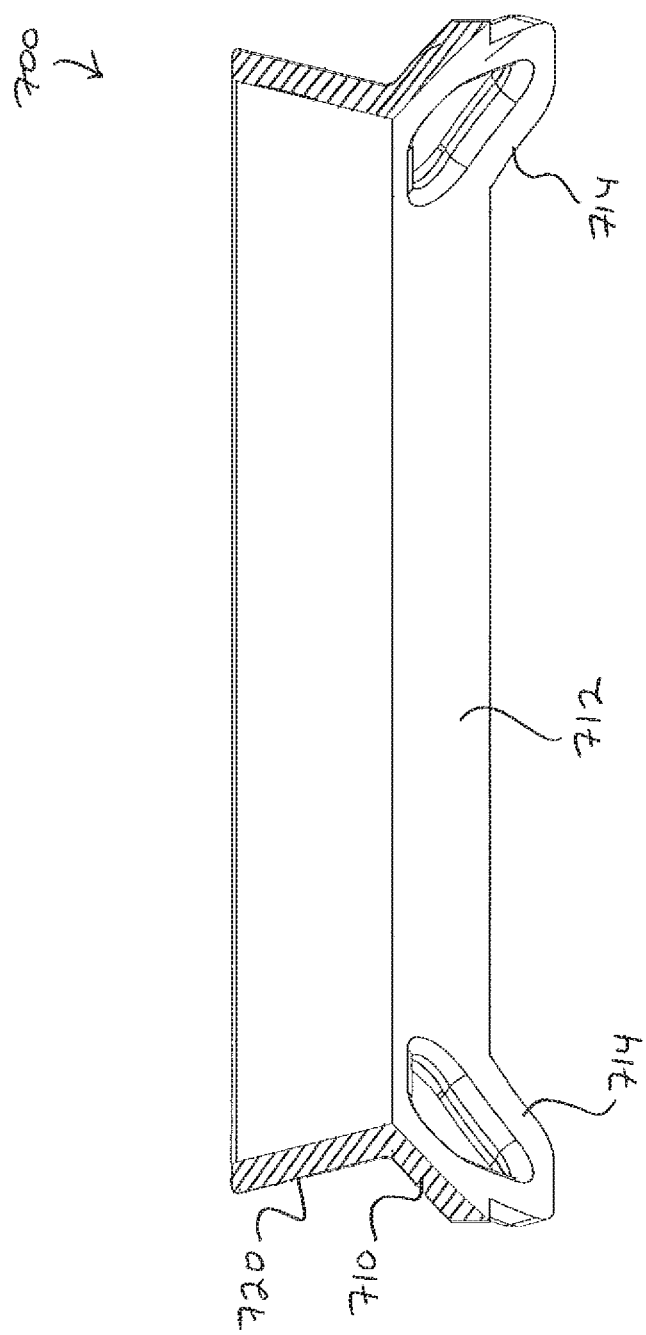
FIG. 42 depicts a cross-sectional side elevational view of the guidance device of FIG. 40 taken along line 42-42 of FIG. 40.

FIGS. 28-39 show an exemplary guidance device (700). Guidance device (700) comprises an annular base (710), a bottom surface (712) of which is configured to complement the contour of the limbic region of a patient's eye (301). Annular base (710) includes a plurality of suture loops (714) such that guidance device (700) may be secured to a patient's eye (301) via sutures (715) passed through suture loops (714) as shown in FIG. 39. Additionally or alternatively, guidance device (700) may be secured to a patient's eye (301) via adhesives, suction, micro-barbs, textured surfaces, or by contact pressure and stabilization by an operator. Annular base (710) further includes a guidance anchor (716), a bottom surface (717) of which is also configured to complement the contour of a patient's eye (301). With guidance device (700) secured to a patient's eye (301), guidance anchor (716) is shaped to extend along a side region of a patient's eye (301) as best seen in FIGS. 39-40C. Guidance anchor (716) includes a pair of suture loops (718) such that guidance anchor (716) may be secured to a patient's eye (301) via sutures (715) that are passed through suture loops (718) as shown in FIG. 39. Additionally or alternatively, guidance anchor (716) may be secured to a patient's eye (301) via adhesives, suction, micro-barbs, textured surfaces, or by contact pressure and stabilization by an operator.

Figure 34:
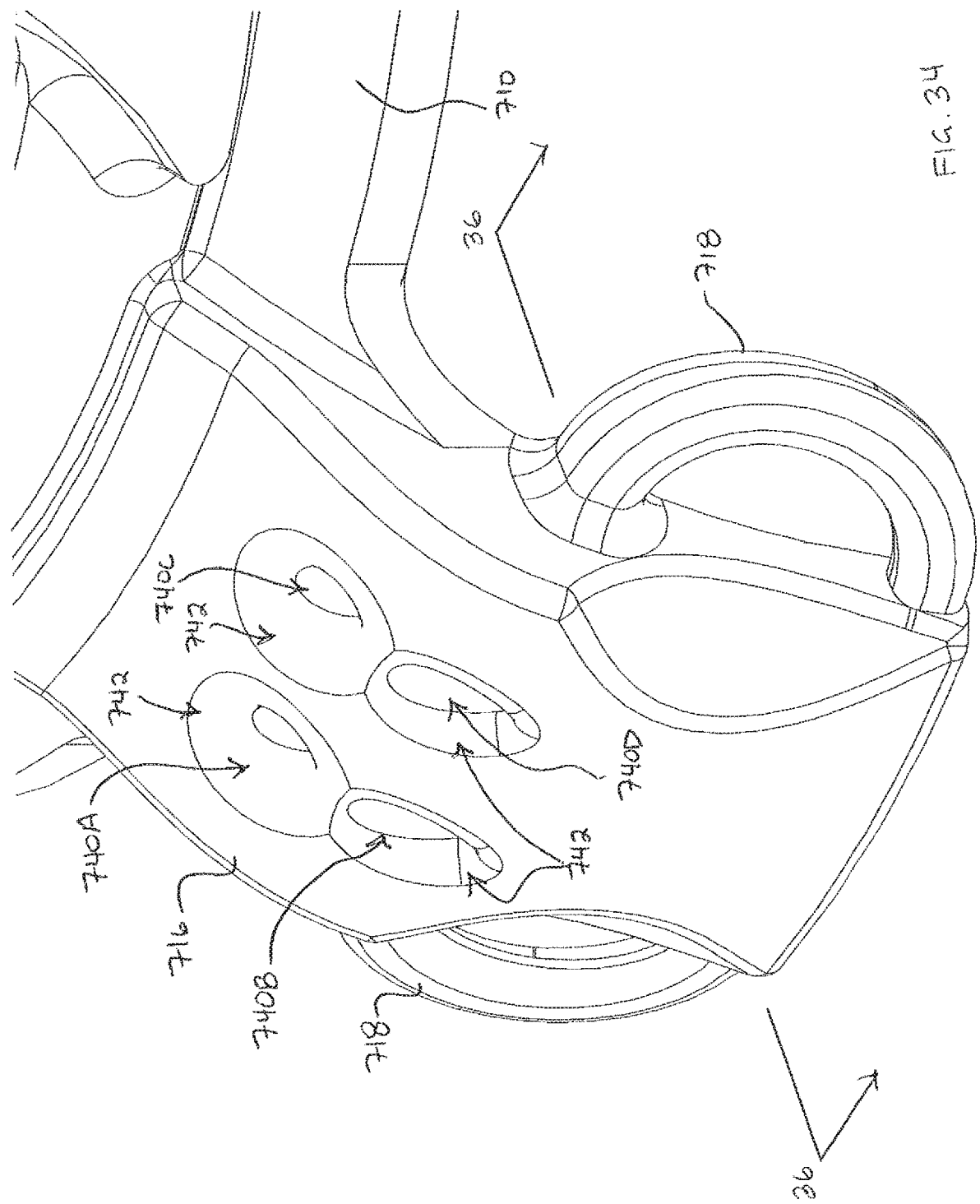
FIG. 34 depicts a detailed perspective view of a guidance anchor of the guidance device of FIG. 28.
Figure 35:
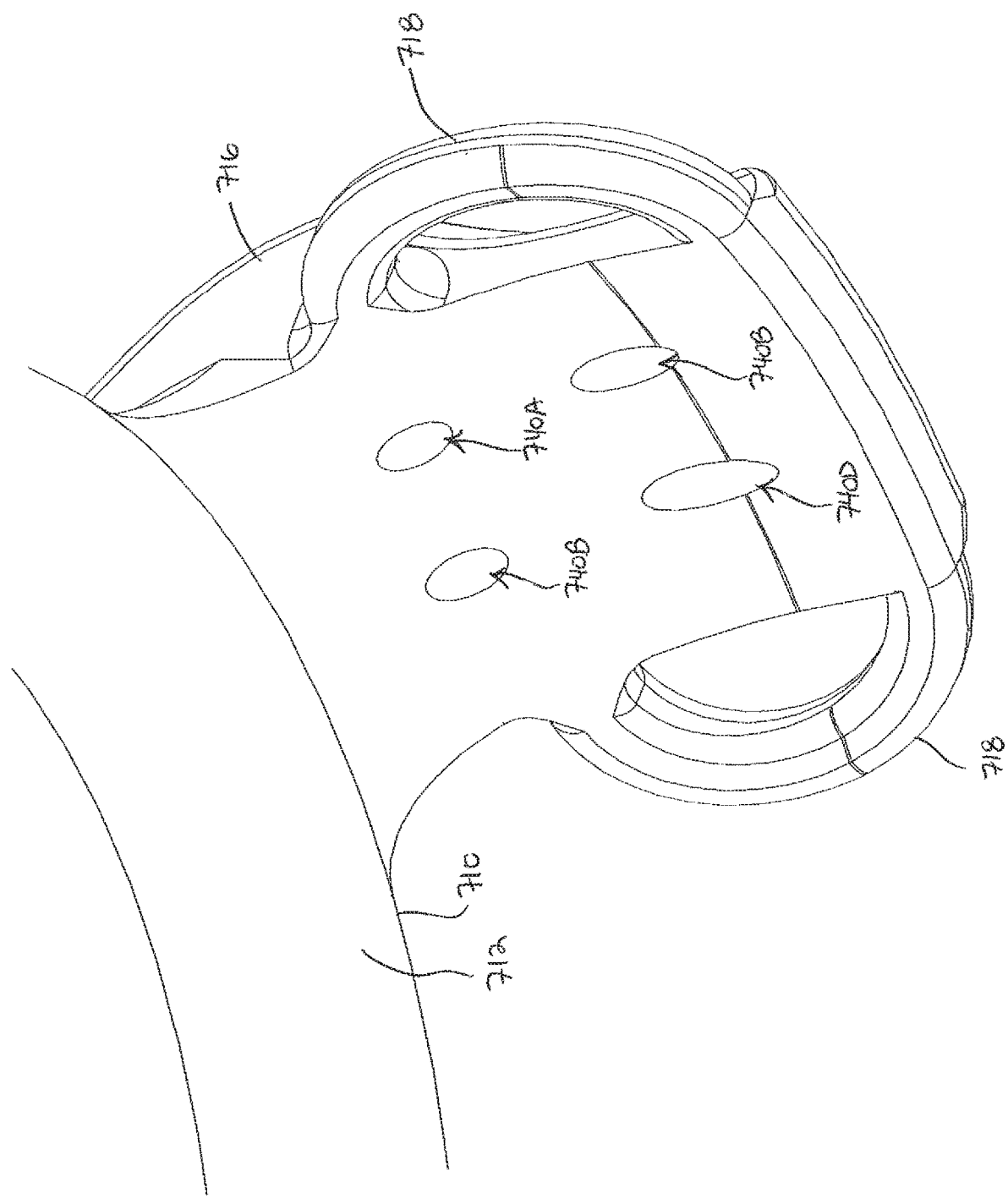
FIG. 35 depicts another detailed perspective view of the guidance anchor of FIG. 34.
Figure 36:
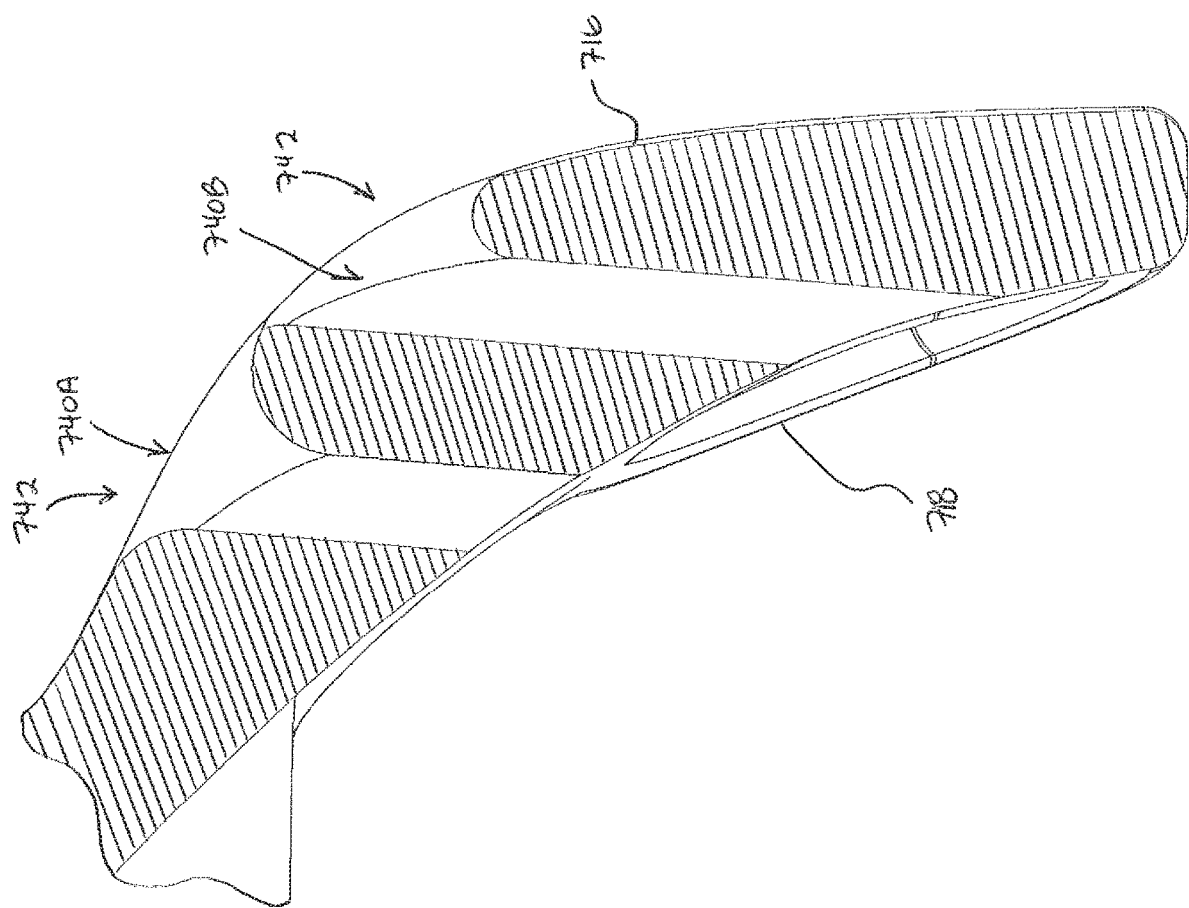
FIG. 36 depicts a detailed cross-sectional side view of the guidance anchor of FIG. 34 taken along line 36-36 of FIG. 34.

As best seen in FIGS. 34-36, guidance anchor (716) includes a plurality of through bores (740A, 740B, 740C, 740D), which extend completely through guidance anchor (716). Through bores (740A, 740B, 740C, 740D) are configured to receive needle (420, 520, 620) of instrument (400, 500, 600) so as to guide needle (420, 520, 620) into contact with a patient's eye (301) at a predetermined angle. As best seen in FIG. 34, each through bore (740A, 740B, 740C, 740D) includes a filleted opening (742) formed in a top surface (719) of guidance anchor (716). Filleted openings (742) are configured to assist an operator in guiding needles (420, 520, 620) into through bores (740A, 740B, 740C, 740D). As best seen in FIG. 36, each through bore (740A, 740B, 740C, 740D) defines a unique guidance pathway based on a position and angle of entry provided by each through bore (740A, 740B, 740C, 740D). Thus, it should be appreciated that each through bore (740A, 740B, 740C, 740D) will direct needle (420, 520, 620) into contact with a patient's eye (301) along a unique path via contact between interior surfaces of through bores (740A, 740B, 740C, 740D) and an exterior surface of needle (420, 520, 620). An operator may determine which unique path is most appropriate based on the individual characteristics (contour, curvature, thickness, toughness, etc.) of each patient's eyes (301). For instance, as will be described in more detail below, an operator may determine the most appropriate path for directing needle (420, 520, 620) through the sclera (304) and the choroid (306) to the subretinal space of a patient's eye (301).

Figure 33:
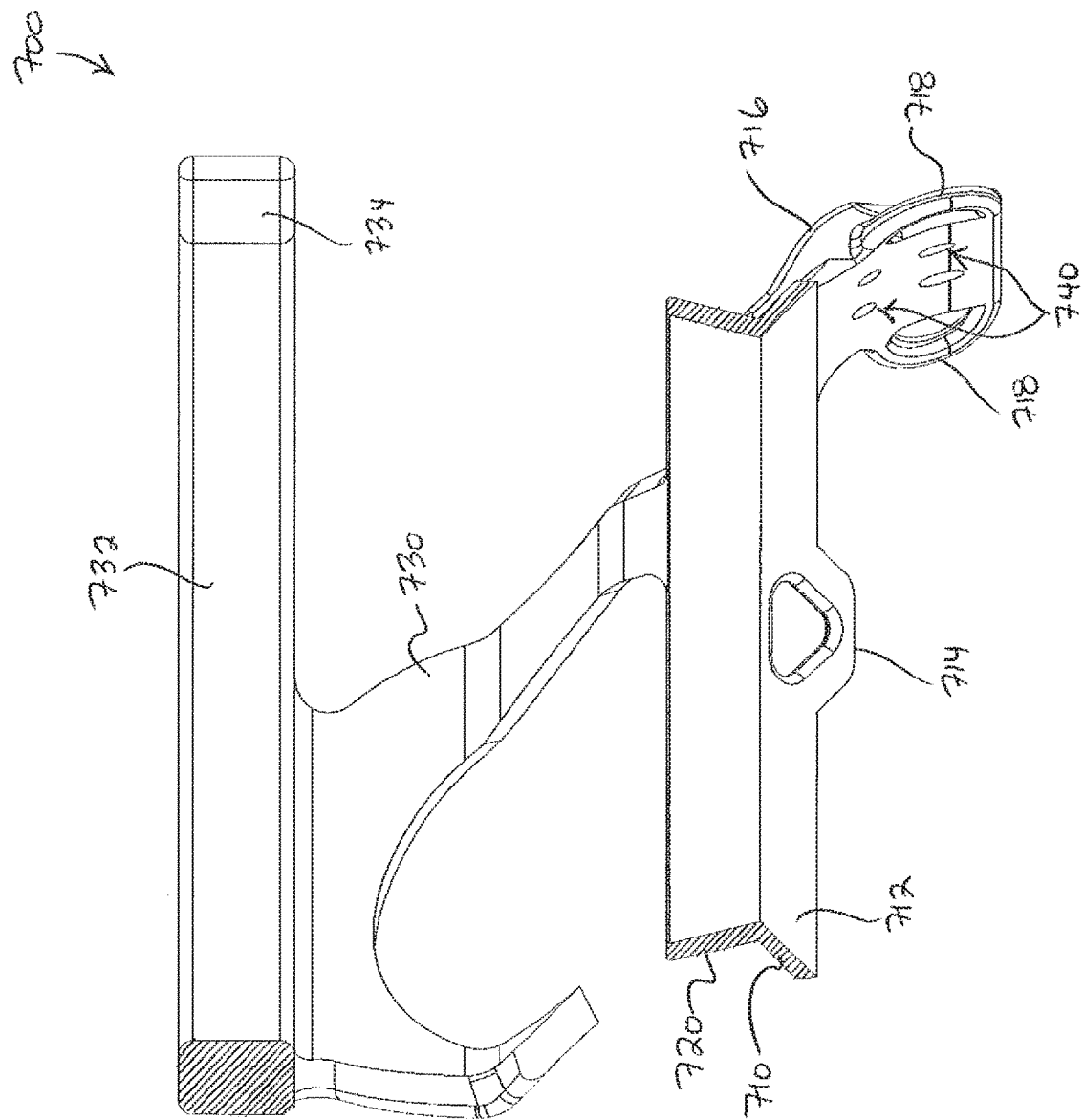
FIG. 33 depicts a cross-sectional side elevational view of the guidance device of FIG. 28 taken along line 33-33 of FIG. 29.

Guidance device (700) further comprises a frusto-conical projection (720) extending upwardly from annular base (710). As will be described in more detail below, frusto-conical projection (720) is configured to receive a viewing lens (750) that is operable to provide for viewing of the interior of a patient's eye (301) through the pupil of the eye (301) via an opening (722) formed through frusto-conical projection (720) and annular base (710) as best seen in FIG. 33. A support frame (730) extends upwardly from frusto-conical projection (720). As will be described in more detail below, support frame (730) is configured to selectively secure viewing lens (750) to guidance device (700) and to further provide support and stability to viewing lens (750) during use. Support frame (730) includes a semi-circular support member (732). Support member (732) is resiliently biased to the shape best seen in FIGS. 28 and 29. Support member (732) includes a pair of curved flanges (734), which provide support member (732) with a flared opening operable to receive viewing lens (750).

As shown in FIGS. 37 and 38, viewing lens (750) may be secured within guidance device (700). Viewing lens (750) may be, for instance, one of several ophthalmic lenses manufactured by Volk® or any other appropriate type of viewing lens. In this example, viewing lens (750) is secured within guidance device (700) via engagement with frusto-conical projection (720) and support member (732) of support frame (730). In particular, viewing lens (750) may engage and be secured within frusto-conical projection (720) via interference or snap fit. Additionally or alternatively viewing lens (750) may be secured within frusto-conical projection (720) via adhesives or by any other appropriate manner. In addition, viewing lens (750) may be stabilized by an operator. As viewing lens (750) is driven into contact with frusto-conical projection (720), contact between viewing lens (750) and flanges (734) of support member (732) causes support member (732) to open outwardly such that viewing lens (750) may be received within support member (732). As viewing lens (750) is positioned further within support member (732) to the position shown in FIGS. 37 and 38, support member (732) returns to its original shape to thereby selectively secure viewing lens (750) within support member (750).

With viewing lens (750) secured within guidance device (700), and with guidance device (700) secured to a patient's eye (301), an operator may use viewing lens (750) to view the interior of a patient's eye (301) through the pupil of the eye via opening (722) formed through frusto-conical projection (720) and annular base (710). As will be discussed in more detail below, use of viewing lens (750) may assist an operator in tracking or position of needle (420, 520, 620) and/or micro-catheter (460, 560, 660) within a patient's eye (301). It should be appreciated that before or during a surgical procedure, viewing lens (750) may be removed and perhaps replaced by other viewing lenses depending upon the need of an operator.

Figure 43:
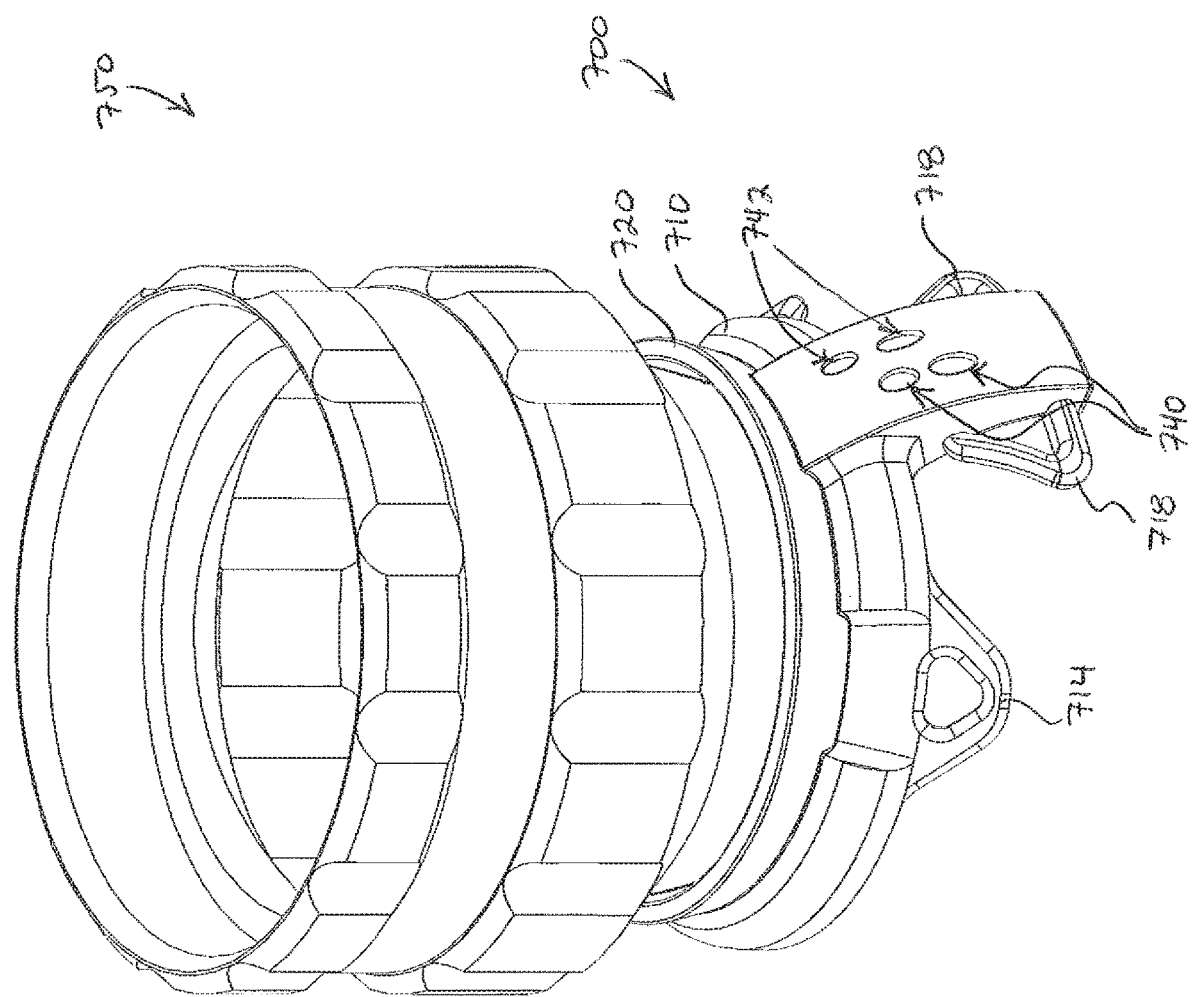
FIG. 43 depicts a perspective view of the guidance device of FIG. 40 with a viewing lens coupled within the guidance device.
Figure 44:
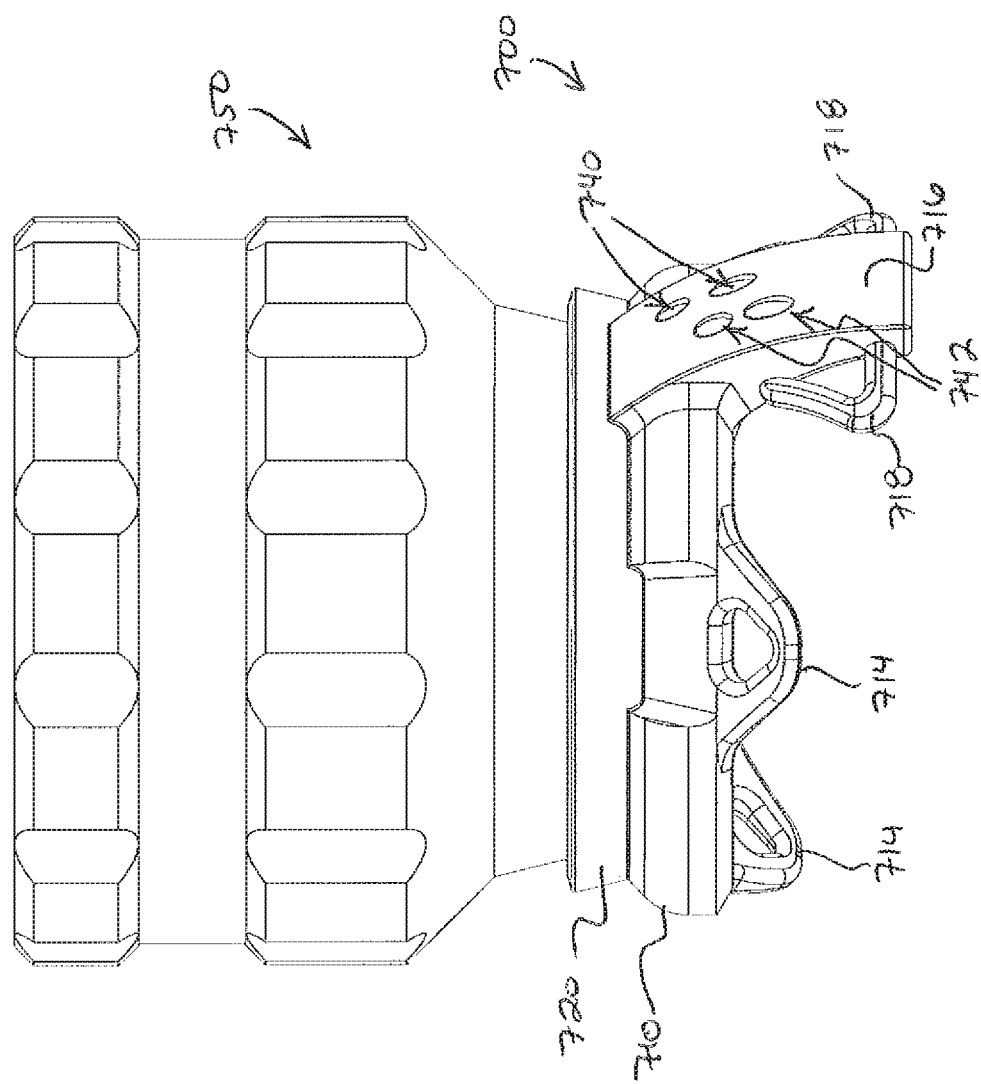
FIG. 44 depicts a side elevational view of the guidance device of FIG. 40 with the viewing lens of FIG. 43 coupled within the guidance device.
Figure 45:
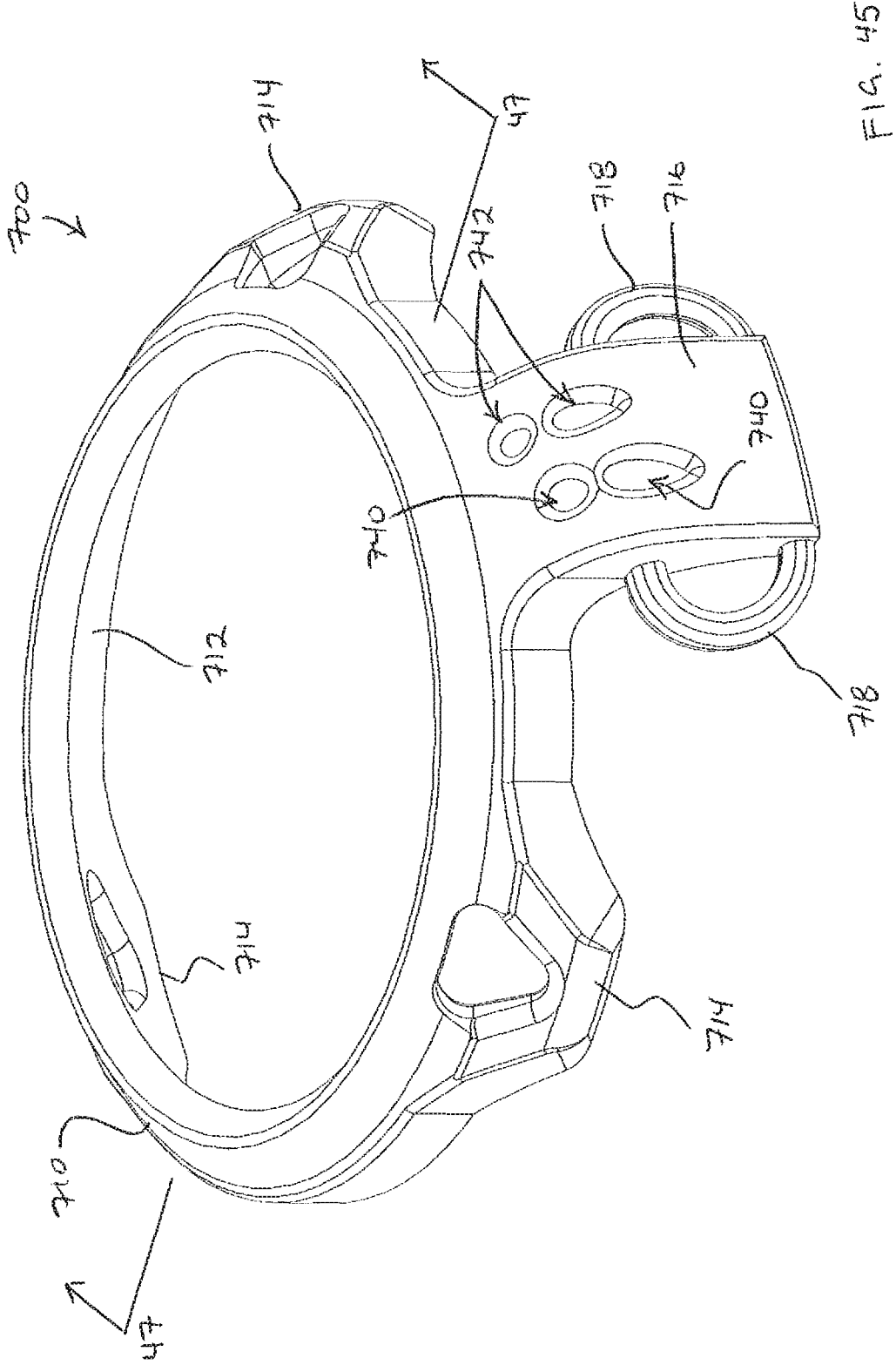
FIG. 45 depicts a perspective view of yet another exemplary guidance device.
Figure 46:
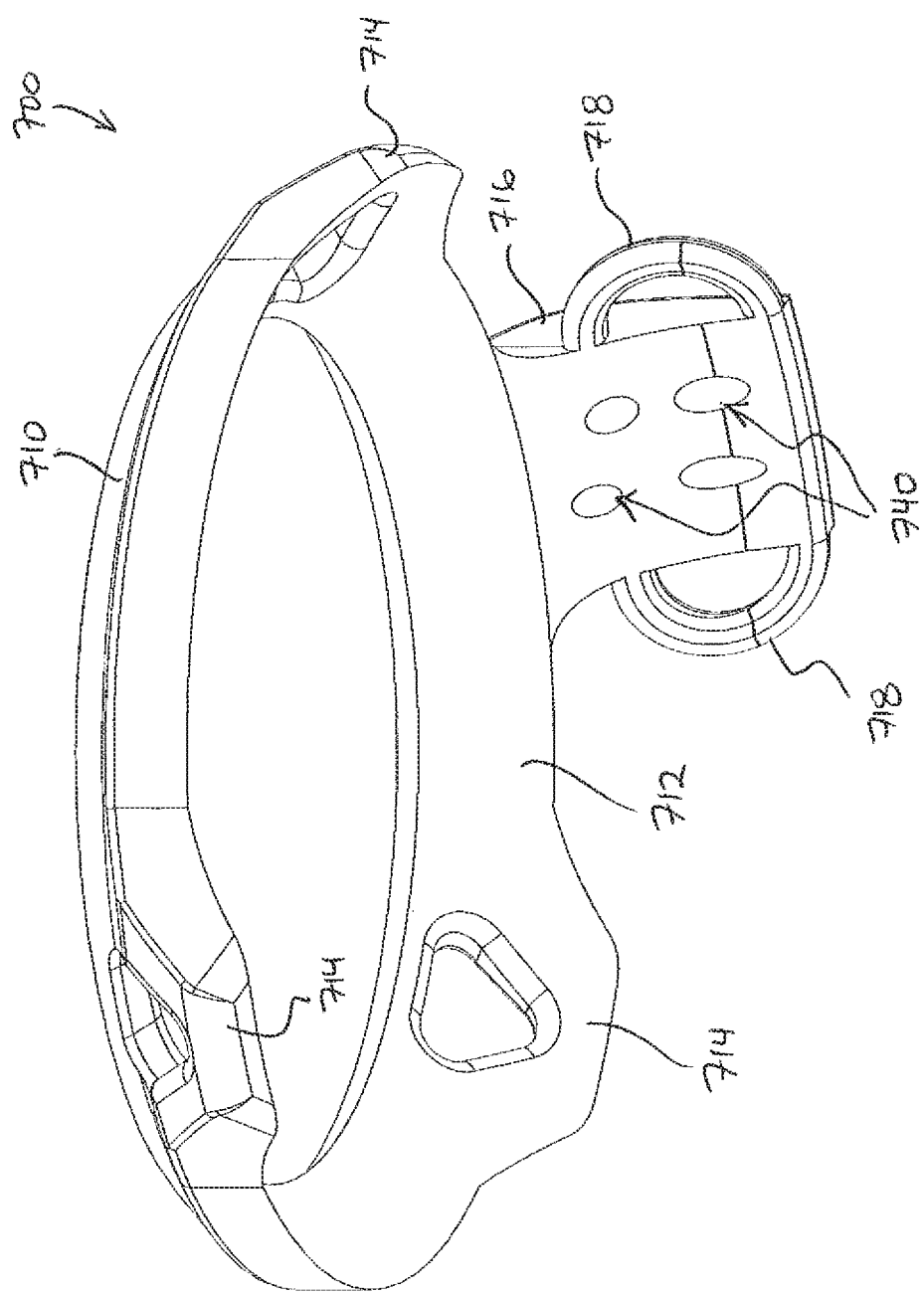
FIG. 46 depicts another perspective view of the guidance device of FIG. 45.
Figure 47:
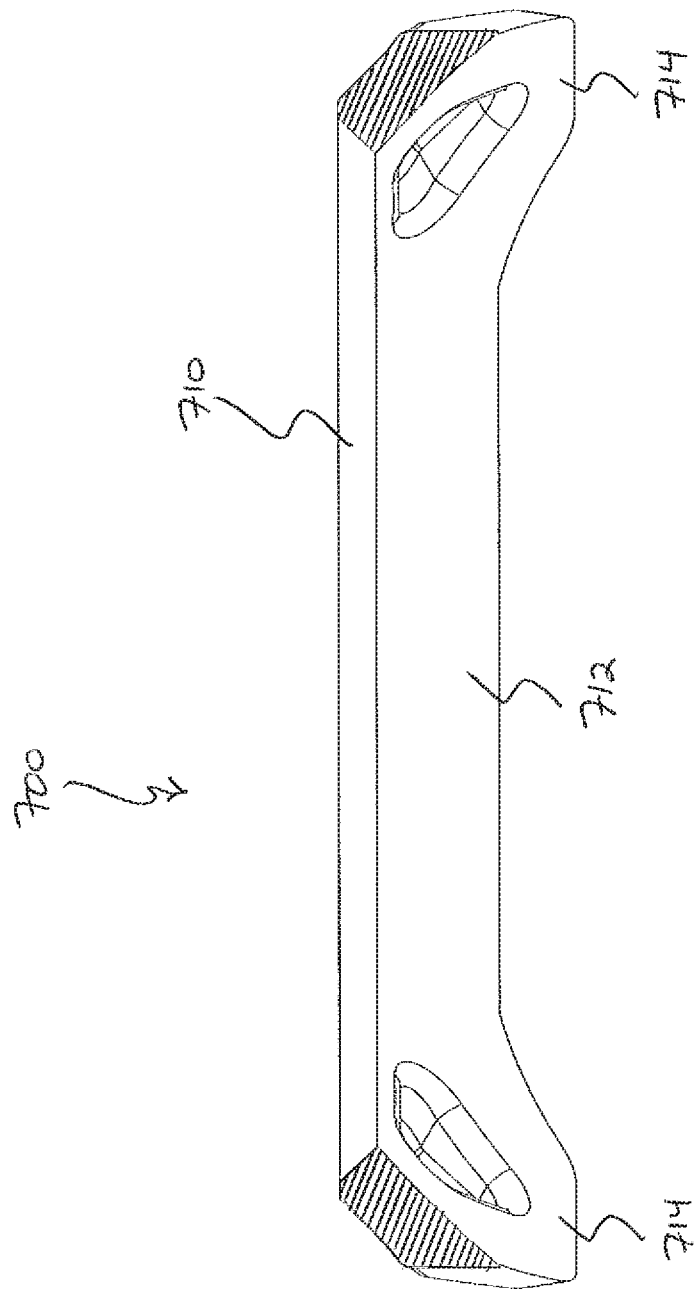
FIG. 47 depicts a cross-sectional side elevational view of the guidance device of FIG. 45 taken along line 47-47 of FIG. 45.

As shown in FIGS. 40-44, in some versions of guidance device (700), support frame (730) may be omitted from guidance device (700). In such versions of guidance device (700), viewing lens (750) may be secured within guidance device (700) via engagement with frusto-conical projection (720) as shown in FIGS. 43 and 44. In particular, viewing lens (750) may engage and be secured within frusto-conical projection (720) via interference or friction fit. Additionally or alternatively viewing lens (750) may be secured within frusto-conical projection (720) via adhesives or by any other appropriate manner. In addition, viewing lens (750) may be stabilized by an operator.

Figure 48:
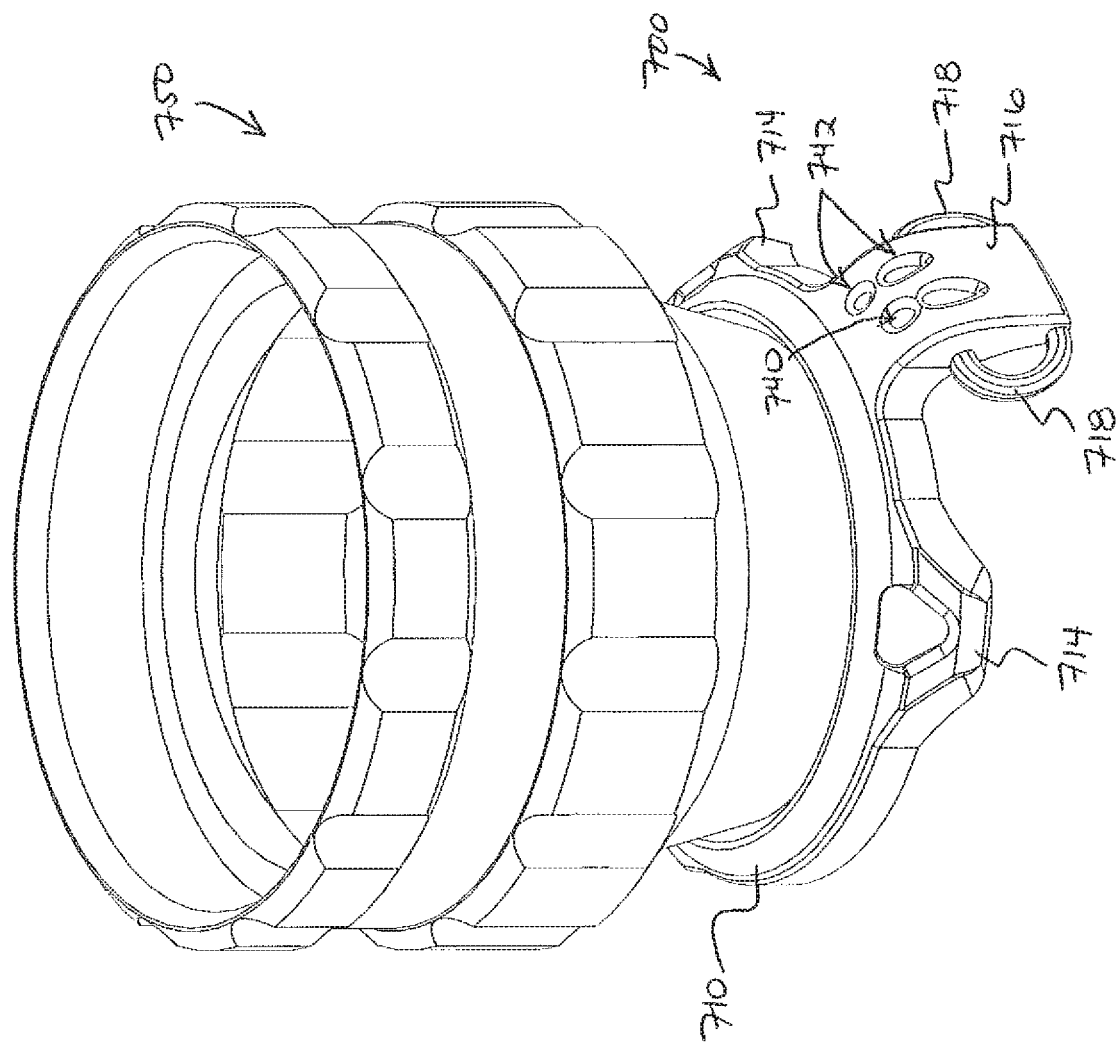
FIG. 48 depicts a perspective view of the guidance device of FIG. 45 with a viewing lens coupled within the guidance device.
Figure 49:
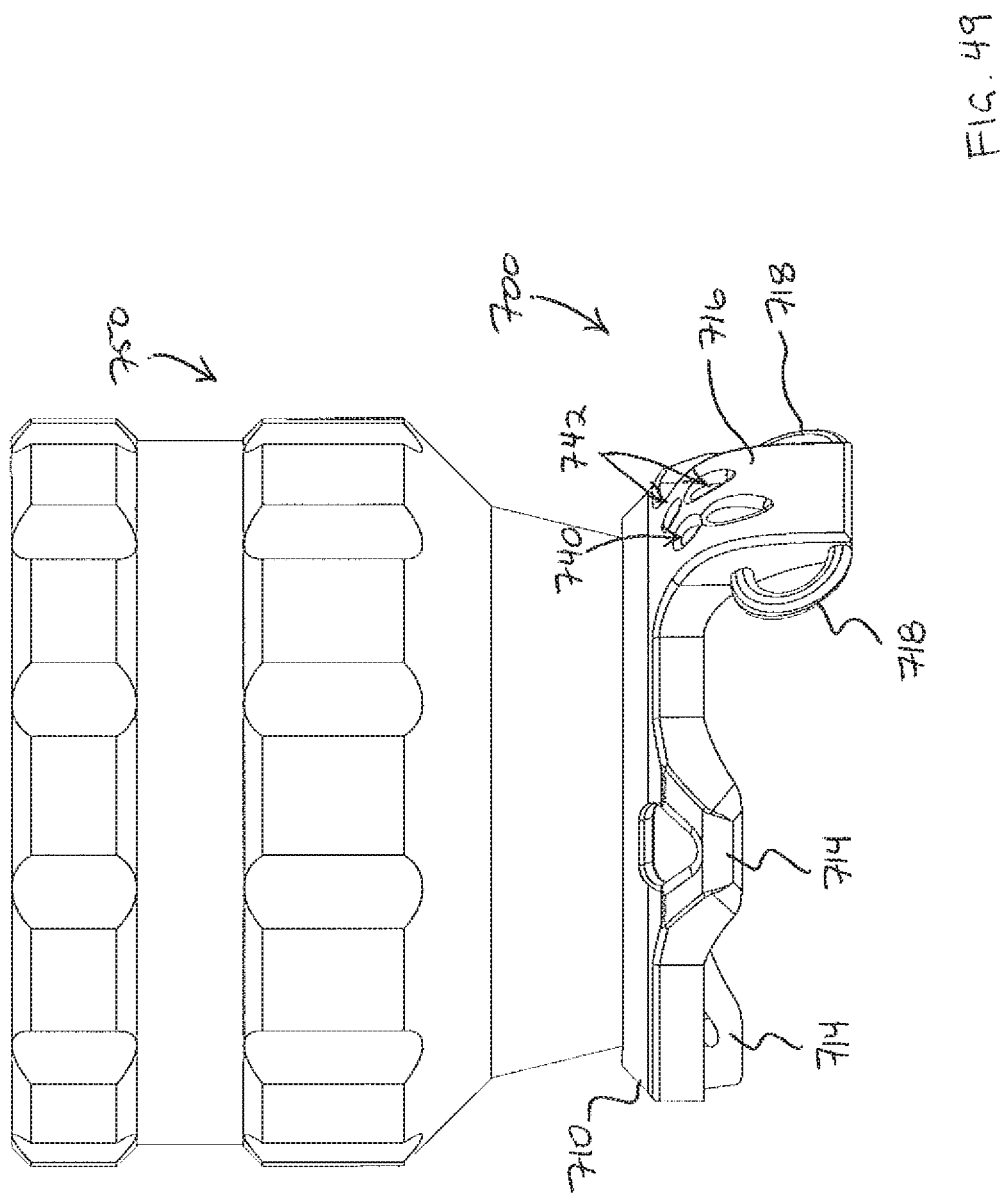
FIG. 49 depicts a side elevational view of the guidance device of FIG. 45 with the viewing lens of FIG. 43 coupled within the guidance device.

As shown in FIGS. 45-49, in some other versions of guidance device (700), in addition to support frame (730), frusto-conical projection (720) may be omitted from guidance device (700). In such versions of guidance device (700), viewing lens (750) may be secured to guidance device (700) via engagement with annular base (710) as shown in FIGS. 48 and 49. In particular, viewing lens (750) may engage and be secured to annular base (710) via interference or friction fit. Additionally or alternatively viewing lens (750) may be secured within annular base (710) via adhesives or by any other appropriate manner. In addition, viewing lens (750) may be stabilized by an operator.

Figure 50:
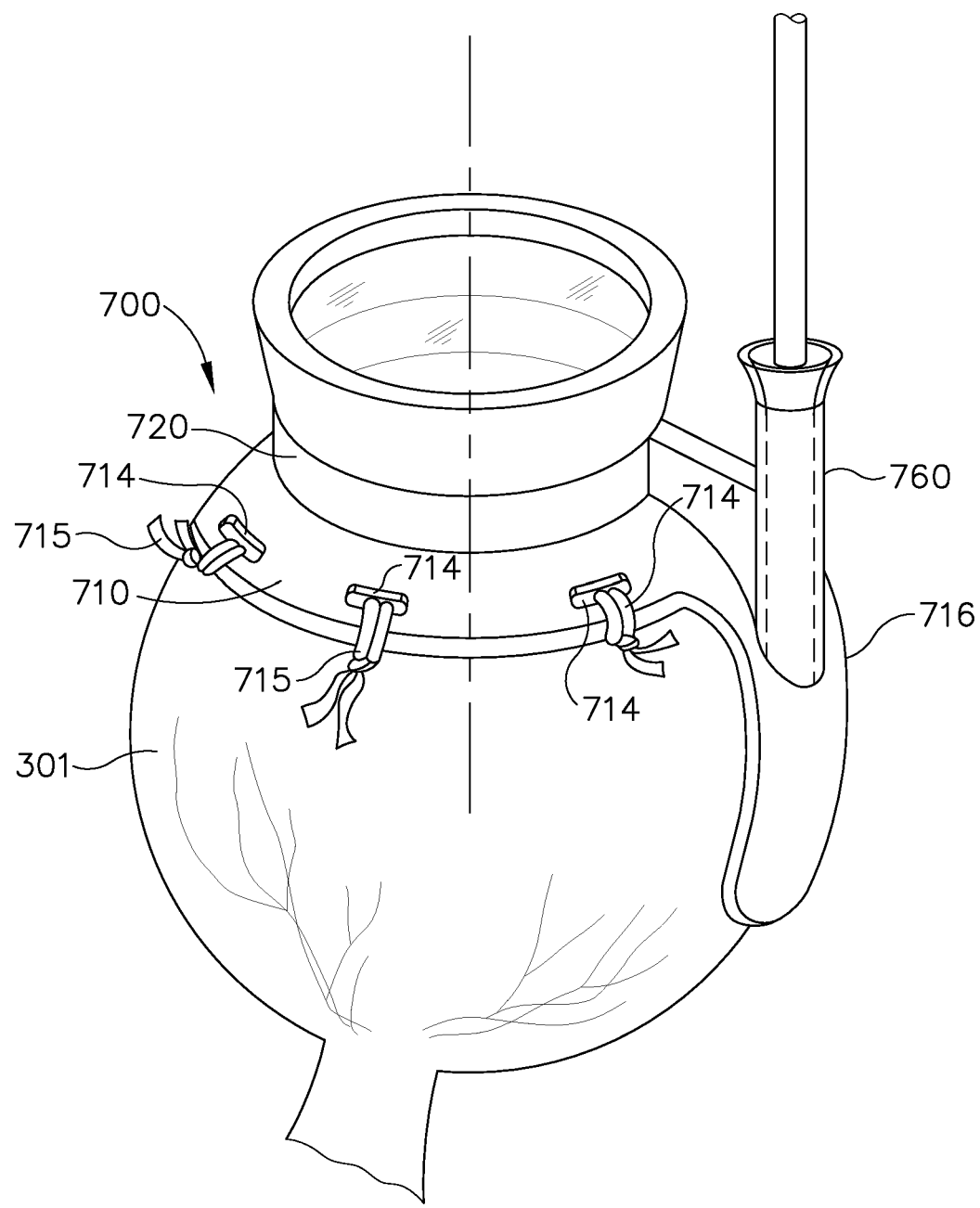
FIG. 50 depicts a perspective view of yet another exemplary guidance device attached to an eye, and with a viewing lens coupled within the guidance device.
Figure 51:
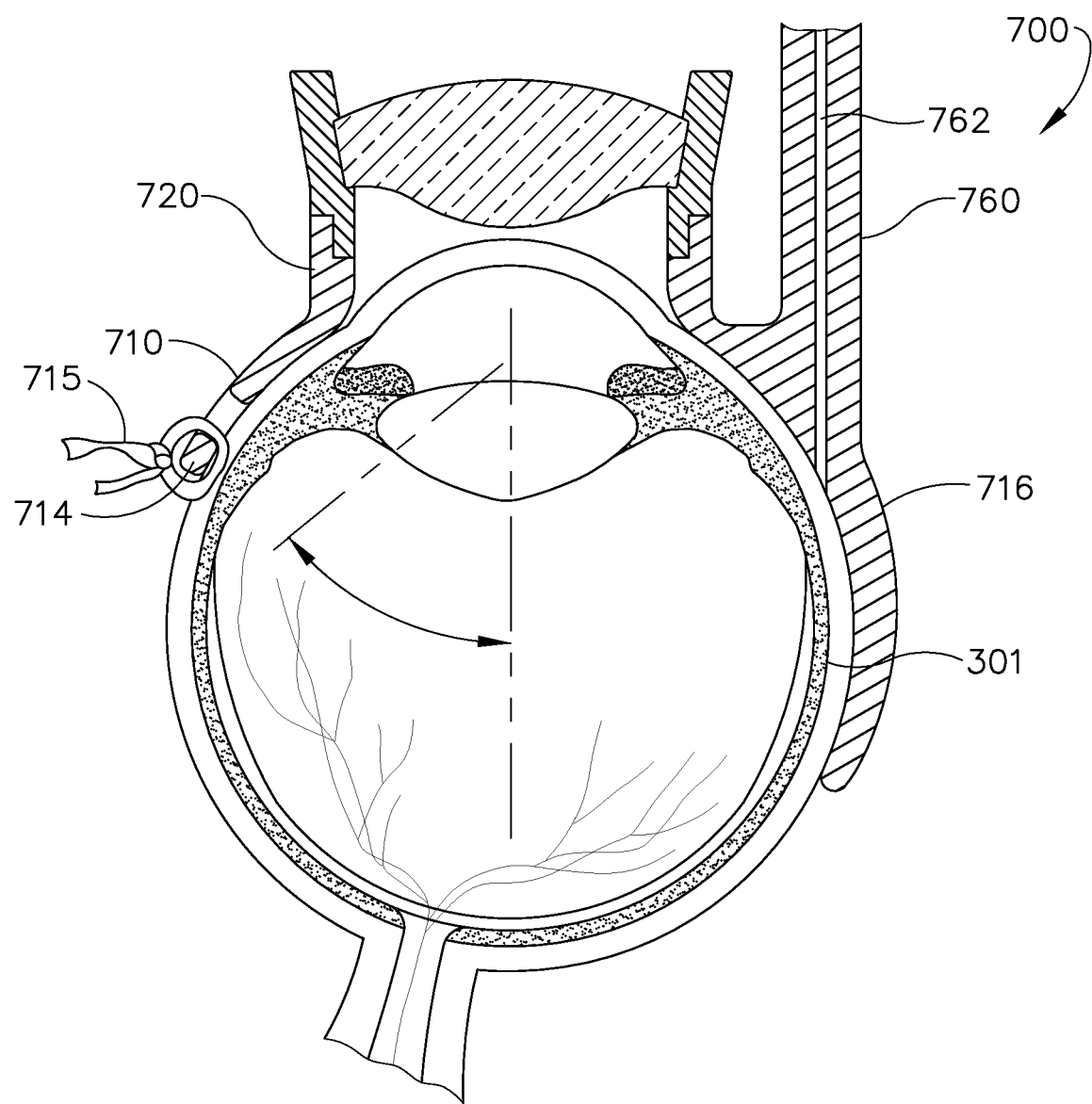
FIG. 51 depicts a cross-sectional side view of the guidance device of FIG. 50 attached to an eye, and with the viewing lens of FIG. 50 coupled within the guidance device.

As shown in FIGS. 50 and 51, in still some other versions of guidance device (700), guidance anchor (716) may include a guidance tube (760) that extends upwardly from guidance anchor (716). A lumen (762) that extends along the length of guidance tube (760) serves as an extension for one or more through bores (740A, 740B, 740C, 740D). This extended length of one or more through bores (740A, 740B, 740C, 740D) provides for additional contact between the interior surfaces of through bores (740A, 740B, 740C, 740D) and the exterior surface of needle (420, 520, 620). This increased contact provides for more accurate guidance of needle (420, 520, 620) as needle (420, 520, 620) is advanced through the sclera (304) and the choroid (306) to the subretinal space of a patient's eye (301).

VI. EXEMPLARY ALTERNATIVE METHOD FOR SUBRETINAL DELIVERY OF THERAPEUTIC AGENT

FIGS. 52A-53D show an exemplary procedure for subretinal delivery of therapeutic agent using instrument (400) described above. It should be understood however, that instruments (500, 600) may be readily used in addition to or in lieu of instrument (400) in the procedure described below. Instruments (10, 2010) may also be modified to perform the procedure described below. It should also be understood that instruments (10, 2010) may be readily modified to include at least some of the above described features of instruments (400, 500, 600), even if instruments (10, 2010) are only to be used in a procedure for subretinal administration of a therapeutic agent from a suprachoroidal approach as described above with reference to FIGS. 9A-11C. Other suitable ways in which the teachings herein may be interchanged and combined will be apparent to those of ordinary skill in the art.

By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

Although not shown in FIGS. 52A-53D, the procedure begins by an operator immobilizing tissue surrounding a patient's eye (301) (e.g., the eyelids) using a speculum (312), and/or any other instrument suitable for immobilization as can be seen in FIG. 9A. After an operator has selected an appropriate guidance device (700) and viewing lens (750), viewing lens (750) is secured within guidance device (700) as described above. Guidance device (700) and viewing lens (750) are then positioned on the limbic region of the patient's eye (301) and secured thereto via suture loops (714) of annular base (710) and sutures (715). In some versions, the operator secures guidance device (700) to the patient's eye (301) with sutures (715) first; then secures lens (750) to guidance device (700) after guidance device (700) has been secured to the patient's eye (301).

Figure 52A:
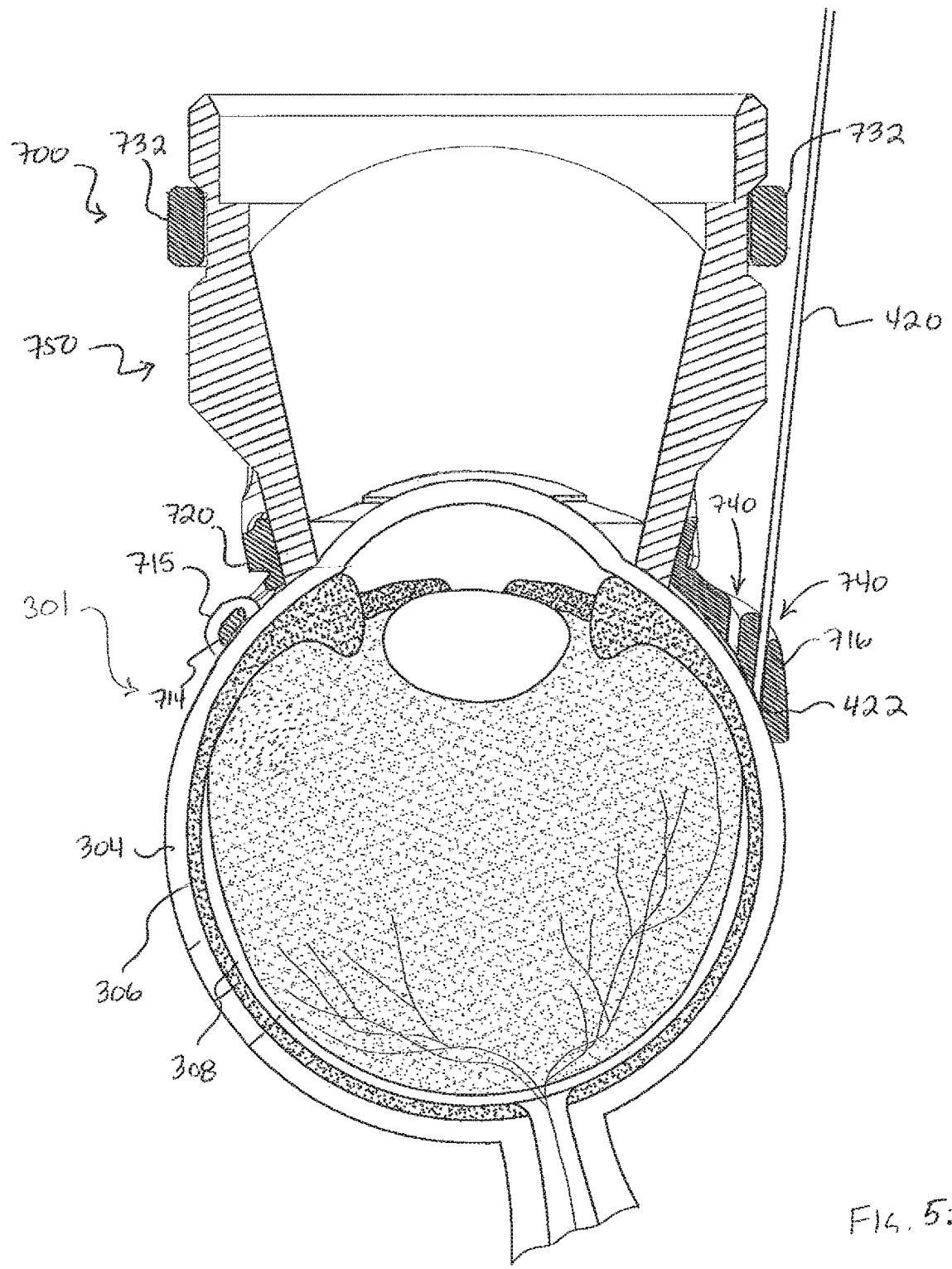
FIG. 52A depicts a cross-sectional side view of the eye of FIG. 39, with a needle of the instrument of FIG. 12 passed through an opening of the guidance device of FIG. 28 and positioned adjacent the eye.
Figure 52B:
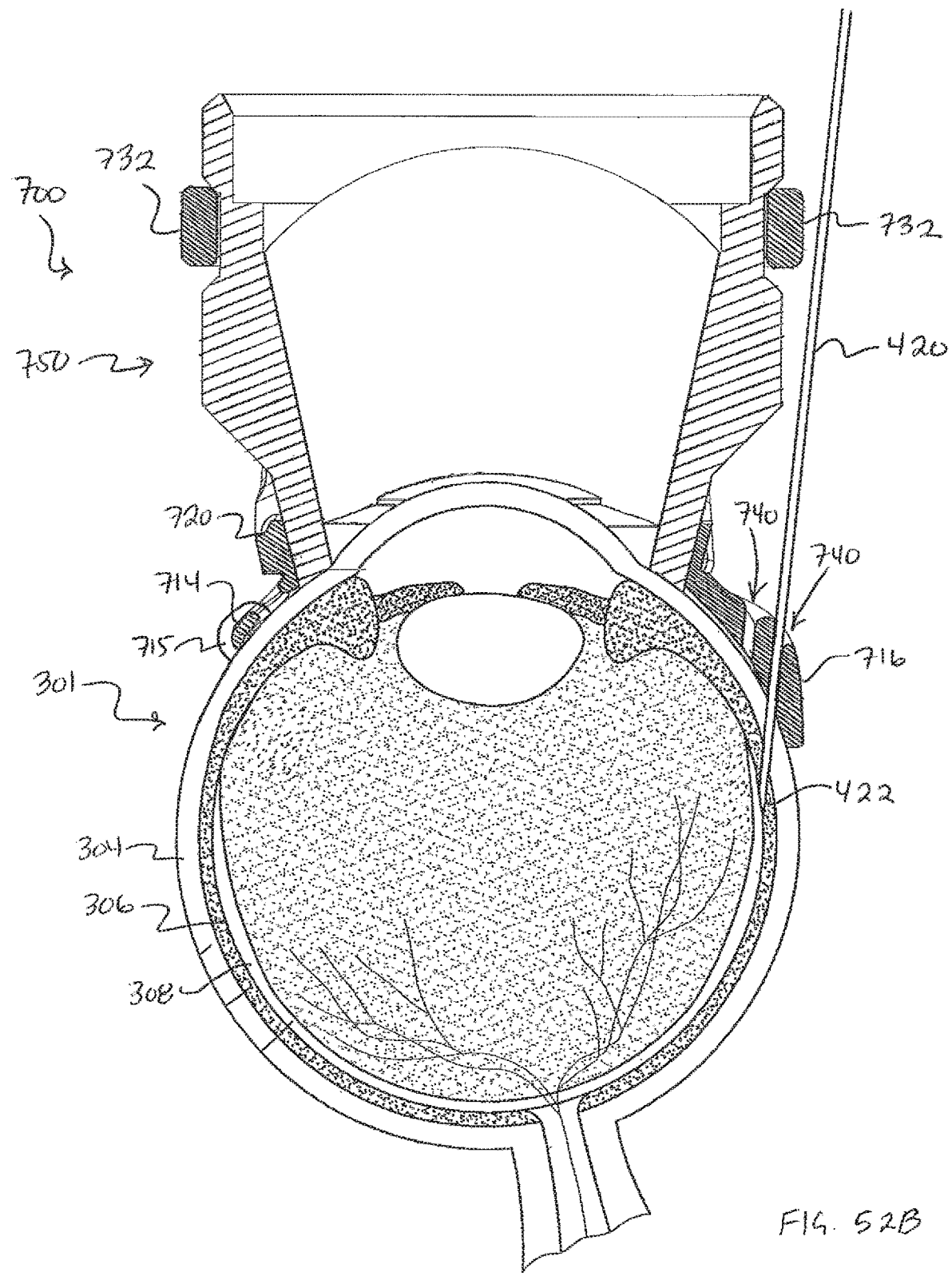
FIG. 52B depicts a cross-sectional side view of the eye of FIG. 39, with the needle of FIG. 52A passed through an opening of the guidance device of FIG. 28 and inserted into the eye so as to pierce the sclera and choroid.

After the operator has determined the appropriate through bore (740A, 740B, 740C, 740D), needle (420) is inserted into the through bore (740A, 740B, 740C, 740D) as shown in FIG. 52A. As shown in FIG. 52B, using sharp distal end (422) of needle (420), the operator then pierces the sclera (304) and advances needle (420) relative to guidance device (700) such that needle (420) pierces through choroid (306) without penetrating retina (308). Immediately prior to penetrating choroid (306), needle (420) may appear under direct visualization as "tenting" the surface of choroid (306). In other words, needle (420) may deform the choroid (306) by pushing upwardly on the choroid (306), providing an appearance similar to a tent pole deforming the roof of a tent as described above. Such a visual phenomenon may be used by an operator to identify whether the choroid (306) is about to be pierced and the location of any eventual piercing. The particular amount of needle (420) advancement sufficient to initiate "tenting" and subsequent piercing of the choroid (306) may be of any suitable amount as may be determined by a number of factors such as, but not limited to, general patient anatomy, local patient anatomy, operator preference, and/or other factors. As described above, a merely exemplary range of needle (420) advancement may be between approximately 0.25 mm and approximately 10 mm; or more particularly between approximately 2 mm and approximately 6 mm.

Although not shown, it should be understood that in some examples needle (400, 500, 600) may include one or more markers on the exterior surfaces of needle (400, 500, 600) to indicate various depths of insertion. While merely optional, such markers may be desirable to aid an operator in identifying the proper depth of insertion as needle (400, 500, 600) is guided into the patient's eye (301). For instance, the operator may visually observe the position of such markers in relation to guidance anchor (716) and/or in relation to guidance tube (760) as an indication of the depth to which needle (400, 500, 600) is inserted into the eye (301). By way of example only, one such marker may correspond to an approximately 6 mm depth of insertion of needle (400, 500, 600).

Figure 52C:
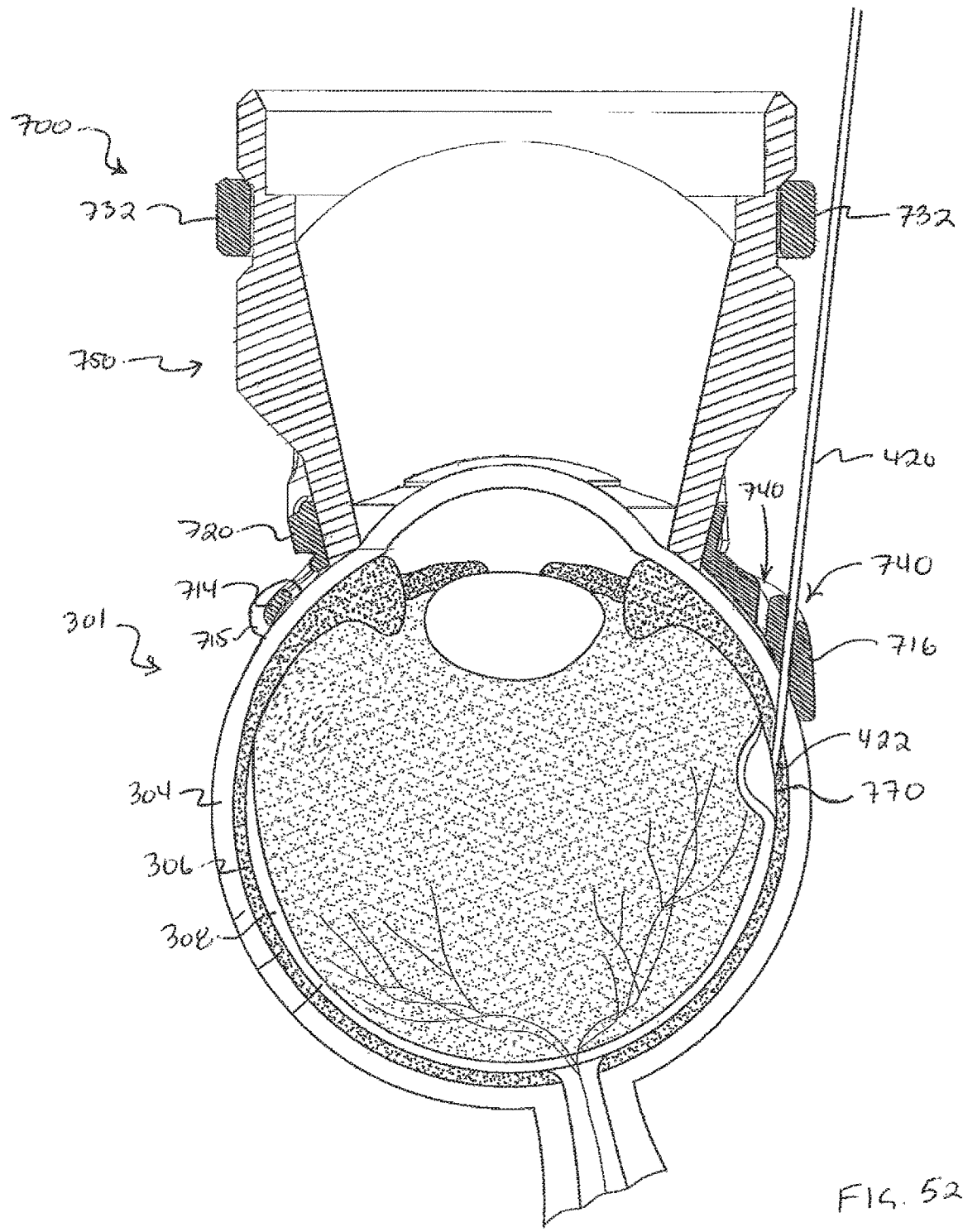
FIG. 52C depicts a cross-sectional side view of the eye of FIG. 39, with the needle of FIG. 52A passed through an opening of the needle guide of FIG. 28 and inserted into the eye so as to pierce the sclera and choroid with the needle dispensing a leading bleb under direct visualization at the side of the eye.

In the present example, after the operator has confirmed that needle (420) has been properly advanced by visualizing the tenting effect described above, the operator infuses a Healon® OVD solution, a balanced salt solution (BSS), or other similar solution via needle (420) in the subretinal space of the patient's eye (301) to form a leading bleb (770) ahead of needle (420). Leading bleb (770) may be desirable for two reasons. First, leading bleb (770) may provide a further visual indicator to an operator to indicate when needle (420) is properly positioned. Second, leading bleb (770) may provide a barrier between needle (420) and retina (308) once needle (420) has penetrated choroid (306). As will be described in more detail below, such a barrier may push the retinal wall outwardly (as is best seen in FIG. 52C), thereby minimizing the risk of retinal perforation as micro-catheter (460) is advanced to the delivery site. In some versions, a foot pedal is actuated in order to drive leading bleb (770) out from needle (420). Alternatively, other suitable features that may be used to drive leading bleb (770) out from needle (420) will be apparent to those of ordinary skill in the art in view of the teachings herein.

Figure 53A:
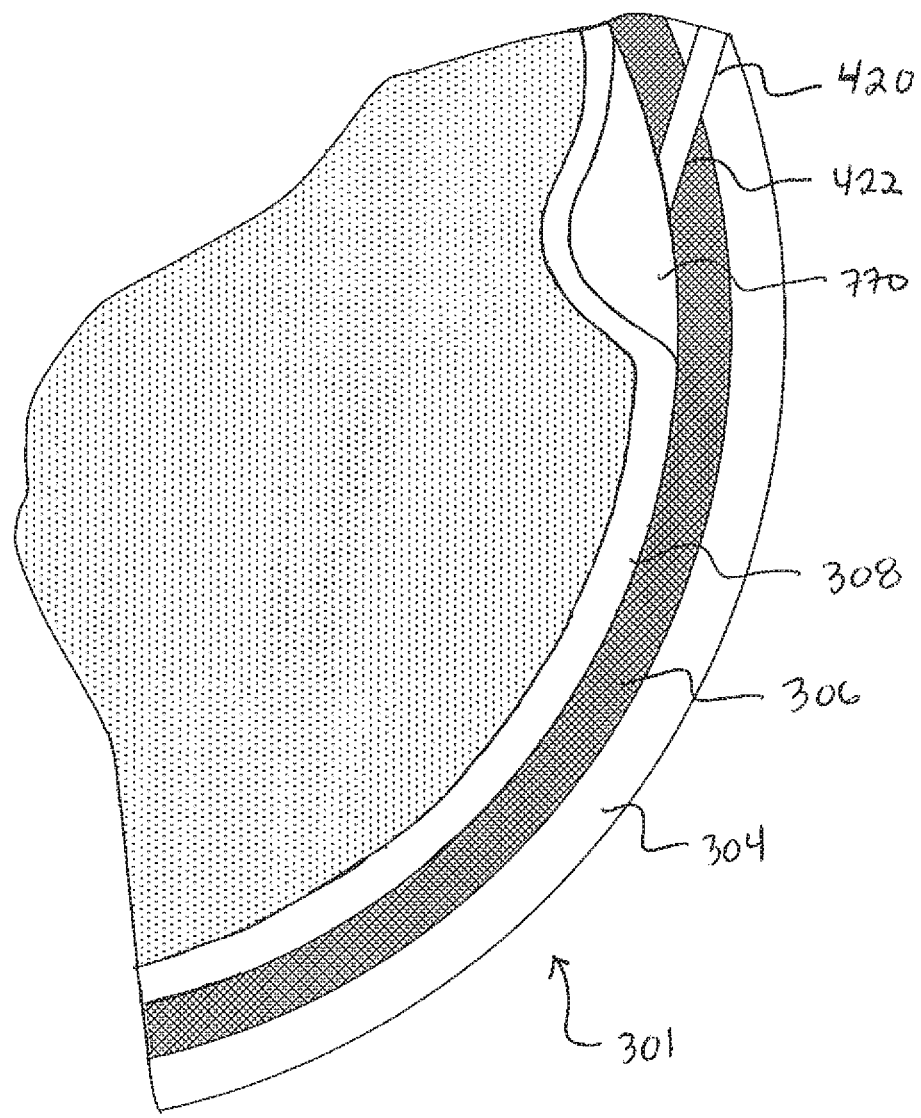
FIG. 53A depicts a detailed cross-sectional side view of the eye of FIG. 39, with the needle of FIG. 52A inserted into the eye so as to pierce the sclera and choroid with the needle dispensing a leading bleb under direct visualization at the side of the eye.
Figure 53B:
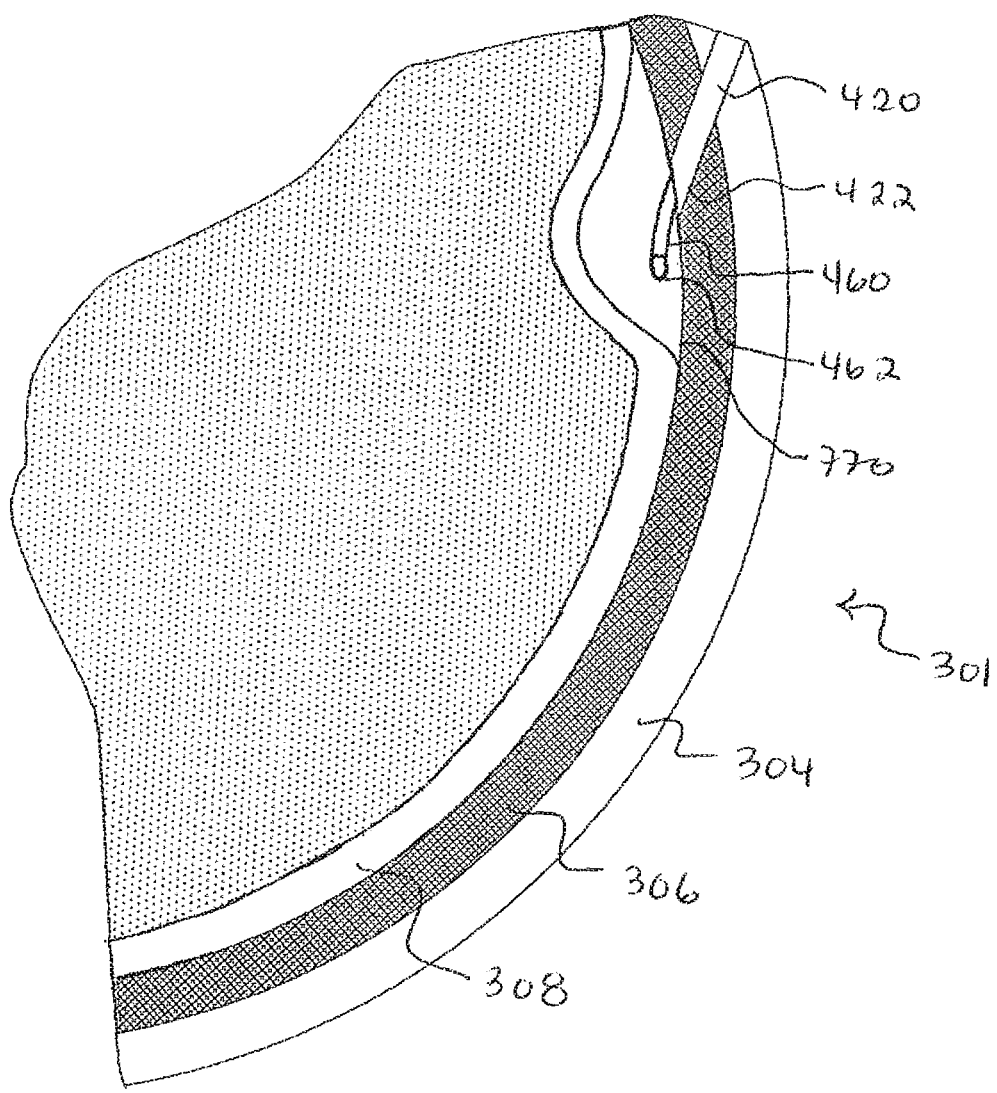
FIG. 53B depicts a detailed cross-sectional side view of the eye of FIG. 39 with a micro-catheter extended from the needle of FIG. 52A into the leading bleb.
Figure 53C:
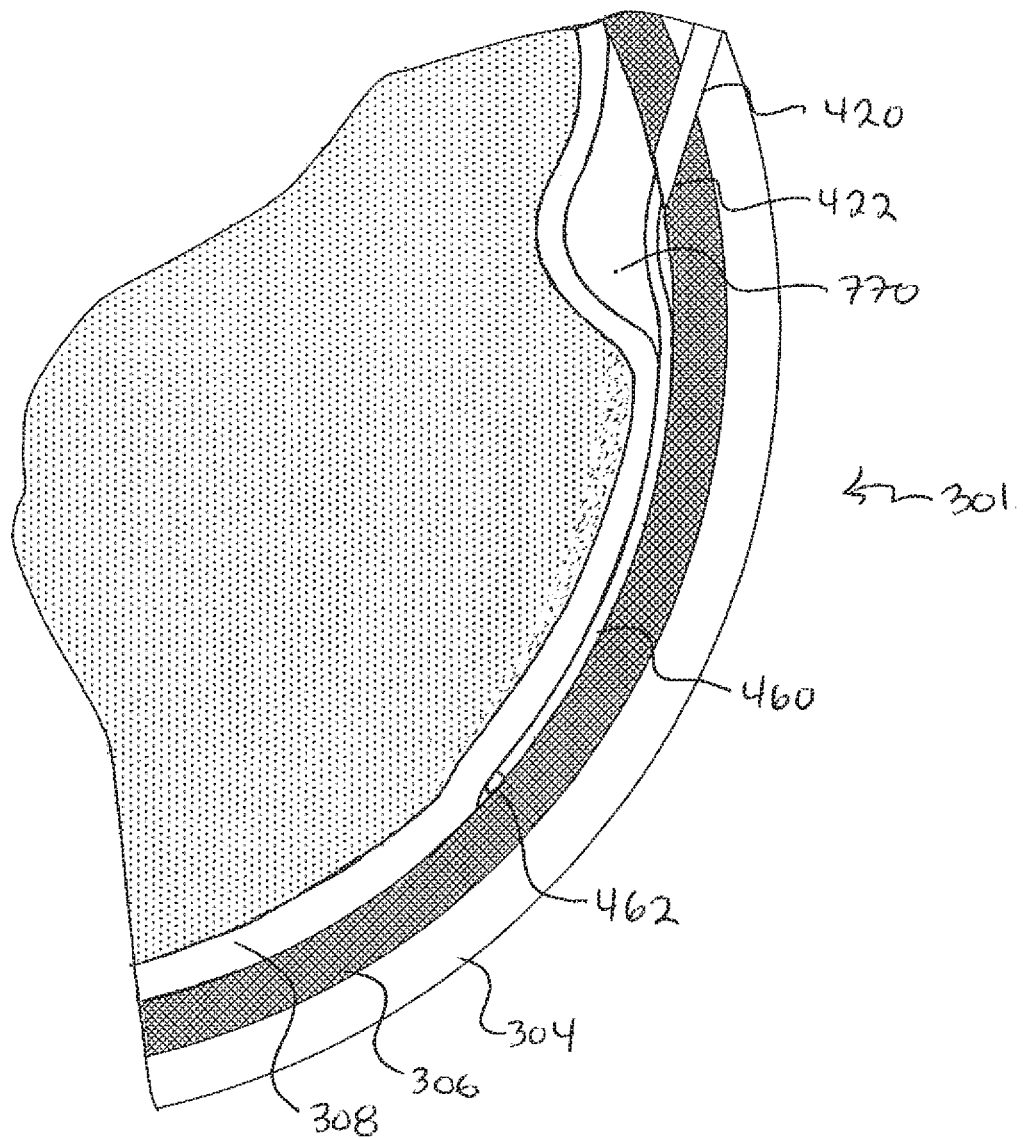
FIG. 53C depicts a detailed cross-sectional side view of the eye of FIG. 39 with the micro-catheter of FIG. 53B extended further within the sub retinal space between the choroid and a retina to the back of the eye.
Figure 53D:
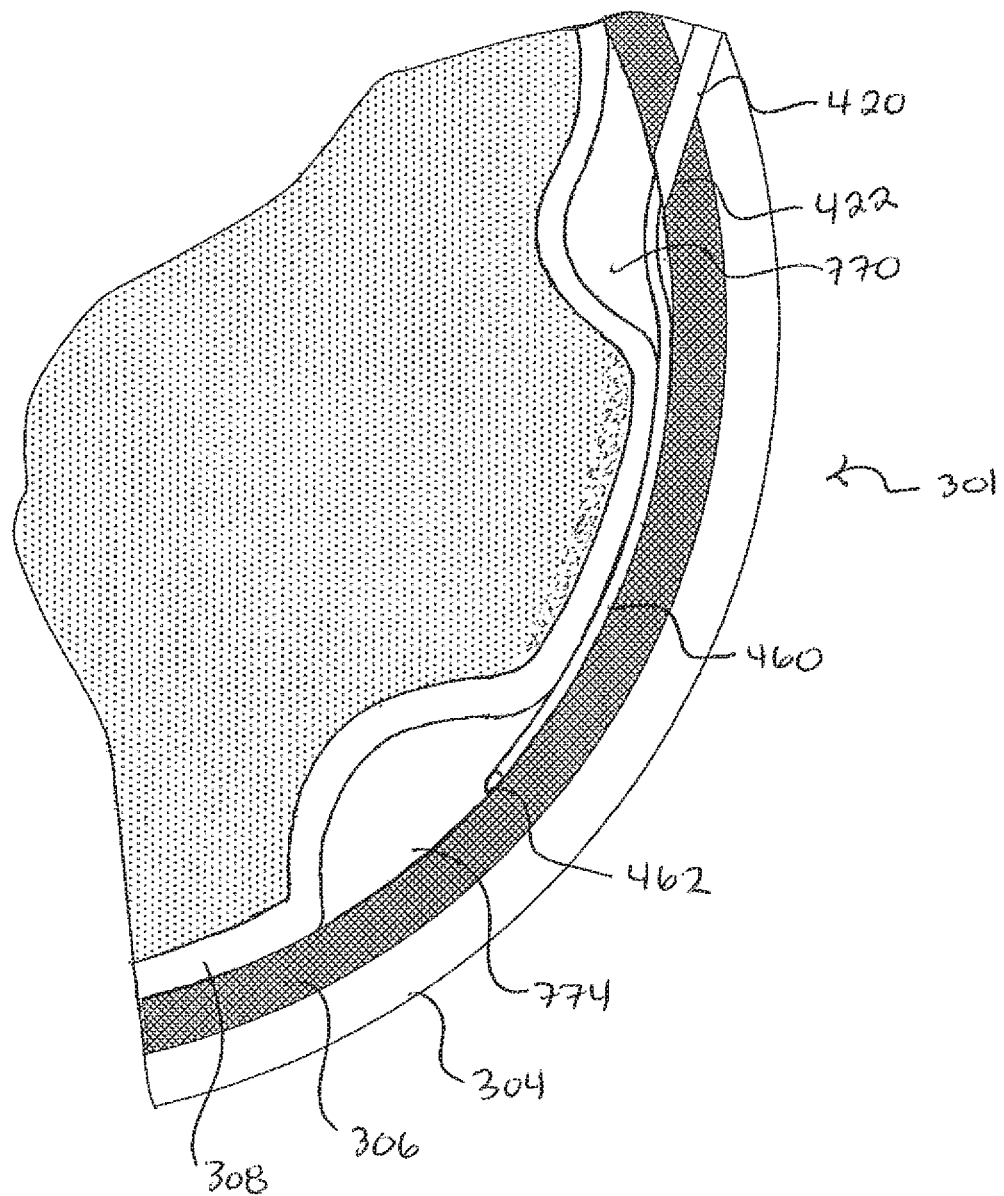
FIG. 53D depicts a detailed cross-sectional side view of the eye of FIG. 39 with the micro-catheter of FIG. 53B dispensing a therapeutic agent to the eye in the sub-retinal space at the back of the eye.

FIGS. 53A-53D show micro-catheter (460) as it is guided between choroid (306) and retina (308) to the delivery site for the therapeutic agent (774) without traversing a vitreous region of eye (301). In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. As shown in FIG. 53B, micro-catheter (460) is advanced distally from the distal end of needle (420) into the space provided by lead bleb (770). Micro-catheter (460) is at least partially visible through retina (308) of eye (301). To increase the visibility of micro-catheter (460), micro-catheter (460) may include an illuminating element (462), which may be seen via viewing lens (750). Micro-catheter (460) is then further advanced distally between the choroid (306) and the retina (308) to the delivery site as shown in FIG. 53C. As micro-catheter (460) is advanced within the patient's eye (301), micro-catheter (460) may appear under direct visualization as "tenting" the surface of retina (308). Such a visual phenomenon may be used by an operator to identify whether micro-catheter (460) has been advanced to the delivery site. Again, illuminating element (462) may be used to increase visibility of micro-catheter (460) to identify whether micro-catheter (460) has been advanced to the delivery site.

After the operator has confirmed that micro-catheter (460) has been properly advanced to the delivery site, a therapeutic agent (774) may be infused via micro-catheter (460) by actuating a syringe or other fluid delivery device. The particular therapeutic agent (774) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, and/or any other suitable therapeutic agent as will be apparent to those of ordinary skill in the art in view of the teachings herein. By way of example only, the therapeutic agent (774) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein.

In the present example, the amount of therapeutic agent (774) that is ultimately delivered to the delivery site is approximately 50 μL, although any other suitable amount may be delivered. In some versions, a foot pedal is actuated in order to drive agent (774) out from micro-catheter (460). Alternatively, other suitable features that may be used to drive agent (774) out from micro-catheter (460) will be apparent to those of ordinary skill in the art in view of the teachings herein. Delivery of therapeutic agent may be visualized as another bleb. Once delivery is complete, micro-catheter (460) may be retracted by sliding micro-catheter (460) back into needle (420); and needle (420) may then be withdrawn from eye (301). It should be understood that because of the size of needle (420), the site where needle (420) penetrated through sclera (304) and choroid (306) is self sealing, such that no further steps need be taken to seal the delivery site through choroid (306). Sutures (715) may further be removed.

As noted above, the foregoing procedure may be carried out to treat a patient having macular degeneration. In some such instances, the therapeutic agent (774) that is delivered by micro-catheter (460) may comprise cells that are derived from postpartum umbilicus and placenta. As noted above, and by way of example only, the therapeutic agent (774) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, micro-catheter (460) may be used to deliver any other suitable substance or substances, in addition to or in lieu of those described in U.S. Pat. No. 7,413,734 and/or elsewhere herein. By way of example only, therapeutic agent (774) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

VII. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body, wherein the body comprises: (i) a body distal end, (ii) a body proximal end, and (iii) a fluid port; (b) a needle, wherein the needle projects distally from the body distal end, wherein the needle comprises: (i) a needle distal end, (ii) a needle proximal end, and (iii) an inner wall defining a needle lumen, wherein the needle lumen is in fluid communication with the fluid port; (c) a catheter, slidably disposed in the needle lumen, wherein the catheter comprises: (i) a catheter distal end, (ii) a catheter proximal end, and (iii) a catheter lumen; and (d) a first actuator assembly, wherein the first actuator assembly is configured to translate the catheter within and relative to the needle.

Example 2

The apparatus of Example 1, wherein the fluid port is located in an intermediate region of the body between the body distal end and the body proximal end.

Example 3

The apparatus of Example 2, wherein the body defines a chamber, wherein the fluid port terminates at the chamber, wherein the needle proximal end terminates at the chamber.

Example 4

The apparatus of Example 3, wherein the catheter passes through the chamber.

Example 5

The apparatus of any one of Examples 1 through 4, wherein the needle lumen and catheter are sized to define a gap between the inner wall of the needle and an outer surface of the catheter, wherein the gap is configured to provide a pathway for fluid communication from the fluid port to the needle distal end

Example 6

The apparatus of any one of Examples 1 through 5, wherein the needle has a preformed bend.

Example 7

The apparatus of any one of Examples 1 through 6, wherein the catheter is flexible.

Example 8

The apparatus of any one of Examples 1 through 7, wherein the first actuator assembly comprises a control wheel rotatably supported by the body, wherein the first actuator assembly is operable to translate the catheter longitudinally within and relative to the needle in response to rotation of the control wheel relative to the body.

Example 9

The apparatus of Example 8, wherein the body defines a longitudinal axis, wherein the control wheel is rotatable relative to the body about an axis that is perpendicular to the longitudinal axis of the body.

Example 10

The apparatus of Example 8, wherein the first actuator assembly comprises: (i) a pinion coupled with the control wheel, wherein the pinion is configured to rotate in response to rotation of the control wheel, and (ii) a rack coupled with the catheter, wherein the rack is engaged with the pinion such that the rack is configured to translate in response to rotation of the pinion.

Example 11

The apparatus of any one of Examples 1 through 10, wherein the first actuator assembly comprises a plunger slidably disposed within the body, wherein the plunger is secured to the catheter such that the catheter is configured to translate relative to the body in response to translation of the plunger relative to the body.

Example 12

The apparatus of Examples 1 through 11, wherein the needle is configured to rotate relative to the body.

Example 13

The apparatus of Example 12, further comprising a second actuator assembly, wherein the second actuator assembly is operable to rotate the needle longitudinally relative to the body.

Example 14

The apparatus of Example 13, wherein the second actuator assembly comprises a rotatable member, wherein the rotatable member is rotatable relative to the body, wherein the needle is configured to rotate relative to the body in response to rotation of the rotatable member relative to the body.

Example 15

The apparatus of Example 14, wherein the rotatable member is configured to form a Tuohy-Borst valve.

Example 16

The apparatus of any one of Examples 1 through 15, further comprising a guidance device, wherein the guidance device comprises: (i) a base configured to engage a patient's eye, and (ii) at least one guide passageway configured to receive and guide the needle relative to the patient's eye.

Example 17

The apparatus of Example 16, wherein the guidance device further comprises a lens engagement feature configured to removably couple with a viewing lens.

Example 18

A method of subretinal administration of a therapeutic agent, the method comprising the steps of: (a) inserting a needle through the sclera and the choroid of a patient's eye to a position between the choroid and the retina at a first region of the eye; (b) injecting a first fluid between the choroid and the retina to form a leading bleb between the choroid and the retina, wherein the first fluid is injected via the needle; (c) extending a catheter from a distal end of the needle into the leading bleb; (d) extending the catheter further between the choroid and the retina to a second region of the eye; and (e) injecting a second fluid between the choroid and the retina of the patient's eye to form another bleb between the choroid and the retina, wherein the second fluid is injected via the catheter.

Example 19

The method of Example 18, further comprising securing a guidance device to the eye, wherein the guidance device defines a guide passageway, wherein the act of inserting the needle through the sclera and the choroid further comprises inserting the needle through the guide passageway of the guidance device, wherein the guide passageway guides the needle along a path to position the needle through the sclera and the choroid.

Example 20

An apparatus comprising: (a) an annular base, wherein the annular base has a bottom surface configured to complement a contour of a patient's eye; (b) a plurality of suture openings associated with the annular base, wherein the suture openings are configured to receive sutures to thereby secure the annular base to the patient's eye; (c) a guidance member extending downwardly from the annular base, wherein the guidance member defines at least one guide passageway, wherein the guide passageway is configured to receive and guide a needle along a predefined path relative to the patient's eye; and (d) a lens coupling feature, wherein the lens coupling feature is configured to removably secure a lens relative to the annular base.

Example 21

A method of subretinal administration of a therapeutic agent, the method comprising the steps of inserting a needle through the sclera and the choroid of a patient's eye to a position between the choroid and the retina at a first region of the eye; infusing a first fluid between the choroid and the retina to form a leading bleb between the choroid and the retina; extending a catheter from a distal end of the needle into the leading bleb; extending the catheter between the choroid and the retina to a second region of the eye; and infusing a second fluid between the choroid and the retina of the patient's eye to form another bleb between the choroid and the retina.

Example 22

The method of Example 21, wherein the second region of the eye is posterior to the first region of the eye.

Example 23

The method of any one of Examples 21 through 22, wherein the second fluid is a therapeutic agent.

Example 24

The method of any one of Examples 21 through 23, wherein the method further comprises the step of monitoring the interior of the eye for tenting of the choroid.

Example 25

The method of any one of Examples 21 through 24, wherein the method further comprises the step of monitoring the interior of the eye for tenting of the retina.

Example 26

The method of any one of Examples 21 through 25, wherein catheter comprises an illuminating section.

Example 27

The method of any one of Examples 21 through 26, wherein the method further comprises the step of securing a guidance device to the eye.

Example 28

The method of Example 27, wherein the step of securing the guidance device to the eye is accomplished using sutures.

Example 29

The method of any one of Examples 27 through 28, wherein the guidance device comprises at least one guidance bore.

Example 30

The method of Example 29, wherein the method further comprises the step of inserting the needle through the at least one guidance bore of the guidance device.

Example 31

The method of any one of Examples 29 through 30, wherein the at least one guidance bore comprises a plurality of guidance bores, wherein each guidance bore of the plurality of guidance bores defines a unique path.

Example 32

The method of any one of Examples 27 through 31, wherein the guidance device is configured to be selectively secured with a viewing lens.

Example 33

The method of Example 32, wherein the method further comprises the step of monitoring the interior of the eye through the viewing lens.

Example 34

The method of any one of Examples 32 through 33, wherein the guidance device comprises a support frame selectively compatible with the viewing lens.

Example 35

The method of any one of Examples 21 through 34, wherein the first fluid is Healon® OVD.

Example 36

A guidance device for use during subretinal administration of a therapeutic agent, the guidance device comprising: a base, wherein a bottom surface of the base mirrors the contour of a patient's eye, wherein the base is configured to be secured to a patient's eye; and a guidance anchor, wherein the guidance anchor extends from the base, wherein a bottom surface of the guidance anchor mirrors the contour of a patient's eye, wherein the guidance anchor comprises at least one guidance bore extending through the guidance anchor, wherein the guidance bore is configured to receive a needle so as to direct the needle along path relative to a patient's eye, wherein the path directs the needle into the interior of a patient's eye.

Example 37

The guidance device of Example 36 or any of the following Examples, wherein the base comprises at least one suture loop.

Example 38

The guidance device of Example 36 or any of the following Examples, wherein the at least one guidance bore comprises a plurality of guidance bores, wherein each guidance bore of the plurality of guidance bores defines a unique path along which needle may be directed.

Example 39

An instrument for use during subretinal administration of a therapeutic agent, the instrument device comprising: a body, wherein the body comprises a distal end and a proximal end; a needle, wherein the needle comprises a distal end and a proximal end, wherein the needle extends distally from the body, wherein the needle defines a lumen, wherein the needle is fluidly coupled with a fluid source, wherein the fluid source is configured to provide fluid to the distal end of the needle; a catheter, wherein the catheter comprises a distal end and a proximal end, wherein the catheter is slidably disposed within the lumen of the needle, wherein the catheter is translatable within and relative to the needle, wherein the catheter defines a lumen, wherein the catheter is fluidly coupled with a fluid source, wherein the fluid source is configured to provide fluid to the distal end of the catheter; and a first actuator assembly, wherein the first actuator assembly is configured to translate the catheter within and relative to the needle.

Example 40

The guidance device of Example 39, wherein the needle is configured to translate relative to the body, wherein the instrument further comprises a second actuator assembly, wherein the second actuator assembly is configured to translate the needle relative to the body.

VIII. MISCELLANEOUS

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of delivering fluid to an eye of a patient, the method comprising:
   (a) inserting a fluid delivery assembly into the eye of the patient;
   (b) moving the fluid delivery assembly in the eye of the patient toward a first location in the eye of the patient, the act of moving the fluid delivery assembly in the eye of the patient toward the first location in the eye of the patient comprising moving the fluid delivery assembly along a curvature of the eye within a space between a choroid layer of the eye and a sclera layer of the eye;
   (c) arresting movement of the fluid delivery assembly at a first time at the first location in the eye of the patient;
   (d) delivering a first volume of fluid to a first subretinal site in the eye of the patient via a fluid delivery member of the fluid delivery assembly while the fluid delivery assembly is arrested at the first location;
   (e) moving the fluid delivery member within the eye of the patient, after delivering the first volume of fluid, toward a second location in the eye of the patient, without removing the fluid delivery assembly from the eye of the patient;
   (f) arresting movement of the fluid delivery member at a second time at the second location in the eye of the patient; and
   (g) delivering a second volume of fluid to a second subretinal site in the eye of the patient via the fluid delivery member while the fluid delivery member is arrested at the second location, wherein the delivered first volume of fluid causes a first portion of a retinal layer of the eye to separate from the choroid layer of the eye, wherein the delivered second volume of fluid causes a second portion of the retinal layer of the eye to separate from the choroid layer of the eye.

2. The method of claim 1, the fluid delivery assembly including a catheter and a needle.

3. The method of claim 2, the catheter being slidably disposed within the needle.

4. The method of claim 3, the fluid delivery member comprising the catheter.

5. The method of claim 2, the act of moving the fluid delivery member within the eye of the patient toward the second location in the eye of the patient comprising moving the catheter along a subretinal space between the first subretinal site and the second subretinal site.

6. The method of claim 1, the method being performed without traversing a vitreous region of the eye.

7. The method of claim 1, the method being performed without traversing the retinal layer of the eye.

8. The method of claim 1, the act of moving the fluid delivery assembly in the eye of the patient toward the first location comprising penetrating the sclera layer of the eye.

9. The method of claim 8, the act of moving the fluid delivery assembly in the eye of the patient toward the first location further comprising penetrating the choroid layer of the eye.

10. The method of claim 1, the first volume of fluid comprising a bleb fluid.

11. The method of claim 10, the bleb fluid comprising a salt solution.

12. The method of claim 10, the second volume of fluid comprising a therapeutic agent.

13. The method of claim 1, the second subretinal site being located in a posterior region of the eye of the patient.

14. The method of claim 13, the second subretinal site being adjacent to an area of geographic atrophy of the retinal layer of the eye of the patient.

15. The method of claim 13, the second subretinal site being superior to a macula of the eye of the patient.

16. The method of claim 1, further comprising securing a guide to the eye of the patient, the act of inserting the fluid delivery assembly into the eye of the patient including inserting the fluid delivery assembly through the guide.

17. A method of delivering fluid to an eye of a patient, the method comprising:
 (a) inserting a fluid delivery assembly into the eye of the patient;
 (b) moving the fluid delivery assembly in the eye of the patient toward a first location in the eye of the patient, without traversing a vitreous region or retinal layer of the eye, the act of moving the fluid delivery assembly in the eye of the patient toward the first location in the eye of the patient comprising moving the fluid delivery assembly posteriorly along a space between a choroid layer of the eye and a sclera layer of the eye;
 (c) arresting movement of the fluid delivery assembly at a first time at the first location in the eye of the patient;
 (d) delivering a first volume of fluid to a first subretinal site in the eye of the patient via a fluid delivery member of the fluid delivery assembly while the fluid delivery assembly is arrested at the first location;
 (e) moving at least a portion of the fluid delivery assembly posteriorly along a space between two layers within the eye of the patient, after delivering the first volume of fluid, toward a second location in the eye of the patient, without traversing the vitreous region or retinal layer of the eye;
 (f) arresting movement of the at least a portion of the fluid delivery assembly at a second time at the second location in the eye of the patient; and
 (g) delivering a second volume of fluid to a second subretinal site in the eye of the patient via the fluid delivery member while the at least a portion of the fluid delivery assembly is arrested at the second location.

18. The method of claim 17, the space between two layers within the eye of the patient comprising a space between the retinal layer of the eye and the choroid layer of the eye.

19. A method of delivering fluid to an eye of a patient, the method comprising:
 (a) securing a guide to the eye of the patient;
 (b) inserting a fluid delivery assembly into the eye of the patient via the guide, the act of inserting the fluid delivery assembly into the eye of the patient comprising moving the fluid delivery assembly along a curvature of the eye within a space between a choroid layer of the eye and a sclera layer of the eye;
 (c) delivering a first volume of fluid to a first subretinal site in the eye of the patient via the fluid delivery assembly; and
 (d) delivering a second volume of fluid to a second subretinal site in the eye of the patient via the fluid delivery assembly while a portion of the fluid delivery assembly is radially outward of at least a portion of the first subretinal site relative to an optic axis of the eye;
 the acts of inserting, delivering the first volume of fluid, and delivering the second volume of fluid all being performed without:
 (i) traversing a vitreous region of the eye of the patient,
 (ii) traversing a retinal layer of the eye of the patient, and
 (iii) removing the fluid delivery assembly from the eye of the patient.

\* \* \* \* \*